US011560563B2

(12) United States Patent
Weingärtner et al.

(10) Patent No.: US 11,560,563 B2
(45) Date of Patent: Jan. 24, 2023

(54) SIRNAS WITH VINYLPHOSPHONATE AT THE 5' END OF THE ANTISENSE STRAND

(71) Applicant: SILENCE THERAPEUTICS GMBH, Berlin (DE)

(72) Inventors: Adrien Weingärtner, Berlin (DE); Lucas Bethge, Potsdam (DE)

(73) Assignee: SILENCE THERAPEUTICS GMBH, Berlin (DE)

( * ) Notice: Subject to any disclaimer, the term of this patent is extended or adjusted under 35 U.S.C. 154(b) by 110 days.

(21) Appl. No.: 17/045,123

(22) PCT Filed: Apr. 5, 2019

(86) PCT No.: PCT/EP2019/058615
§ 371 (c)(1),
(2) Date: Oct. 2, 2020

(87) PCT Pub. No.: WO2019/193144
PCT Pub. Date: Oct. 10, 2019

(65) Prior Publication Data

US 2021/0147840 A1 May 20, 2021

(30) Foreign Application Priority Data

Apr. 5, 2018 (WO) ................. PCT/EP2018/058764
Sep. 28, 2018 (EP) .................................... 18197795

(51) Int. Cl.
*C12N 15/113* (2010.01)
*A61K 47/54* (2017.01)

(52) U.S. Cl.
CPC .......... *C12N 15/113* (2013.01); *A61K 47/549* (2017.08); *C12N 2310/14* (2013.01); *C12N 2310/312* (2013.01); *C12N 2310/315* (2013.01); *C12N 2310/321* (2013.01); *C12N 2310/322* (2013.01); *C12N 2310/345* (2013.01); *C12N 2310/346* (2013.01); *C12N 2310/3515* (2013.01); *C12N 2320/51* (2013.01)

(58) Field of Classification Search
None
See application file for complete search history.

(56) References Cited

U.S. PATENT DOCUMENTS

| | | | |
|---|---|---|---|
| 8,324,179 | B2 | 12/2012 | Chen et al. |
| 8,987,435 | B2 | 3/2015 | Swayze et al. |
| 8,993,738 | B2 | 3/2015 | Prakash et al. |
| 9,896,688 | B2 | 2/2018 | Chang et al. |
| 10,023,861 | B2 | 7/2018 | Prakash et al. |
| 10,087,210 | B2 | 10/2018 | Prakash et al. |
| 10,738,308 | B2 | 8/2020 | Chang et al. |
| 2018/0265869 | A1 | 9/2018 | Guidry et al. |
| 2019/0136234 | A1 | 5/2019 | Prakash et al. |

FOREIGN PATENT DOCUMENTS

| | | | |
|---|---|---|---|
| EP | 2601204 | A2 | 6/2013 |
| EP | 2958998 | A1 | 12/2015 |
| EP | 3366772 | A1 | 8/2018 |
| WO | 2009/073809 | A2 | 6/2009 |
| WO | 2010/048585 | A2 | 4/2010 |
| WO | 2011/104169 | A1 | 9/2011 |
| WO | 2011/139702 | A2 | 11/2011 |
| WO | 2013/033230 | A1 | 3/2013 |
| WO | 2014/130607 | A1 | 8/2014 |
| WO | 2016/028649 | A1 | 2/2016 |

*Primary Examiner* — Tracy Vivlemore
(74) *Attorney, Agent, or Firm* — Marshall, Gerstein & Borun LLP

(57) ABSTRACT

The present invention relates to nucleic acids for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited. The first strand of the nucleic acid has a terminal 5' (E)-vinylphosphonate nucleotide that is linked to the second nucleotide in the first strand by a phosphodiester linkage.

16 Claims, 12 Drawing Sheets

Specification includes a Sequence Listing.

SEQUENCE LISTING

```
<160> NUMBER OF SEQ ID NOS: 77

<210> SEQ ID NO 1
<211> LENGTH: 21
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 1

uuauagagca agaacacugu u                                               21


<210> SEQ ID NO 2
<211> LENGTH: 21
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 2

aacaguguuc uugcucuaua a                                               21


<210> SEQ ID NO 3
<211> LENGTH: 21
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 3

uuauagagca agaacacugu u                                               21


<210> SEQ ID NO 4
<211> LENGTH: 21
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 4

aacaguguuc uugcucuaua a                                               21


<210> SEQ ID NO 5
<211> LENGTH: 21
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 5

uuauagagca agaacacugu u                                               21


<210> SEQ ID NO 6
<211> LENGTH: 21
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description
```

<400> SEQUENCE: 6
aacaguguuc uugcucuaua a 21

<210> SEQ ID NO 7
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 7
aaccagaaga agcagguga 19

<210> SEQ ID NO 8
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 8
ucaccugcuu cuucugguu 19

<210> SEQ ID NO 9
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 9
uaccagaaga agcagguga 19

<210> SEQ ID NO 10
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 10
ucaccugcuu cuucuggua 19

<210> SEQ ID NO 11
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 11
uaccagaaga agcagguga 19

<210> SEQ ID NO 12
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 12

```
ucaccugcuu cuucuggua                                                19


<210> SEQ ID NO 13
<211> LENGTH: 19
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 13

aauguuuucc ugcugacgg                                                19


<210> SEQ ID NO 14
<211> LENGTH: 19
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 14

ccgucagcag gaaaacauu                                                19


<210> SEQ ID NO 15
<211> LENGTH: 19
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 15

uauguuuucc ugcugacgg                                                19


<210> SEQ ID NO 16
<211> LENGTH: 19
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 16

ccgucagcag gaaaacaua                                                19


<210> SEQ ID NO 17
<211> LENGTH: 19
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 17

ucuucuuaaa cugaguuuc                                                19


<210> SEQ ID NO 18
<211> LENGTH: 19
<212> TYPE: RNA
<213> ORGANISM: Artificial Sequence
<220> FEATURE:
<223> OTHER INFORMATION: siRNA strand - modified_nucleotides, modified
      as per summary sequence table at the end of the description

<400> SEQUENCE: 18
```

gaaacucagu uuaagaaga 19

<210> SEQ ID NO 19
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 19
ucuucuuaaa cugaguuuc 19

<210> SEQ ID NO 20
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 20
gaaacucagu uuaagaaga 19

<210> SEQ ID NO 21
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 21
ucgaaguauu ccgcguacg 19

<210> SEQ ID NO 22
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 22
cguacgcgga auacuucga 19

<210> SEQ ID NO 23
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 23
aaccagaaga agcagguga 19

<210> SEQ ID NO 24
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 24
ucaccugcuu cuucugguu 19

<210> SEQ ID NO 25
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 25
uaccagaaga agcagguga 19

<210> SEQ ID NO 26
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 26
ucaccugcuu cuucuggua 19

<210> SEQ ID NO 27
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 27
uaccagaaga agcagguga 19

<210> SEQ ID NO 28
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 28
ucaccugcuu cuucuggua 19

<210> SEQ ID NO 29
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 29
uaccagaaga agcagguga 19

<210> SEQ ID NO 30
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 30
ucaccugcuu cuucuggua 19

<210> SEQ ID NO 31
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 31
ucuucuuaaa cugaguuuc 19

<210> SEQ ID NO 32
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 32
gaaacucagu uuaagaaga 19

<210> SEQ ID NO 33
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 33
ucuucuuaaa cugaguuuc 19

<210> SEQ ID NO 34
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 34
gaaacucagu uuaagaaga 19

<210> SEQ ID NO 35
<211> LENGTH: 22
<212> TYPE: DNA
<213> ORGANISM: Artificial Sequence
<220> FEATURE:
<223> OTHER INFORMATION: primer

<400> SEQUENCE: 35
tggacaccaa atcgtactgg aa 22

<210> SEQ ID NO 36
<211> LENGTH: 22
<212> TYPE: DNA
<213> ORGANISM: Artificial Sequence
<220> FEATURE:
<223> OTHER INFORMATION: primer

<400> SEQUENCE: 36
cagagtcgtt ggctgtgaaa ac 22

<210> SEQ ID NO 37
<211> LENGTH: 27

<212> TYPE: DNA
<213> ORGANISM: Artificial Sequence
<220> FEATURE:
<223> OTHER INFORMATION: probe - modified as per summary sequence table at the end of the description

<400> SEQUENCE: 37 actttggcatt tccccgttcc atgaatt 27

<210> SEQ ID NO 38
<211> LENGTH: 17
<212> TYPE: DNA
<213> ORGANISM: Artificial Sequence
<220> FEATURE:
<223> OTHER INFORMATION: primer

<400> SEQUENCE: 38
ccgccaaagc ccagaag 17

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
ggtccctccc caaaggaata g 21

<210> SEQ ID NO 40
<211> LENGTH: 28
<212> TYPE: DNA
<213> ORGANISM: Artificial Sequence
<220> FEATURE:
<223> OTHER INFORMATION: probe - modified as per summary sequence table at the end of the description

<400> SEQUENCE: 40
cagcacccgc ctgggaactt actacaac 28

<210> SEQ ID NO 41
<211> LENGTH: 22
<212> TYPE: DNA
<213> ORGANISM: Artificial Sequence
<220> FEATURE:
<223> OTHER INFORMATION: primer

<400> SEQUENCE: 41
ggcaagcctt atgtcatctc gt 22

<210> SEQ ID NO 42
<211> LENGTH: 23
<212> TYPE: DNA
<213> ORGANISM: Artificial Sequence
<220> FEATURE:
<223> OTHER INFORMATION: primer

<400> SEQUENCE: 42
ggaatggttt tcccatggta ctt 23

<210> SEQ ID NO 43
<211> LENGTH: 28
<212> TYPE: DNA
<213> ORGANISM: Artificial Sequence
<220> FEATURE:
<223> OTHER INFORMATION: probe - modified as per summary sequence table at the end of the description

<400> SEQUENCE: 43
tgaaatgtct ccgctattac gctggctg 28

<210> SEQ ID NO 44
<211> LENGTH: 22
<212> TYPE: DNA
<213> ORGANISM: Artificial Sequence
<220> FEATURE:
<223> OTHER INFORMATION: primer

<400> SEQUENCE: 44
aaagaggcca gtcaagctgt tc 22

<210> SEQ ID NO 45
<211> LENGTH: 22
<212> TYPE: DNA
<213> ORGANISM: Artificial Sequence
<220> FEATURE:
<223> OTHER INFORMATION: primer

<400> SEQUENCE: 45
ggtgggatca cttctgtttt gg 22

<210> SEQ ID NO 46
<211> LENGTH: 29
<212> TYPE: DNA
<213> ORGANISM: Artificial Sequence
<220> FEATURE:
<223> OTHER INFORMATION: probe - modified as per summary sequence table at the end of the description

<400> SEQUENCE: 46
cagcaacaca ctgcatctgg tctctacca 29

<210> SEQ ID NO 47
<211> LENGTH: 22
<212> TYPE: DNA
<213> ORGANISM: Artificial Sequence
<220> FEATURE:
<223> OTHER INFORMATION: primer

<400> SEQUENCE: 47
caccgccaaa tttaactgca ga 22

<210> SEQ ID NO 48
<211> LENGTH: 24
<212> TYPE: DNA
<213> ORGANISM: Artificial Sequence
<220> FEATURE:
<223> OTHER INFORMATION: primer

<400> SEQUENCE: 48
aagggtttga taagttctag ctgt 24

<210> SEQ ID NO 49
<211> LENGTH: 31
<212> TYPE: DNA
<213> ORGANISM: Artificial Sequence
<220> FEATURE:
<223> OTHER INFORMATION: probe - modified as per summary sequence table at the end of the description

<400> SEQUENCE: 49
tgcacagtat ccttttgaag accataaccc a 31

<210> SEQ ID NO 50
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 50
aaccagaaga agcagguga 19

<210> SEQ ID NO 51
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 51
ucaccugcuu cuucugguu 19

<210> SEQ ID NO 52
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 52
uaccagaaga agcagguga 19

<210> SEQ ID NO 53
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 53
ucaccugcuu cuucuggua 19

<210> SEQ ID NO 54
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 54
uaccagaaga agcagguga 19

<210> SEQ ID NO 55
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 55
ucaccugcuu cuucuggua 19

<210> SEQ ID NO 56
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 56
uaccagaaga agcagguga 19

<210> SEQ ID NO 57
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 57
ucaccugcuu cuucuggua 19

<210> SEQ ID NO 58
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 58
uaccagaaga agcagguga 19

<210> SEQ ID NO 59
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 59
ucaccugcuu cuucuggua 19

<210> SEQ ID NO 60
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 60
ucgaaguauu ccgcguacg 19

<210> SEQ ID NO 61
<211> LENGTH: 19
<212> TYPE: RNA
<213> ORGANISM: Artificial Sequence
<220> FEATURE:
<223> OTHER INFORMATION: siRNA strand - modified_nucleotides, modified as per summary sequence table at the end of the description

<400> SEQUENCE: 61
cguacgcgga auacuucga 19

<210> SEQ ID NO 62

<211> LENGTH: 22
<212> TYPE: DNA
<213> ORGANISM: Artificial Sequence
<220> FEATURE:
<223> OTHER INFORMATION: primer

<400> SEQUENCE: 62
caccgccaaa tttaactgca ga 22

<210> SEQ ID NO 63
<211> LENGTH: 24
<212> TYPE: DNA
<213> ORGANISM: Artificial Sequence
<220> FEATURE:
<223> OTHER INFORMATION: primer

<400> SEQUENCE: 63
aagggtttga taagttctag ctgt 24

<210> SEQ ID NO 64
<211> LENGTH: 31
<212> TYPE: DNA
<213> ORGANISM: Artificial Sequence
<220> FEATURE:
<223> OTHER INFORMATION: probe - modified as per summary sequence table at the end of the description

<400> SEQUENCE: 64
tgcacagtat ccttttgaag accataaccc a 31

<210> SEQ ID NO 65
<211> LENGTH: 17
<212> TYPE: DNA
<213> ORGANISM: Artificial Sequence
<220> FEATURE:
<223> OTHER INFORMATION: primer

<400> SEQUENCE: 65
ccgccaaagc ccagaag 17

<210> SEQ ID NO 66
<211> LENGTH: 21
<212> TYPE: DNA
<213> ORGANISM: Artificial Sequence
<220> FEATURE:
<223> OTHER INFORMATION: primer

<400> SEQUENCE: 66
ggtccctccc caaaggaata g 21

<210> SEQ ID NO 67
<211> LENGTH: 28
<212> TYPE: DNA
<213> ORGANISM: Artificial Sequence
<220> FEATURE:
<223> OTHER INFORMATION: probe - modified as per summary sequence table at the end of the description

<400> SEQUENCE: 67
cagcacccgc ctgggaactt actacaac 28

<210> SEQ ID NO 68
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 68
uaccagaaga agcagguga 19

<210> SEQ ID NO 69
<211> LENGTH: 19
<212> TYPE: RNA
<213> ORGANISM: Artificial Sequence
<220> FEATURE:
<223> OTHER INFORMATION: siRNA strand

<400> SEQUENCE: 69
ucaccugcuu cuucuggua 19

<210> SEQ ID NO 70
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 70
ucaccugcuu cuucuggua 19

<210> SEQ ID NO 71
<211> LENGTH: 21
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 71
uuauagagca agaacacugu u 21

<210> SEQ ID NO 72
<211> LENGTH: 21
<212> TYPE: RNA
<213> ORGANISM: Artificial Sequence
<220> FEATURE:
<223> OTHER INFORMATION: siRNA strand

<400> SEQUENCE: 72
aacaguguuc uugcucuaua a 21

<210> SEQ ID NO 73
<211> LENGTH: 21
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 73
aacaguguuc uugcucuaua a 21

<210> SEQ ID NO 74
<211> LENGTH: 19
<212> TYPE: RNA
<213> ORGANISM: Artificial Sequence
<220> FEATURE:
<223> OTHER INFORMATION: siRNA strand - sequence modified as per summary sequence table at the end of the description

<400> SEQUENCE: 74

-continued

```
ucuucuuaaa cugaguuuc                                                19


<210> SEQ ID NO 75
<211> LENGTH: 19
<212> TYPE: RNA
<213> ORGANISM: Artificial Sequence
<220> FEATURE:
<223> OTHER INFORMATION: siRNA strand

<400> SEQUENCE: 75

gaaacucagu uuaagaaga                                                19


<210> SEQ ID NO 76
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 76

gaaacucagu uuaagaaga                                                19


<210> SEQ ID NO 77
<211> LENGTH: 19
<212> TYPE: RNA
<213> ORGANISM: Artificial Sequence
<220> FEATURE:
<223> OTHER INFORMATION: siRNA strand - sequence modified as per summary
      sequence table at the end of the description

<400> SEQUENCE: 77

gaaacucagu uuaagaaga                                                19
```

SIRNAS WITH VINYLPHOSPHONATE AT THE 5' END OF THE ANTISENSE STRAND

FIELD OF THE INVENTION

The present invention relates to siRNAs with a vinylphosphonate at the 5' end of the antisense strand. It further relates to therapeutic uses of such siRNA for the treatment of diseases, disorders and syndromes.

BACKGROUND

Double-stranded RNA (dsRNA) able to complementarily bind expressed mRNA has been shown to be able to block gene expression (Fire et al, 1998 and Elbashir et al, 2001) by a mechanism that has been termed RNA interference (RNAi). Short dsRNAs direct gene-specific, post-transcriptional silencing in many organisms, including vertebrates, and have become a useful tool for studying gene function. RNAi is mediated by the RNA-induced silencing complex (RISC), a sequence-specific, multi-component nuclease that destroys messenger RNAs homologous to the silencing trigger loaded into the RISC complex. Interfering RNA (iRNA) such as siRNAs, antisense RNA, and micro-RNA are oligonucleotides that prevent the formation of proteins by gene-silencing i.e. inhibiting gene translation of the protein through degradation of mRNA molecules. Gene-silencing agents are becoming increasingly important for therapeutic applications in medicine.

However, maintaining the stability and activity of nucleic acids, such as RNA, in vivo has proved challenging to those in the field of developing nucleic acid molecules for therapeutic use, particularly because of cellular metabolic enzymes which degrade nucleic acids and limit their activity.

siRNA mediated gene silencing requires siRNA loading into RNA-induced silencing complex (RISC). 5' phosphate on the siRNA is known to be critical for efficient RISC loading. Enzymes such as phosphatases remove the 5'phosphate of siRNA resulting in dephosphorylated siRNAs that are less efficiently incorporated into RISC and therefore have reduced silencing activity.

Thus, means for improving stability and activity of oligonucleotides, in particular double stranded siRNAs, in vivo is becoming increasingly important. In the present invention, it has been unexpectedly found that a nucleic acid in accordance with the present invention has increased activity.

SUMMARY OF INVENTION

The present invention provides a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited, wherein the first strand has a terminal 5' (E)-vinylphosphonate nucleotide, characterised in that the terminal 5' (E)-vinylphosphonate nucleotide is linked to the second nucleotide in the first strand by a phosphodiester linkage.

In the nucleic acid of the invention, the first strand may include more than 1 phosphodiester linkage.

In the nucleic acid of the invention, the first strand may comprise phosphodiester linkages between at least the terminal three 5' nucleotides.

In the nucleic acid of the invention, the first strand may comprise phosphodiester linkages between at least the terminal four 5' nucleotides.

In the nucleic acid of the invention, the first strand may include at least one phosphorothioate (ps) linkage.

In the nucleic acid of the invention, the first strand may further comprise a phosphorothioate linkage between the terminal two 3' nucleotides or phosphorothioate linkages between the terminal three 3' nucleotides. The linkages between the other nucleotides in the first strand may be phosphodiester linkages.

In the nucleic acid of the invention, the first strand may include more than 1 phosphorothioate linkage.

In the nucleic acid of the invention, the second strand may comprise a phosphorothioate linkage between the terminal two 3' nucleotides or phosphorothioate linkages between the terminal three 3' nucleotides.

In the nucleic acid of the invention, the second strand may comprise a phosphorothioate linkage between the terminal two 5' nucleotides or phosphorothioate linkages between the terminal three 5' nucleotides.

In the nucleic acid of the invention, the terminal 5' (E)-vinylphosphonate nucleotide may be an RNA nucleotide.

Preferably, the terminal 5' (E)-vinylphosphonate nucleotide is an RNA nucleotide, more preferably a (vp)-U.

In the nucleic acid of the invention, the first strand of the nucleic acid may have a length in the range of 15-30 nucleotides. Preferably, the first strand of the nucleic acid has a length in the range of 19-25 nucleotides.

In the nucleic acid of the invention, the second strand of the nucleic acid may have a length in the range of 15-30 nucleotides. Preferably, the second strand of the nucleic acid has a length in the range of 19-25 nucleotides.

The nucleic acid of the invention may be blunt ended at both ends.

The present invention further provides a conjugate for inhibiting expression of a target gene in a cell, said conjugate comprising a nucleic acid portion and ligand portion, said nucleic acid portion comprising a nucleic acid as defined anywhere herein.

In the conjugate of the invention, the second strand of the nucleic acid may be conjugated to the ligand portion.

In the conjugate of the invention, the ligand portion may comprise one or more GalNAc ligands and derivatives thereof, such as comprising a GalNAc moiety at the 5' end of the second strand of the nucleic acid.

In the conjugate of the invention, the ligand portion may comprise a linker moiety and a targeting ligand, and wherein the linker moiety links the targeting ligand to the nucleic acid portion.

The present invention further provides a conjugate for inhibiting expression of a TMPRSS6 gene in a cell.

The present invention further provides a composition comprising a nucleic acid as defined anywhere herein and a physiologically acceptable excipient.

The present invention further provides a composition comprising a conjugate as defined anywhere herein and a physiologically acceptable excipient.

The present invention further provides a nucleic acid as defined anywhere herein for use in the treatment of a disease or disorder.

The present invention further provides a conjugate as defined anywhere herein for use in the treatment of a disease or disorder.

The present invention further provides a composition as defined anywhere herein for use in the treatment of a disease or disorder.

DETAILED DESCRIPTION OF INVENTION

The present invention relates to a nucleic acid which is double stranded and directed to an expressed RNA transcript of a target gene and compositions thereof. These nucleic acids can be used in the treatment of a variety of diseases and disorders where reduced expression of target gene products is desirable.

A first aspect of the invention relates to a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited, wherein the first strand has a terminal 5' (E)-vinylphosphonate nucleotide, wherein the terminal 5' (E)-vinylphosphonate nucleotide is linked to the second nucleotide in the first strand by a phosphodiester linkage.

Vinylphosphonate

A terminal 5'-(E)-vinylphosphonate nucleotide is a nucleotide wherein the natural phosphate group at the 5' end has been replaced with a (E)-vinylphosphonate. A 5'-(E)-vinylphosphonate is a phosphate at the 5' end of a nucleotide strand in which the bridging 5'-oxygen atom is replaced with a methynyl (—CH═) group:

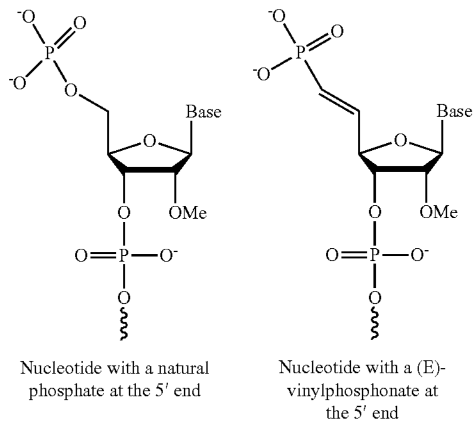

A 5'-(E)-vinylphosphonate is a 5' phosphate mimic. A biological mimic is a molecule that is capable of carrying out the same function as and is structurally very similar to the original molecule that is being mimicked. In the context of the present invention, 5'-(E)-vinylphosphonate mimics the function of a normal 5' phosphate, e.g. enabling efficient RISC loading. In addition, because of its slightly altered structure, 5'-(E)-vinylphosphonate is capable of stabilizing the 5' end nucleotide by protecting it from dephosphorylation by enzymes such as phosphatases.

The present inventors have surprisingly found that siRNAs with a terminal 5'-(E)-vinylphosphonate nucleotide, wherein the terminal 5'-(E)-vinylphosphonate nucleotide is linked to the second nucleotide in the first strand by a phosphodiester linkage have better gene silencing activity, i.e. results in a decrease in target mRNA expression, compared with siRNAs with a terminal 5'-(E)-vinylphosphonate nucleotide, wherein the terminal 5'-(E)-vinylphosphonate nucleotide is linked to the second nucleotide in the first strand by a phosphorothioate linkage. Activity has also been compared with siRNAs comprising no terminal 5'-(E)-vinylphosphonate nucleotide and no phosphorothioate linkages at the 5' end of the first strand (i.e. comprises phosphodiester linkages at the 5' end), and siRNAs comprising no terminal 5'-(E)-vinylphosphonate nucleotide but with phosphorothioate linkages at the 5' end of the first strand (see FIGS. 1-4, 9-11 and 14).

Nucleic Acid

By nucleic acid it is meant a nucleic acid comprising two strands comprising nucleotides, that is able to interfere with gene expression. Inhibition may be complete or partial and results in down regulation of gene expression in a targeted manner. The nucleic acid comprises two separate polynucleotide strands; the first strand, which may also be a guide strand or antisense strand; and a second strand, which may also be a passenger strand or sense strand. The first strand and the second strand may be part of the same polynucleotide molecule that is self-complementary which 'folds' to form a double stranded molecule. The nucleic acid may be an siRNA molecule.

The nucleic acid may comprise ribonucleotides, modified ribonucleotides, deoxynucleotides, deoxyribonucleotides, or nucleotide analogues. The nucleic acid may further comprise a double-stranded nucleic acid portion or duplex region formed by all or a portion of the first strand (also known in the art as a guide strand or antisense strand) and all or a portion of the second strand (also known in the art as a passenger strand or sense strand). The duplex region is defined as beginning with the first base pair formed between the first strand and the second strand and ending with the last base pair formed between the first strand and the second strand, inclusive.

In the present invention, the 5'-(E)-vinylphosphonate nucleotide may be a 5'-(E)-vinylphosphonate RNA nucleotide.

Duplex

By duplex region it is meant the region in two complementary or substantially complementary oligonucleotides that form base pairs with one another, either by Watson-Crick base pairing or any other manner that allows for the formation of a duplex between oligonucleotide strands that are complementary or substantially complementary. Further, within the duplex region, 100% complementarity is not required; substantial complementarity is allowable within a duplex region. Substantial complementarity refers to complementarity between the strands such that they are capable of annealing under biological conditions. Techniques to empirically determine if two strands are capable of annealing under biological conditions are well known in the art. Alternatively, two strands can be synthesised and added together under biological conditions to determine if they anneal to one another.

The portion of the first strand and second strand that form at least one duplex region may be fully complementary and are at least partially complementary to each other.

Complementarity

Depending on the length of a nucleic acid, a perfect match in terms of base complementarity between the first strand and second strand is not necessarily required. However, the first and second strands must be able to hybridise under physiological conditions.

The complementarity between the first strand and second strand in the at least one duplex region may be perfect in that there are no nucleotide mismatches or additional/deleted nucleotides in either strand. Alternatively, the complementarity may not be perfect. The complementarity may be at least 70%, 75%, 80%, 85%, 90% or 95%.

The first strand and the second strand may each comprise a region of complementarity which comprises at least 15, preferably at least 16, more preferably at least 17, yet more preferably at least 18 and most preferably at least 19 contiguous nucleotides.

The nucleic acid involves the formation of a duplex region between all or a portion of the first strand and a portion of the target nucleic acid. The portion of the target nucleic acid that forms a duplex region with the first strand, defined as beginning with the first base pair formed between the first strand and the target sequence and ending with the last base pair formed between the first strand and the target sequence, inclusive, is the target nucleic acid sequence or simply, target sequence. The duplex region formed between the first strand and the second strand need not be the same as the duplex region formed between the first strand and the target sequence. That is, the second strand may have a sequence different from the target sequence. However, the first strand must be able to form a duplex structure with both the second strand and the target sequence, at least under physiological conditions.

The complementarity between the first strand and the target sequence may be perfect (no nucleotide mismatches or additional/deleted nucleotides in either nucleic acid).

The complementarity between the first strand and the target sequence may not be perfect. The complementarity may be from about 70% to about 100%. More specifically, the complementarity may be at least 70%, 80%, 85%, 90% or 95%, or an intermediate value.

The identity between the first strand and the complementary sequence of the target sequence may be from about 75% to about 100%. More specifically, the complementarity may be at least 75%, 80%, 85%, 90% or 95%, or an intermediate value, provided a nucleic acid is capable of reducing or inhibiting the expression of a target gene, preferably by RNAi.

A nucleic acid with less than 100% complementarity between the first strand and the target sequence may be able to reduce the expression of a target gene to the same level as a nucleic acid with perfect complementarity between the first strand and the target sequence. Alternatively, it may be able to reduce expression of a target gene to a level that is 20%, 30%, 40%, 50%, 60%, 70%, 80%, 90% or 100% of the level of expression achieved by the nucleic acid with perfect complementarity.

In a further aspect the nucleic acid as described herein may reduce the expression of a target gene in a cell by at least 10% compared to the level observed in the absence of an inhibitor, which may be the nucleic acid. All preferred features of any of the previous aspects also apply to this aspect. In particular, the expression of a target gene in a cell may be reduced to 90%, 80%, 70%, 60%, 50%, 40%, 30%, 20%, 15%, and intermediate values, than that observed in the absence of an inhibitor (which may be the nucleic acid).

Length

The nucleic acid may comprise a first strand and a second strand that are each from 19-25 nucleotides in length. The first strand and the second strand may be of the same lengths or different lengths.

In one embodiment, the nucleic acid may comprise a first strand and a second strand that are each 15-30, 15-25, 17-25, 17-23, 23-24, 19-21, 21-23 nucleotides in length. Preferably, he nucleic acid may comprise a first strand and a second strand that are each 19-21 nucleotides in length. The first and second strand may be of the same lengths or different lengths within these ranges.

In one embodiment, the nucleic acid may comprise a first strand and a second strand that are each 19 nucleotides in length.

In another embodiment, the nucleic acid may comprise a first strand and a second strand that are each 20 nucleotides in length.

In a further embodiment, the nucleic acid may comprise a first strand and a second strand that are each 21 nucleotides in length.

The nucleic acid may comprise a duplex region that consists of 19-25 nucleotide base pairs. The duplex region may consist of 17, 18, 19, 20, 21, 22, 23, 24 or 25 base pairs which may be contiguous.

The terminal 5'-(E)-vinylphosphonate nucleotide of the first strand may be any nucleotide (i.e. A, G, C or U). Preferably, it may be a U.

The nucleic acid may be blunt ended at both ends.

The nucleic acid may, at the end of the nucleic acid that comprises the 5' end of the first strand: a) be blunt ended or b) have a 3' overhang of at least one nucleotide.

PO and PS linkages

In the nucleic acid of the present invention, the terminal 5'-(E)-vinylphosphonate nucleotide is linked to the second nucleotide in the first strand by a phosphodiester linkage. The first strand may comprise more than one phosphodiester nucleotide (i.e. more than one internucleotide phosphodiester linkage).

In one embodiment, the first strand comprises phosphodiester linkages between at least the terminal three 5' nucleotides. In another embodiment, the first strand comprises phosphodiester linkages between at least the terminal four 5' nucleotides.

In one embodiment, the first strand comprises formula (Ia):

$$\text{(vp)-N(po)[N(po)]}_n\text{-} \quad \text{(Ia)}$$

where '(vp)' is the 5'-(E)-vinylphosphonate, 'N' is a nucleotide, 'po' is a phosphodiester linkage, and n is from 1 to (the total number of nucleotides in the first strand—2), preferably wherein n is from 1 to (the total number of nucleotides in the first strand—3), more preferably wherein n is from 1 to (the total number of nucleotides in the first strand—4).

Thus, in one embodiment, where the nucleic acid comprises a first strand that is 19 nucleotides in length, n is from 1 to (19-2), preferably (19-3), more preferably (19-4), i.e. n is from 1 to 17, preferably 1 to 16, more preferably 1 to 15.

Thus, in another embodiment, where the nucleic acid comprises a first strand that is 20 nucleotides in length, n is from 1 to (20-2), preferably (20-3), more preferably (20-4), i.e. n is from 1 to 18, preferably 1 to 17, more preferably 1 to 16.

Thus, in further embodiment, where the nucleic acid comprises a first strand that is 21 nucleotides in length, n is from 1 to (21-2), preferably (21-3), more preferably (21-4), i.e. n is from 1 to 19, preferably 1 to 18, more preferably 1 to 17.

In one embodiment, the first strand comprises formula (Ib):

$$\text{(vp)-N(po)[N(po)]}_n\text{[N(x)]}_m \quad \text{(Ib)}$$

where '(vp)' is the 5'-(E)-vinylphosphonate, 'N' is independently any nucleotide, such as a natural or modified ribonucleotide, 'po' is a phosphodiester linkage, n is at least 1, n+m+1 is the total number of nucleotides in the strand, and x is independently any linkage between two nucleotides, such as a phosphodiester linkage, a phosphorothioate linkage, and a phosphodithioate linkage.

The nucleic acid of the present invention may also comprise at least one phosphorothioate linkage in the first strand.

Phosphorothioates are generally thought in the art to be necessary at the ends of the siRNA strands to protect the siRNAs against degratdation, especially if the siRNAs are to be used in treatments. The inventors have surprisingly found that when a 5' vinylphosphonate is present at the 5' end of a strand, activity of the siRNAs is better when there are no phosphorothioate at the 5' end of the strand. This is surprising because it is generally thought in the art that such phosphorotiate linkages increase stability. It is therefore possible to replace the phosphorothioate linkages at the 5' of the antisense strand by a 5' vinylphosphonate and to thereby increase activity. This is desirable because phosphorothioate linkages, in contrast to phosphodiester linkages, are stereogenic centers.

The nucleic acid of the present invention may comprise more than 1 phosphorothioate linkage in the first strand.

In one embodiment, the first strand comprises a phosphorothioate linkage between the terminal two 3' nucleotides. In another embodiment, the first strand comprises a phosphorothioate linkage between the terminal three 3' nucleotides (i.e. defining two phosphorothioate linkages). In these embodiments, the linkages between the other nucleotides in the first strand are preferably phosphodiester linkages.

The second strand of the nucleic acid of the present invention may also comprise a phosphorothioate linkage between the terminal two, three or four 3' nucleotides.

In one embodiment, the second strand comprises a phosphorothioate linkage between the terminal two, three or four 5' nucleotides.

In one embodiment, the second strand comprises a phosphorothioate linkage between the terminal three 3' nucleotides and a phosphodiester linkage between the terminal three 5' nucleotides.

In one embodiment, the second strand comprises a phosphorothioate linkage between the terminal four 3' nucleotides and between the terminal four 5' nucleotides.

In one embodiment, the second strand comprises a phosphorothioate linkage between the terminal three 3' nucleotides and between the terminal three 5' nucleotides.

In one embodiment, the first strand comprises a phosphorothioate linkage between the terminal three 3' nucleotides and the second strand comprises a phosphorothioate linkage between the terminal three 3' nucleotides. In this embodiment, the linkages between the other nucleotides in the first strand and second strand are preferably phosphodiester linkages.

In one embodiment, the first strand comprises a phosphorothioate linkage between the terminal three 3' nucleotides and the second strand comprises a phosphorothioate linkage between the terminal four 3' nucleotides and between the terminal four 5' nucleotides. In this embodiment, the linkages between the other nucleotides in the first strand and second strand are preferably phosphodiester linkages.

In one embodiment, the first strand comprises a phosphorothioate linkage between the terminal three 3' nucleotides and the second strand comprises a phosphorothioate linkage between the terminal three 3' nucleotides and between the terminal three 5' nucleotides. In this embodiment, the linkages between the other nucleotides in the first strand and second strand are preferably phosphodiester linkages.

In one embodiment, the nucleic acid:

(i) has a terminal 5' (E)-vinylphosphonate nucleotide at the 5' end of the first strand;

(ii) has a phosphorothioate linkage between the terminal three 3' nucleotides on the first and second strand and between the terminal three 5' nucleotides on the second strand; and (iii) all remaining linkages between nucleotides of the first and/or of the second strand are phosphodiester linkages.

In one embodiment, the nucleic acid is an siRNA that inhibits expression of the target gene via RNAi.

2' Modifications Unmodified polynucleotides, particularly ribonucleotides, may be prone to degradation by cellular nucleases, and, as such, modifications/modified nucleotides may be included in the nucleic acid of the invention.

References herein to modifications of the nucleic acid of the present invention are in addition to the (E)-vinylphosphonate on the 5' terminal nucleotide of the first strand.

Modifications of the nucleic acid of the present invention generally provide a powerful tool in overcoming potential limitations including, but not limited to, in vitro and in vivo stability and bioavailability inherent to native RNA molecules. The nucleic acid according to the invention may be modified by chemical modifications. Modified nucleic acid can also minimise the possibility of inducing interferon activity in humans. Modification can further enhance the functional delivery of a nucleic acid to a target cell. The modified nucleic acid of the present invention may comprise one or more chemically modified ribonucleotides of either or both of the first strand or the second strand. A ribonucleotide may comprise a chemical modification of the base, sugar or phosphate moieties. The ribonucleic acid may be modified by substitution or insertion with analogues of nucleotides or bases.

One or more nucleotides on the second and/or first strand of the nucleic acid of the invention may be modified. A modified nucleotide can include modification of the sugar groups, particularly the 2'-hydroxyl group (OH) group. The 2'-OH can be modified or replaced with a number of different "oxy" or "deoxy" substituents.

Examples of "oxy"-2' hydroxyl group modifications include alkoxy or aryloxy (OR, e.g., R═H, alkyl, cycloalkyl, aryl, aralkyl, heteroaryl or sugar); polyethyleneglycols (PEG), $O(CH_2CH_2O)$, $CH_2CH_2OR$; "locked" nucleic acids (LNA) in which the 2' hydroxyl is connected, e.g., by a methylene bridge, to the 4' carbon of the same ribose sugar; O-AMINE (AMINE=$NH_2$; alkylamino, dialkylamino, heterocyclyl, arylamino, diaryl amino, heteroaryl amino, or diheteroaryl amino, ethylene diamine, polyamino) and aminoalkoxy, $O(CH_2)$, AMINE, (e.g., AMINE=$NH_2$; alkylamino, dialkylamino, heterocyclyl, arylamino, diaryl amino, heteroaryl amino, or diheteroaryl amino, ethylene diamine, polyamino).

"Deoxy" modifications include hydrogen halo; amino (e.g., $NH_2$; alkylamino, dialkylamino, heterocyclyl, arylamino, diaryl amino, heteroaryl amino, diheteroaryl amino, or amino acid); $NH(CH_2CH_2NH)_nCH_2CH_2$-AMINE (AMINE=$NH_2$; alkylamino, dialkylamino, heterocyclyl, arylamino, diaryl amino, heteroaryl amino, or diheteroaryl amino), —NHC(O)R (R=alkyl, cycloalkyl, aryl, aralkyl, heteroaryl or sugar), cyano; mercapto; alkyl-thio-alkyl; thioalkoxy; and alkyl, cycloalkyl, aryl, alkenyl and alkynyl, which may be optionally substituted with e.g., an amino functionality. Other substituents of certain embodiments include 2'-methoxyethyl, 2'-$OCH_3$, 2'-O-allyl, 2'-C-allyl, and 2'-fluoro.

In the nucleic acid of the invention, the first strand may be modified, to form modified nucleotides. In particular, one or more nucleotides on the second strand is modified, to form modified nucleotides. In the nucleic acid of the invention, the modification may be a modification at the 2'—OH group of the ribose sugar, optionally selected from 2'-O-methyl (2'-OMe) or 2'-F modifications.

In the nucleic acid of the invention, one or more or all of the odd numbered nucleotides of the first strand, numbered from the 5' end, may be a modified nucleotide having a first modification at the 2'—OH group of the ribose sugar and one or more or all of the even numbered nucleotides of the first strand, also numbered from the 5' end, may be a differently modified nucleotide having a second modification at the 2'—OH group of the ribose sugar, where the first and second modifications are different. Preferably, the first modification is a 2'-OMe and the second modification is a 2'-F, or vice versa.

Preferably, in the nucleic acid of the invention, there are no 2'-methoxyethyl modified nucleotides in the first strand.

A nucleic acid of the invention may have 1 modified nucleotide or a nucleic acid of the invention may have about 2-4 modified nucleotides, or a nucleic acid may have about 4-6 modified nucleotides, about 6-8 modified nucleotides, about 8-10 modified nucleotides, about 10-12 modified nucleotides, about 12-14 modified nucleotides, about 14-16 modified nucleotides about 16-18 modified nucleotides, about 18-20 modified nucleotides, about 20-22 modified nucleotides, about 22-24 modified nucleotides, 24-26 modified nucleotides or about 26-28 modified nucleotides. In each case the nucleic acid comprising said modified nucleotides retains at least 50% of its activity as compared to the same nucleic acid but without said modified nucleotides. The nucleic acid may retain 55%, 60%, 65%, 70%, 75%, 80%, 85%, 90%, 95% or 100% or an intermediate value of its activity as compared to the same nucleic acid but without said modified nucleotides, or may have more than 100% of the activity of the same nucleotide without said modified nucleotides.

The modified nucleotide may be a purine or a pyrimidine. At least half of the purines may be modified. At least half of the pyrimidines may be modified. All of the purines may be modified. All of the pyrimidines may be modified. The modified nucleotides may be selected from the group consisting of a 2'-OMe modified nucleotide, a 2' modified nucleotide, a 2'-deoxy-modified nucleotide, a 2'-amino-modified nucleotide, or a 2'-alkyl-modified nucleotide.

The nucleic acid may comprise a nucleotide comprising a modified base, wherein the base is selected from 2-aminoadenosine, 2,6-diaminopurine, inosine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

At least one modification may be 2'-OMe and/or at least one modification may be 2'-F. Further modifications as described herein may be present on the first and/or second strand.

Throughout the description of the invention, "same or common modification" means the same modification to any nucleotide, be that A, G, C or U modified with a group such as such as a methyl group or a fluoro group. Is it not taken to mean the same addition on the same nucleotide. For example, 2'-F-dU, 2'-F-dA, 2'-F-dC, 2'-F-dG are all considered to be the same or common modification, as are 2'-OMe-rU, 2'-OMe-rA; 2'-OMe-rC; 2'-OMe-rG. A 2'-F modification is a different modification to a 2'-OMe modification.

Preferably, the nucleic acid may comprise a modification and the second or further modification which are each and individually selected from the group comprising 2'-OMe modification and 2'-F modification. The nucleic acid may comprise a modification that is 2'-OMe that may be a first modification, and a second modification that is 2'-F.

As used herein, the term "inhibit", "down-regulate", or "reduce" with respect to gene expression means the expression of the gene, or level of RNA molecules or equivalent RNA molecules encoding one or more proteins or protein subunits (e.g., mRNA), or activity of one or more proteins or protein subunits or peptides, is reduced below that observed in the absence of a nucleic acid of the invention or in reference to an siRNA molecule with no known homology to human transcripts (herein termed non-silencing control). Such control may be conjugated and modified in an analogous manner to the molecule of the invention and delivered into the target cell by the same route; for example the expression may be reduced to 90%, 80%, 70%, 60%, 50%, 40%, 30%, 20%, 15% or less than that observed in the absence of an inhibitor (which may be the nucleic acid) or in the presence of a non-silencing control (which may be a nucleic acid that is non-complementary to the target sequence).

Modification Pattern

The nucleic acid may comprise one or more nucleotides on the second and/or first strands that are modified, to form modified nucleotides, specifically wherein the modification is a modification at the 2'—OH group of the ribose sugar. Alternating nucleotides may be modified, to form modified nucleotides.

Alternating as described herein means to occur one after another in a regular way. In other words, alternating means to occur in turn repeatedly. For example if one nucleotide is modified, the next contiguous nucleotide is not modified and the following contiguous nucleotide is modified and so on. One nucleotide may be modified with a first modification, the next contiguous nucleotide may be modified with a second modification and the following contiguous nucleotide is modified with the first modification and so on, where the first and second modifications are different.

One or more of the odd numbered nucleotides of the first strand of the nucleic acid of the invention may be modified wherein the first strand is numbered 5' to 3'. The term "odd numbered" as described herein means a number not divisible by two. Examples of odd numbers are 1, 3, 5, 7, 9, 11 and so on. One or more of the even numbered nucleotides of the first strand of the nucleic acid of the invention may be modified, wherein the first strand is numbered 5' to 3'. The term "even numbered" as described herein means a number which is evenly divisible by two. Examples of even numbers are 2, 4, 6, 8, 10, 12, 14 and so on. One or more of the odd numbered nucleotides of the second strand of the nucleic acid of the invention may be modified wherein the second strand is numbered 3' to 5'. One or more of the even numbered nucleotides of the second strand of the nucleic acid of the invention may be modified, wherein the second strand is numbered 3' to 5'.

One or more nucleotides on the first and/or second strand may be modified, to form modified nucleotides. One or more of the odd numbered nucleotides of the first strand may be modified. One or more of the even numbered nucleotides of the first strand may be modified by at least a second modification, wherein the at least second modification is different from the modification on the one or more add nucleotides. At least one of the one or more modified even numbered nucleotides may be adjacent to at least one of the one or more modified odd numbered nucleotides.

A plurality of odd numbered nucleotides in the first strand may be modified in the nucleic acid of the invention. A plurality of even numbered nucleotides in the first strand may be modified by a second modification. The first strand may comprise adjacent nucleotides that are modified by a common modification. The first strand may also comprise adjacent nucleotides that are modified by a second different modification.

One or more of the odd numbered nucleotides of the second strand may be modified by a modification that is different to the modification of the odd numbered nucleotides on the first strand and/or one or more of the even numbered nucleotides of the second strand may be by the same modification of the odd numbered nucleotides of the first strand. At least one of the one or more modified even numbered nucleotides of the second strand may be adjacent to the one or more modified odd numbered nucleotides. A plurality of odd numbered nucleotides of the second strand may be modified by a common modification and/or a plurality of even numbered nucleotides may be modified by the same modification that is present on the first stand odd numbered nucleotides. A plurality of odd numbered nucleotides on the second strand may be modified by a second modification, wherein the second modification is different from the modification of the first strand odd numbered nucleotides.

The second strand may comprise adjacent nucleotides that are modified by a common modification, which may be a second modification that is different from the modification of the odd numbered nucleotides of the first strand.

In the nucleic acid of the invention, each of the odd numbered nucleotides in the first strand and each of the even numbered nucleotides in the second strand may be modified with a common modification and, each of the even numbered nucleotides may be modified in the first strand with a second modification and each of the odd numbered nucleotides may be modified in the second strand with the second modification.

The nucleic acid of the invention may have the modified nucleotides of the first strand shifted by at least one nucleotide relative to the unmodified or differently modified nucleotides of the second strand.

One or more or each of the odd numbered nucleotides may be modified in the first strand and one or more or each of the even numbered nucleotides may be modified in the second strand. One or more or each of the alternating nucleotides on either or both strands may be modified by a second modification. One or more or each of the even numbered nucleotides may be modified in the first strand and one or more or each of the even numbered nucleotides may be modified in the second strand. One or more or each of the alternating nucleotides on either or both strands may be modified by a second modification. One or more or each of the odd numbered nucleotides may be modified in the first strand and one or more of the odd numbered nucleotides may be modified in the second strand by a common modification. One or more or each of the alternating nucleotides on either or both strands may be modified by a second modification. One or more or each of the even numbered nucleotides may be modified in the first strand and one or more or each of the odd numbered nucleotides may be modified in the second strand by a common modification. One or more or each of the alternating nucleotides on either or both strands may be modified by a second modification.

The nucleic acid of the invention may comprise at least two regions of alternating modifications in one or both of the strands. These alternating regions can comprise up to about 12 nucleotides but preferably comprise from about 3 to about 10 nucleotides. The regions of alternating nucleotides may be located at the termini of one or both strands of the nucleic acid of the invention. The nucleic acid may comprise from 4 to about 10 nucleotides of alternating nucleotides at each termini (3' and 5') and these regions may be separated by from about 5 to about 12 contiguous unmodified or differently or commonly modified nucleotides.

The odd numbered nucleotides of the first strand may be modified and the even numbered nucleotides may be modified with a second modification. The second strand may comprise adjacent nucleotides that are modified with a common modification, which may be the same as the modification of the odd numbered nucleotides of the first strand. One or more nucleotides of second strand may also be modified with the second modification. One or more nucleotides with the second modification may be adjacent to each other and to nucleotides having a modification that is the same as the modification of the odd numbered nucleotides of the first strand.

The nucleic acid of the invention may comprise a first strand comprising adjacent nucleotides that are modified with a common modification. One or more of such nucleotides may be adjacent to one or more nucleotides which may be modified with a second modification. One or more nucleotides with the second modification may be adjacent. The second strand may comprise adjacent nucleotides that are modified with a common modification, which may be the same as one of the modifications of one or more nucleotides of the first strand. One or more nucleotides of second strand may also be modified with the second modification. One or more nucleotides with the second modification may be adjacent.

The nucleotides numbered (from 5' to 3' on the first strand and 3' and 5' on the second strand) 1, 3, 5, 7, 9, 11, 13, 15, 17, 19, 21, 23 and 25 may be modified by a modification on the first strand. The nucleotides numbered 2, 4, 6, 8, 10, 12, 14, 16, 18, 20, 22 and 24 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

The nucleotides numbered 2, 4, 6, 8, 10, 12, 14, 16, 18, 20, 22 and 24 may be modified by a modification on the first strand. The nucleotides numbered 1, 3, 5, 7, 9, 11, 13, 15, 17, 19, 21, 23 may be modified by a second modification on the first strand. The nucleotides numbered 1, 3, 5, 7, 9, 11, 13, 15, 17, 19, 21, 23 may be modified by a modification on the second strand. The nucleotides numbered 2, 4, 6, 8, 10, 12, 14, 16, 18, 20, 22 and 24 may be modified by a second modification on the second strand.

Clearly, if the first and/or the second strand are shorter than 25 nucleotides in length, such as 19 nucleotides in length, there are no nucleotides numbered 20, 21, 22, 23, 24 and 25 to be modified. The skilled person understands the description above to apply to shorter strands, accordingly.

One or more modified nucleotides on the first strand may be paired with modified nucleotides on the second strand having a common modification. One or more modified nucleotides on the first strand may be paired with modified nucleotides on the second strand having a different modification. One or more modified nucleotides on the first strand may be paired with unmodified nucleotides on the second strand. One or more modified nucleotides on the second strand may be paired with unmodified nucleotides on the first strand. In other words, the alternating nucleotides can be aligned on the two strands such as, for example, all the modifications in the alternating regions of the second strand are paired with identical modifications in the first strand or alternatively the modifications can be offset by one nucleotide with the common modifications in the alternating regions of one strand pairing with dissimilar modifications (i.e. a second or further modification) in the other strand. Another option is to have dissimilar modifications in each of the strands.

The modifications on the first strand may be shifted by one nucleotide relative to the modified nucleotides on the second strand, such that common modified nucleotides are not paired with each other.

In this embodiment, the nucleotides at positions 2 and 14 from the 5' end of the first strand may be modified.

In one aspect of this embodiment, the nucleotides at positions 2 and 14 from the 5' end of the first strand preferably are not modified with a 2'-OMe modification, and the nucleotide on the second strand which corresponds to position 13 of the first strand preferably is not modified with a 2'-OMe modification.

In another aspect of this embodiment, the nucleotides at positions 2 and 14 from the 5' end of the first strand preferably are not modified with a 2'-OMe modification, and the nucleotide on the second strand which corresponds to position 11 of the first strand preferably is not modified with a 2'-OMe modification.

In a further aspect of this embodiment, the nucleotides at positions 2 and 14 from the 5' end of the first strand preferably are not modified with a 2'-OMe modification, and the nucleotides on the second strand which corresponds to position 11 and 13 of the first strand preferably are not modified with a 2'-OMe modification.

In one aspect of this embodiment, the nucleotides on the second strand corresponding to positions 11 and/or 13 from the 5' end of the first strand may be modified.

In a further aspect of this embodiment, the nucleotides at positions 2 and 14 from the 5' end of the first strand preferably are not modified with a 2'-OMe modification, and the nucleotides on the second strand which correspond to position 11, or 13, or 11 and 13, or 11-13 of the first strand preferably are modified with a 2' fluoro modification.

In a further aspect of his embodiment, the nucleotides at positions 2 and 14 from the 5' end of the first strand preferably are modified with a 2' fluoro modification, and the nucleotides on the second strand which correspond to position 11, or 13, or 11 and 13, or 11-13 of the first strand preferably are not modified with a 2'-OMe modification.

In a further aspect of this embodiment, the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

In the nucleic acid or conjugate of the invention, greater than 50% of the nucleotides of the first and/or second strand may comprise a 2'-OMe modification, such as greater than 55%, 60%, 65%, 70%, 75%, 80%, or 85%, or more, of the first and/or second strand comprise a 2'-OMe modification, preferably measured as a percentage of the total nucleotides of both the first and second strands.

The nucleic acid or conjugate of the invention may comprise no more than 20%, (such as no more than 15% or no more than 10%) of 2' fluoro modifications on the first and/or second strand, as a percentage of the total nucleotides of both strands.

In one aspect of the nucleic acid, the nucleotide/nucleotides of the second strand in a position corresponding to nucleotide 11 or nucleotide 13 or nucleotides 11 and 13 or nucleotides 11-13 of the first strand is/are modified by a fourth modification. Preferably, all the nucleotides of the second strand other than the nucleotide/nucleotides in a position corresponding to nucleotide 11 or nucleotide 13 or nucleotides 11 and 13 or nucleotides 11-13 of the first strand is/are modified by a third modification. Preferably nucleotides 2 and 14 or all the even numbered nucleotides of the first strand are modified with a first modification in the same nucleic acid. In addition, or alternatively, the odd-numbered nucleotides of the first strand are modified with a second modification. The fourth modification is preferably different from the second modification and preferably different from the third modification and the fourth modification is preferably the same as the first modification. The second and third modification are preferably the same. The first and the fourth modification are preferably a 2'-OMe modification and the second and third modification are preferably a 2'-F modification. The nucleotides on the first strand are numbered consecutively starting with nucleotide number 1 at the 5' end of the first strand.

In one aspect of the nucleic acid, all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein the first and fourth modification are 2'-F and the second and third modification are 2'-OMe.

In one aspect of the nucleic acid, all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein the first and fourth modification are 2'-F and the second and third modification are 2'-OMe. Preferably in this aspect, the 3' terminal nucleotide of the second strand is an inverted RNA nucleotide (ie the nucleotide is linked to the 3' end of the strand through its 3' carbon, rather than through its 5' carbon as would normally be the case). When the 3' terminal nucleotide of the second strand is an inverted RNA nucleotide, the inverted RNA nucleotide is preferably an unmodified nucleotide in the sense that it does not comprise any modifications compared to the natural nucleotide counterpart. Specifically, the inverted RNA nucleotide is preferably a 2'-OH nucleotide.

In one aspect, the nucleic acid:

(i) has a terminal 5' (E)-vinylphosphonate nucleotide at the 5' end of the first strand;

(ii) has a phosphorothioate linkage between the terminal three 3' nucleotides on the first and second strand and between the terminal three 5' nucleotides on the second strand;

(iii) all remaining linkages between nucleotides of the first and/or of the second strand are phosphodiester linkages; and (iv) all the even-numbered nucleotides of the first strand are modified by a first modification, all the odd-numbered nucleotides of the first strand are modified by a second modification, all the nucleotides of the second strand in a position corresponding to an even-numbered nucleotide of the first strand are modified by a third modification, all the nucleotides of the second strand in a position corresponding to an odd-numbered nucleotide of the first strand are modified by a fourth modification, wherein preferably the first and fourth modification are 2'-F and the second and third modification are 2'-OMe.

In one aspect, the nucleic acid:

(i) has a terminal 5' (E)-vinylphosphonate nucleotide at the 5' end of the first strand;

(ii) has a phosphorothioate linkage between the terminal three 3' nucleotides on the first and second strand and between the terminal three 5' nucleotides on the second strand;

(iii) all remaining linkages between nucleotides of the first and/or of the second strand are phosphodiester linkages; and (iv) all the even-numbered nucleotides of the first strand are modified by a first modification, all the odd-numbered nucleotides of the first strand are modified by a second modification, all the nucleotides of the second strand in positions corresponding to nucleotides 11-13 of the first strand are modified by a fourth modification, all the nucleotides of the second strand other than the nucleotides corresponding to nucleotides 11-13 of the first strand are modified by a third modification, wherein preferably the first and fourth modification are 2'-F and the second and third modification are 2'-OMe.

Terminal Modifications

The 3' and 5' ends of an oligonucleotide can be modified. Such modifications can be at the 3' end or the 5' end or both ends of the molecule. They can include modification or replacement of an entire terminal phosphate or of one or more of the atoms of the phosphate group. For example, the 3' and 5' ends of an oligonucleotide can be conjugated to other functional molecular entities such as labelling moieties, e.g., fluorophores (e.g., pyrene, TAMRA, fluorescein, Cy3 or Cy5 dyes) or protecting groups (based e.g., on sulfur, silicon, boron or ester). The functional molecular entities can be attached to the sugar through a phosphate group and/or a linker. The terminal atom of the linker can connect to or replace the linking atom of the phosphate group or the C-3' or C-5'O, N, S or C group of the sugar. Alternatively, the linker can connect to or replace the terminal atom of a nucleotide surrogate (e.g., PNAs). These spacers or linkers can include e.g., —$(CH_2)_n$—, —$(CH_2)_n$N—, —$(CH_2)_n$O—, —$(CH_2)_s$S—, —$(CH_2CH_2O)_nCH_2CH_2$— (e.g., n=3 or 6), abasic sugars, amide, carboxy, amine, oxyamine, oxyimine, thioether, disulfide, thiourea, sulfonamide, or morpholino, or biotin and fluorescein reagents. The 3' end can be an —OH group.

Other examples of terminal modifications include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases, EDTA, lipophilic carriers (e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles).

Alternative or additional terminal modifications can be added for a number of reasons, including to modulate activity or to modulate resistance to degradation. Terminal modifications useful for modulating activity include modification of the 5' end with phosphate or phosphate analogues. Nucleic acids of the invention, on the first or second strand, may be 5' phosphorylated or include a phosphoryl analogue at the 5' prime terminus. 5'-phosphate modifications include those which are compatible with RISC mediated gene silencing. Suitable modifications include: 5'-monophosphate ($(HO)_2$(O)P—O-5'); 5'-diphosphate ($(HO)_2$(O)P—O—P(HO)(O)—O-5'); 5'-triphosphate ($(HO)_2$(O)P—θ-(HO)(O)P—O—P(HO)(O)—O-5'); 5'-guanosine cap (7-methylated or non-methylated) (7m-G-O-5'-(HO)(O)P—O—(HO)(O)P—O—P(HO)(O)—O-5'); 5'-adenosine cap (Appp), and any modified or unmodified nucleotide cap structure (N—O-5'-(HO)(O)P—O—(HO)(O)P—O—P(HO)(O)—O-5'); 5'-monothiophosphate (phosphorothioate; (HO)2(S)P—O-5'); 5'-monodithiophosphate (phosphorodithioate; (HO)(HS)(S)P—O-5'), 5'-phosphorothiolate ($(HO)_2$(O)P—S-5'); any additional combination of oxygen/sulfur replaced monophosphate, diphosphate and triphosphates (e.g., 5'-alpha-thiotriphosphate, 5'-gamma-thiotriphosphate, etc.), 5'-phosphoramidates ($(HO)_2$(O)P—NH-5', (HO)($NH_2$)(O)P—O-5'), 5'-alkylphosphonates (R=alkyl=methyl, ethyl, isopropyl, propyl, etc., e.g., RP(OH)(O)—O-5'-, $(OH)_2$(O)P-5'-$CH_2$—), 5'-alkyletherphosphonates, 5'-vinylphosphonate (R=alkylether=methoxymethyl ($MeOCH_2$—), ethoxymethyl, etc., e.g., RP(OH)(O)—O-5'-).

The nucleic acid of the present invention comprises at least one terminal 5' (E)-vinylphosphonate nucleotide at the 5' end of the first strand.

Terminal modifications can also be useful for monitoring distribution, and in such cases the groups to be added may include fluorophores, e.g., fluorescein or an Alexa dye. Terminal modifications can also be useful for enhancing uptake, useful modifications for this include cholesterol. Terminal modifications can also be useful for cross-linking an RNA agent to another moiety.

Adenine, guanine, cytosine and uracil are the most common bases found in RNA. These bases can be modified or replaced to provide RNAs having improved properties. E.g., nuclease resistant oligoribonucleotides can be prepared with these bases or with synthetic and natural nucleobases (e.g., inosine, thymine, xanthine, hypoxanthine, nubularine, isoguanisine, or tubercidine) and any one of the above modifications. Alternatively, substituted or modified analogues of any of the above bases and "universal bases" can be employed. Examples include 2-aminoadenine, 6-methyl and other alkyl derivatives of adenine and guanine, 2-propyl and other alkyl derivatives of adenine and guanine, 5-halouracil and cytosine, 5-propynyl uracil and cytosine, 6-azo uracil, cytosine and thymine, 5-uracil (pseudouracil), 4-thiouracil, 5-halouracil, 5-(2-aminopropyl)uracil, 5-amino allyl uracil, 8-halo, amino, thiol, thioalkyl, hydroxyl and other 8-substituted adenines and guanines, 5-trifluoromethyl and other 5-substituted uracils and cytosines, 7-methylguanine, 5-substituted pyrimidines, 6-azapyrimidines and N-2, N-6 and O-6 substituted purines, including 2-aminopropyladenine, 5-propynyluracil and 5-propynylcytosine, dihydrouracil, 3-deaza-5-azacytosine, 2-aminopurine, 5-alkyluracil, 7-alkylguanine, 5-alkyl cytosine, 7-deazaadenine, N6,N6-dimethyladenine, 2,6-diaminopurine, 5-amino-allyl-uracil, N3-methyluracil, substituted 1,2,4-triazoles, 2-pyridinone, 5-nitroindole, 3-nitropyrrole, 5-methoxyuracil, uracil-5-oxyacetic acid, 5-methoxycarbonylmethyluracil, 5-methyl-2-thiouracil, 5-methoxycarbonylmethyl-2-thiouracil, 5-methylaminomethyl-2-thiouracil, 3-(3-amino-3-carboxypropyl)uracil, 3-methylcytosine, 5-methylcytosine, N<4>-acetyl cytosine, 2-thiocytosine, N6-methyladenine, N6-isopentyladenine, 2-methylthio-N6-isopentenyladenine, N-methylguanines, or O-alkylated bases.

As used herein, the terms "non-pairing nucleotide analogue" means a nucleotide analogue which includes a non-base pairing moiety including but not limited to: 6 des amino adenosine (Nebularine), 4-Me-indole, 3-nitropyrrole, 5-nitroindole, Ds, Pa, N3-Me ribo U, N3-Me riboT, N3-Me dC, N3-Me-dT, N1-Me-dG, N1-Me-dA, N3-ethyl-dC, N3-Me dC. In some embodiments the non-base pairing nucleotide analogue is a ribonucleotide. In other embodiments it is a deoxyribonucleotide.

As used herein, the term, "terminal functional group" includes without limitation a halogen, alcohol, amine, carboxylic, ester, amide, aldehyde, ketone, ether groups.

Certain moieties may be linked to the 5' terminus of the first strand or the second strand and includes abasic ribose moiety, abasic deoxyribose moiety, modifications abasic ribose and abasic deoxyribose moieties including 2'O alkyl modifications; inverted abasic ribose and abasic deoxyribose moieties and modifications thereof, C6-imino-Pi; a mirror nucleotide including L-DNA and L-RNA; 5'-OMe nucleotide; and nucleotide analogues including 4',5'-methylene nucleotide; 1-(3-D-erythrofuranosyl)nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 12-aminododecyl phosphate; hydroxypropyl phosphate; 1,5-anhydrohexitol nucleotide; alpha-nucleotide; threo-pentofuranosyl nucleotide; acyclic 3',4'-seco nucleotide; 3,4-dihydroxybutyl nucleotide; 3,5-dihydroxypentyl nucleotide, 5'-5'-inverted abasic moiety; 1,4-butanediol phosphate; 5'-amino; and bridging or non-bridging methylphosphonate and 5'-mercapto moieties.

Other Modifications

In addition to the 5' (E)-vinylphosphonate, modifications at the 2'—OH group of the ribose sugar and other terminal modifications described above, the nucleic acid of the invention may comprise further modifications selected from the group consisting of 3-terminal deoxy-thymine, a morpholino modification, a phosphoramidate modification, 5'-phosphorothioate group modification, a 5' phosphate or 5' phosphate mimic modification and a cholesteryl derivative or a dodecanoic acid bisdecylamide group modification and/or the modified nucleotide may be any one of a locked nucleotide, an abasic nucleotide or a non-natural base comprising nucleotide.

The nucleic acid may comprise a nucleotide comprising a modified nucleotide, wherein the base is selected from 2-aminoadenosine, 2,6-diaminopurine, inosine, pyridin-4-one, pyridin-2-one, phenyl, pseudouracil, 2, 4, 6-trimethoxy benzene, 3-methyl uracil, dihydrouridine, naphthyl, aminophenyl, 5-alkylcytidine (e.g., 5-methylcytidine), 5-alkyluridine (e.g., ribothymidine), 5-halouridine (e.g., 5-bromouridine), 6-azapyrimidine, 6-alkylpyrimidine (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid and 2-thiocytidine.

Examples of moieties which can replace the phosphate group include siloxane, carbonate, carboxymethyl, carbamate, amide, thioether, ethylene oxide linker, sulfonate, sulfonamide, thioformacetal, formacetal, oxime, methyleneimino, methylenemethylimino, methylenehydrazo, methylenedimethylhydrazo and methyleneoxymethylimino. In certain embodiments, replacements may include the methylenecarbonylamino and methylenemethylimino-groups.

The phosphate linker and ribose sugar may be replaced by nuclease resistant nucleotides.

Examples include the morpholino, cyclobutyl, pyrrolidine and peptide nucleic acid (PNA) nucleoside surrogates. In certain embodiments, PNA surrogates may be used.

The sugar group can also contain one or more carbons that possess the opposite stereochemical configuration than that of the corresponding carbon in ribose. Thus, a modified nucleotide may contain a sugar such as arabinose.

Modified nucleotides can also include "abasic" sugars, which lack a nucleobase at C-1'. These abasic sugars can further contain modifications at one or more of the constituent sugar atoms.

The nucleic acid of the present invention may comprise an abasic nucleotide. The term "abasic" as used herein, refers to moieties lacking a base or having other chemical groups in place of a base at the 1' position, for example a 3',3'-linked or 5',5'-linked deoxyabasic ribose derivative.

Further modifications as described herein may be present on the first and/or second strand.

Some representative modified nucleic acid sequences of the present invention are shown in the examples. These examples are meant to be representative and not limiting.

Ligands

The nucleic acid of the invention may be conjugated to a targeting ligand, to form a conjugate.

The present invention further provides a conjugate for inhibiting expression of a target gene in a cell, said conjugate comprising a nucleic acid portion and ligand portion, said nucleic acid portion comprising a nucleic acid as defined anywhere herein.

In the conjugate of the invention, the second strand of the nucleic acid may be conjugated to the ligand portion.

In the conjugate of the invention, the ligand portion may comprise one or more GalNAc ligands and derivatives thereof, such as comprising a GalNAc moiety or several GalNAc moieties at the 5' end of the second strand of the nucleic acid.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. The endosomolytic component may contain a chemical group which undergoes a change in charge or protonation in response to a change in pH. The endosomolytic component may be linear or branched.

Ligands can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics. Ligands can include a naturally occurring substance, such as a protein, carbohydrate, or lipid. The ligand may be a recombinant or synthetic molecule.

Ligands can also include targeting groups, e.g. a cell or tissue targeting agent. The targeting ligand may be a lectin, glycoprotein, lipid or protein.

Other examples of ligands include dyes, intercalating agents, cross-linkers, porphyrins, polycyclic aromatic hydrocarbons, artificial endonucleases or a chelator, lipophilic molecules, alkylating agents, phosphate, amino, mercapto, PEG, MPEG, alkyl, substituted alkyl, radiolabelled markers, enzymes, haptens, transport/absorption facilitators, synthetic ribonucelases, or imidazole clusters.

Ligands can be proteins, e.g. glycoproteins or peptides. Ligands may also be hormones or hormone receptors. They may also include non-peptidic species, such as lipids, lectins, carbohydrates, vitamins, or cofactors.

The ligand may be a substance such as a drug which can increase the uptake of the nucleic acid into a cell, for example, by disrupting the cell's cytoskeleton.

The ligand may increase uptake of the nucleic acid into the cell by activating an inflammatory response. Such ligands include tumour necrosis factor alpha (TNF-alpha), interleukin-1 beta, or gamma interferon.

The ligand may be a lipid or lipid-based molecule. The lipid or lipid-based molecule preferably binds a serum protein. Preferably, the lipid-based ligand binds human serum albumin (HSA). A lipid or lipid-based molecule can increase resistance to degradation of the conjugate, increase targeting or transport into target cell, and/or can adjust binding to a serum protein. A lipid-based ligand can be used to modulate binding of the conjugate to a target tissue.

The ligand may be a steroid. Preferably, the ligand is cholesterol or a cholesterol derivative.

The ligand may be a moiety e.g. a vitamin, which is taken up by a target cell. Exemplary vitamins include vitamin A, E, K, and the B vitamins. Vitamins may be taken up by a proliferating cell, which may be useful for delivering the nucleic acid to cells such as malignant or non-malignant tumour cells.

The ligand may be a cell-permeation agent, such as a helical cell-permeation agent.

Preferably such an agent is amphipathic.

The ligand may be a peptide or peptidomimetic. A peptidomimetic is a molecule capable of folding into a defined three-dimensional structure similar to a natural peptide. The peptide or peptidomimetic ligand may include naturally occurring or modified peptides, or both. A peptide or peptidomimetic can be a cell permeation peptide, cationic peptide, amphipathic peptide, or hydrophobic peptide. The peptide moiety can be a dendrimer peptide, constrained peptide, or crosslinked peptide. The peptide moiety can include a hydrophobic membrane translocation sequence. The peptide moiety can be a peptide capable of carrying large polar molecules such as peptides, oligonucleotides, and proteins across cell membranes, e.g. sequences from the HIV Tat protein (GRKKRRQRRRPPQ) and the *Drosophila* Antennapedia protein (RQIKIWFQNRRMKWKK). Preferably the peptide or peptidomimetic is a cell targeting peptide, e.g. arginine-glycine-aspartic acid (RGD)-peptide.

The ligand may be a cell permeation peptide that is capable of permeating, for example, a microbial cell or a mammalian cell.

The ligand may be a pharmacokinetic modulator. The pharmacokinetic modulator may be lipophiles, bile acids, steroids, phospholipid analogues, peptides, protein binding agents, PEG, vitamins, etc.

When two or more ligands are present, the ligands can all have the same properties, all have different properties, or some ligands have the same properties while others have different properties. For example, a ligand can have targeting properties, have endosomolytic activity or have PK modulating properties. In a preferred embodiment, all the ligands have different properties.

Ligands can be coupled to the nucleic acid at the 3' end, 5' end, and/or at an internal position. Preferably the ligand is coupled to the nucleic acid via an intervening tether or linker.

In some embodiments the nucleic acid is a double-stranded nucleic acid. In a double-stranded nucleic acid the ligand may be attached to one or both strands. In some embodiments, a double-stranded nucleic acid contains a ligand conjugated to the sense strand. In other embodiments, a double-stranded nucleic acid contains a ligand conjugated to the antisense strand.

Ligands can be conjugated to nucleobases, sugar moieties, or internucleosidic linkages of nucleic acid molecules. Conjugation to purine nucleobases or derivatives thereof can occur at any position including endocyclic and exocyclic atoms. Conjugation to pyrimidine nucleotides or derivatives thereof can also occur at any position. Conjugation to sugar moieties of nucleosides can occur at any carbon atom. Conjugation to internucleosidic linkages may occur at the phosphorus atom of a phosphorus-containing linkage or at an oxygen, nitrogen, or sulphur atom bonded to the phosphorus atom. For amine- or amide-containing internucleosidic linkages, conjugation may occur at the nitrogen atom of the amine or amide or to an adjacent carbon atom.

The ligand is typically a carbohydrate, e.g. a monosaccharide, disaccharide, trisaccharide, tetrasaccharide or polysaccharide. The ligand may be conjugated to the nucleic acid by a linker moiety. The linker moiety may be a monovalent, bivalent, or trivalent branched linker.

Means for efficient delivery of oligonucleotides, in particular double stranded nucleic acids of the invention, to cells in vivo is important and requires specific targeting and substantial protection from the extracellular environment, particularly serum proteins. One method of achieving specific targeting is to conjugate a targeting moiety or ligand to the nucleic acid.

The targeting moiety helps in targeting the nucleic acid to the required target site and there is a need to conjugate appropriate targeting moieties for the desired receptor sites for the conjugated molecules to be taken up by the cells such as by endocytosis. The targeting moiety or ligand can be any moiety or ligand that is capable of targeting a specific receptor.

For example, the Asialoglycoprotein receptor (ASGP-R) is a high capacity receptor, which is highly abundant on hepatocytes. One of the first disclosures of triantennary cluster glycosides was in U.S. Pat. No. 5,885,968. Conjugates having three GalNAc ligands and comprising phosphate groups are known and are described in Dubber et al. (2003). The ASGP-R shows a 50-fold higher affinity for N-Acetyl-D-Galactosylamine (GalNAc) than D-Gal.

Hepatocytes expressing the lectin (asialoglycoprotein receptor; ASGPR), which recognizes specifically terminal β-galactosyl subunits of glycosylated proteins or other oligosaccharides (P. H. Weigel et. al., 2002,) can be used for targeting a drug to the liver by covalent coupling of galactose or galactosamine to the drug substance (S. shibashi, et. al. 1994). Furthermore the binding affinity can be significantly increased by the multi-valency effect, which is achieved by the repetition of the targeting unit (E. A. L. Biessen et. al., 1995).

The ASGPR is a mediator for an active endosomal transport of terminal β-galactosyl containing glycoproteins, thus ASGPR is highly suitable for targeted delivery of drug candidates like nucleic acid, which have to be delivered into a cell (Akinc et al.).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

The saccharide may be selected from N-acetyl galactosamine, mannose, galactose, glucose, glucosamine and fucose. The saccharide may be N-acetyl galactosamine (GalNAc).

A ligand for use in the present invention may therefore comprise (i) one or more N-acetyl galactosamine (GalNAc) moieties and derivatives thereof, and (ii) alinker, wherein the linker conjugates the GalNAc moieties to a nucleic acid or sequence as defined in any preceding aspects. The linker may be monovalent or a bivalent or trivalent or tetravalent branched structure. The nucleotides may be modified as defined herein.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. Both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

The ligand may comprise GalNAc.

The ligand may comprise a compound of formula (II):

$$[S—X^1—P—X^2]_3\text{-}A\text{-}X^3— \quad (II)$$

wherein:

S represents a saccharide, preferably wherein the saccharide is N-acetyl galactosamine;

$X^1$ represents $C_3$-$C_6$ alkylene or $(—CH_2—CH_2—O)_m(—CH_2)_2—$ wherein m is 1, 2, or 3;

P is a phosphate or modified phosphate, preferably a thiophosphate;

$X^2$ is alkylene or an alkylene ether of the formula $(—CH_2)_n—O—CH_2—$ where n=1-6;

A is a branching unit;

$X^3$ represents a bridging unit;

wherein a nucleic acid according to the present invention is conjugated to $X^3$ via a phosphate or modified phosphate, preferably a thiophosphate, preferably at the 5' end of the sense strand.

In formula (II), the branching unit "A" preferably branches into three in order to accommodate three saccharide ligands. The branching unit is covalently attached to the ligands and the nucleic acid. The branching unit may comprise a branched aliphatic group comprising groups selected from alkyl, amide, disulphide, polyethylene glycol, ether, thioether and hydroxyamino groups. The branching unit may comprise groups selected from alkyl and ether groups.

The branching unit A may have a structure selected from:

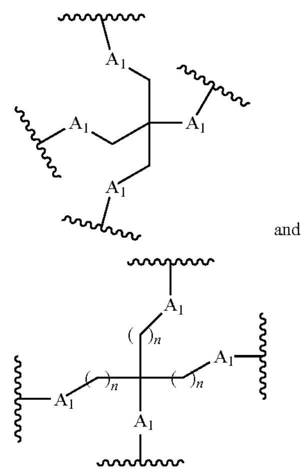

wherein each $A_1$ independently represents O, S, C═O or NH; and each n independently represents an integer from 1 to 20.

The branching unit may have a structure selected from:

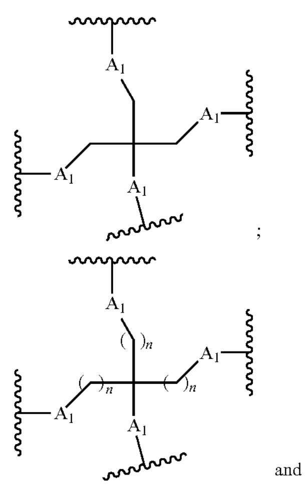

-continued

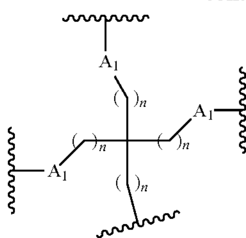

wherein each $A_1$ independently represents O, S, C═O or NH; and each n independently represents an integer from 1 to 20.

The branching unit may have a structure selected from:

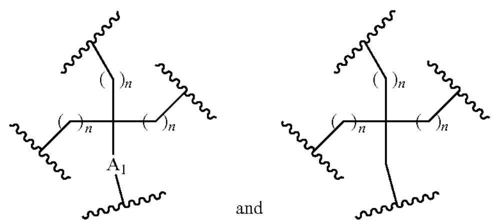

wherein $A_1$ is O, S, C═O or NH; and each n independently represents an integer from 1 to 20.

The branching unit may have the structure:

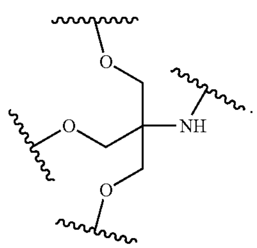 [SMILES: *NC(CO*)(CO*)CO*]

The branching unit may have the structure:

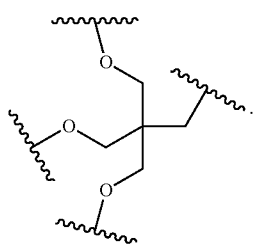 [SMILES: *CC(CO*)(CO*)CO*]

The branching unit may have the structure:

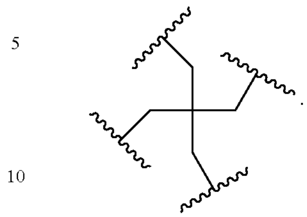

Optionally, the branching unit consists of only a carbon atom.

The "$X^3$" portion is a bridging unit. The bridging unit is linear and is covalently bound to the branching unit and the nucleic acid.

$X^3$ may be selected from —$C_1$-$C_{20}$ alkylene-, —$C_2$-$C_{20}$ alkenylene-, an alkylene ether of formula —($C_1$-$C_{20}$ alkylene)-O—($C_1$-$C_{20}$ alkylene)-, —C(O)—$C_1$-$C_{20}$ alkylene-, —$C_0$-$C_4$ alkylene(Cy)$C_0$-$C_4$ alkylene- wherein Cy represents a substituted or unsubstituted 5 or 6 membered cycloalkylene, arylene, heterocyclylene or heteroarylene ring, —$C_1$-$C_4$ alkylene-NHC(O)—$C_1$-$C_4$alkylene-, —$C_1$-$C_4$ alkylene-C(O)NH—$C_1$-$C_4$ alkylene-, —$C_1$-$C_4$ alkylene-SC(O)—$C_1$-$C_4$ alkylene-, —$C_1$-$C_4$ alkylene-C(O)S—$C_1$-$C_4$ alkylene-, —$C_1$-$C_4$ alkylene-OC(O)—$C_1$-$C_4$ alkylene-, —$C_1$-$C_4$ alkylene-C(O)O—$C_1$-$C_4$ alkylene-, and —$C_1$-$C_6$ alkylene-S—S—$C_1$-$C_6$ alkylene-.

$X^3$ may be an alkylene ether of formula —($C_1$-$C_{20}$ alkylene)-O—($C_2$-$C_{20}$ alkylene)-. $X^3$ may be an alkylene ether of formula —($C_1$-$C_{20}$ alkylene)-O—($C_4$-$C_{20}$ alkylene)-, wherein said ($C_4$-$C_{20}$ alkylene) is linked to Z. $X^3$ may be selected from the group consisting of —$CH_2$—$C_3H_6$—, —$CH_2$—O—$C_4H_8$—, —$CH_2$—O—$C_6H_{12}$— and —$CH_2$—O—$C_8H_{16}$—, especially —$CH_2$—O—$C_4H_8$—, —$CH_2$—O—$C_6H_{12}$— and —$CH_2$—O—$C_8H_{16}$—, wherein in each case the —$CH_2$— group is linked to A.

The ligand may comprise a compound of formula (III):

$$[S—X^1—P—X^2]_{n3}\text{-}A\text{-}X^3— \quad \text{(III)}$$

wherein:

S represents a saccharide, preferably GalNAc;

$X^1$ represents $C_3$-$C_6$ alkylene or an ethylene glycol stem (—$CH_2$—$CH_2$—O)$_m$(—$CH_2$)$_2$— wherein m is 1, 2, or 3;

P is a phosphate or modified phosphate, preferably a thiophosphate;

$X^2$ is $C_1$-$C_6$ alkylene;

A is a branching unit selected from:

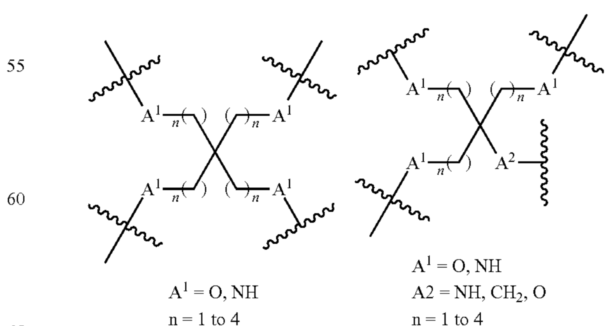

$X^3$ is a bridging unit;

wherein a nucleic acid according to the present invention is conjugated to $X^3$ via a phosphate or modified phosphate, preferably a thiophosphate.

Branching unit A may have the structure:

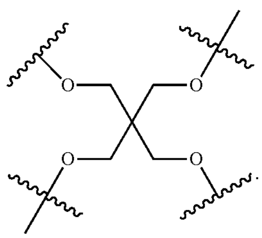 [SMILES: *OCC(CO*)(CO*)CO*]

Branching unit A may have the structure:

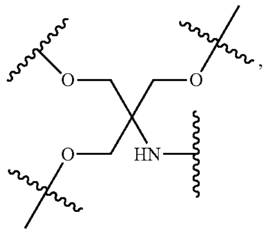

wherein $X^3$ is attached to the nitrogen atom.

$X^3$ may be $C_1$-$C_{20}$ alkylene. Preferably, $X^3$ is selected from the group consisting of —$C_3H_6$—, —$C_4H_8$—, —$C_6H_{12}$— and —$C_8H_{16}$—, especially —$C_4H_8$—, —$C_6H_{12}$— and —$C_8H_{16}$—.

The ligand may comprise a compound of formula (IV):

$$[S\text{—}X^1\text{—}P\text{—}X^2]_3\text{-}A\text{-}X^3 \quad \text{(IV)}$$

wherein:

S represents a saccharide, preferably GalNAc;

$X^1$ represents $C_3$-$C_6$ alkylene or an ethylene glycol stem (—$CH_2$—$CH_2$—O)$_m$(—$CH_2$)$_2$— wherein m is 1, 2, or 3;

P is a phosphate or modified phosphate, preferably a thiophosphate;

$X^2$ is an alkylene ether of formula —$C_3H_6$—O—$CH_2$—;

A is a branching unit;

$X^3$ is an alkylene ether of formula selected from the group consisting of —$CH_2$—O—$CH_2$—, —$CH_2$—O—$C_2H_4$—, —$CH_2$—O—$C_3H_6$—, —$CH_2$—O—$C_4H_8$—, —$CH_2$—O—$C_5H_{10}$—, —$CH_2$—O—$C_6H_{12}$—, —$CH_2$—O—$C_7H_{14}$—, and —$CH_2$—O—$C_8H_{16}$—, wherein in each case the —$CH_2$— group is linked to A, wherein a nucleic acid according to the present invention is conjugated to $X^3$ via a phosphate or modified phosphate, preferably a thiophosphate.

The branching unit may comprise carbon. Preferably, the branching unit is carbon.

$X^2$ represents an alkylene ether of formula —$C_3H_6$—O—$CH_2$—i.e. C alkoxy methylene, or —$CH_2CH_2CH_2OCH_2$—.

For any of the above aspects of the ligand, P represents a modified phosphate group. P can be represented by:

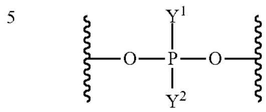

wherein $Y^1$ and $Y^2$ each independently represent =O, =S, —O—, —OH, —SH, —$BH_3$, —$OCH_2CO_2$, —$OCH_2CO_2$Rx, —$OCH_2C(S)OR^x$, and —$OR^x$, wherein $R^x$ represents $C_1$-$C_6$ alkyl and wherein indicates attachment to the remainder of the compound.

By modified phosphate It is meant a phosphate group wherein one or more of oxygens is replaced. Examples of modified phosphate groups include phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulphur. One, each or both non-linking oxygens in the phosphate group can be independently any one of S, Se, B, C, H, N, or OR (R is alkyl or aryl).

The phosphate linker can also be modified by replacement of a linking oxygen with nitrogen (bridged phosphoroamidates), sulfur (bridged phosphorothioates) and carbon (bridged methylenephosphonates). The replacement can occur at a terminal oxygen. Replacement of the non-linking oxygens with nitrogen is possible.

For example, $Y^1$ may represent —OH and $Y^2$ may represent =O or =S; or $Y^1$ may represent —O— and $Y^2$ may represent =O or =S;

$Y^1$ may represent =O and $Y^2$ may represent —$CH_3$, —SH, —$OR^x$, or —$BH_3$ $Y^1$ may represent =S and $Y^2$ may represent —$CH_3$, $OR^x$ or —SH.

It will be understood by the skilled person that in certain instances there will be delocalisation between $Y^1$ and $Y^2$.

Preferably, the modified phosphate group is a thiophosphate group. Thiophosphate groups include bithiophosphate (i.e. where $Y^1$ represents =S and $Y^2$ represents —S—) and monothiophosphate (i.e. where $Y^1$ represents —O— and $Y^2$ represents =S, or where $Y^1$ represents =O and $Y^2$ represents —S—). Preferably, P is a monothiophosphate. The inventors have found that conjugates having thiophosphate groups in replacement of phosphate groups have improved potency and duration of action in vivo.

P may also be an ethylphosphate (i.e. where $Y^1$ represents =O and $Y^2$ represents $OCH_2CH_3$).

The saccharide, which can also be referred to as the ligand, may be selected to have an affinity for at least one type of receptor on a target cell. In particular, the receptor is on the surface of a mammalian liver cell, for example, the hepatic asialoglycoprotein receptor (ASGP-R).

For any of the above aspects, the saccharide may be selected from N-acetyl with one or more of galactosamine, mannose, galactose, glucose, glucosamine and fructose.

Preferably, the saccharide is two molecules of N-acetyl galactosamine (GalNAc). The compounds of the invention may have 3 ligands which are each preferably N-acetyl galactosamine.

"GalNAc" refers to 2-(Acetylamino)-2-deoxy-D-galactopyranose, commonly referred to in the literature as N-acetyl galactosamine. Reference to "GalNAc" or "N-acetyl galactosamine" includes both the β-form: 2-(Acetylamino)-2-deoxy-β-D-galactopyranose and the α-form: 2-(Acetylamino)-2-deoxy-α-D-galactopyranose. In certain embodiments, both the β-form: 2-(Acetylamino)-2-deoxy-β-D-galactopyranose and α-form: 2-(Acetylamino)-2-deoxy-α-D-galactopyranose may be used interchangeably. Preferably, the compounds of the invention comprise the β-form, 2-(Acetylamino)-2-deoxy-β-D-galactopyranose.

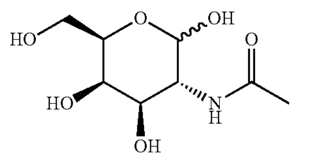

2-(Acetylamino)-2-deoxy-D-galactopyranose

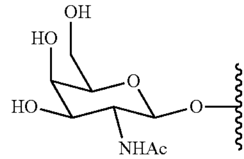

2-(Acetylamino)-2-deoxy-β-D-galactopyranose

-continued

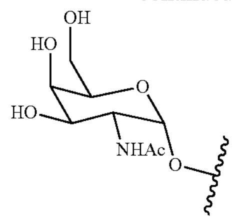

2-(Acetylamino)-2-deoxy-α-D-galactopyranose

For any of the above compounds of formula (IV), $X^1$ may be an ethylene glycol stem $(—CH_2—CH_2—O)_m(—CH_2)_2—$ wherein m is 1, 2, or 3. $X^1$ may be $(—CH_2—CH_2—O)(—CH_2)_2—$. $X^1$ may be $(—CH_2—CH_2—O)_2(—CH_2)_2—$. $X^1$ may be $(—CH_2—CH_2—O)_3(—CH_2)_2—$. Preferably, $X^1$ is $(—CH_2—CH_2—O)_2(—CH_2)_2—$. Alternatively, $X^1$ represents $C_3$-$C_6$ alkylene. $X^1$ may be propylene. $X^1$ may be butylene. $X^1$ may be pentylene. $X^1$ may be hexylene. Preferably the alkyl is a linear alkylene. In particular, $X^1$ may be butylene.

For compounds of formula (IV), $X^2$ represents an alkylene ether of formula $—C_3H_6—O—CH_2—$ i.e. $C_3$ alkoxy methylene, or $—CH_2CH_2CH_2OCH_2—$.

The present invention therefore additionally provides a conjugated nucleic acid having one of the following structures:

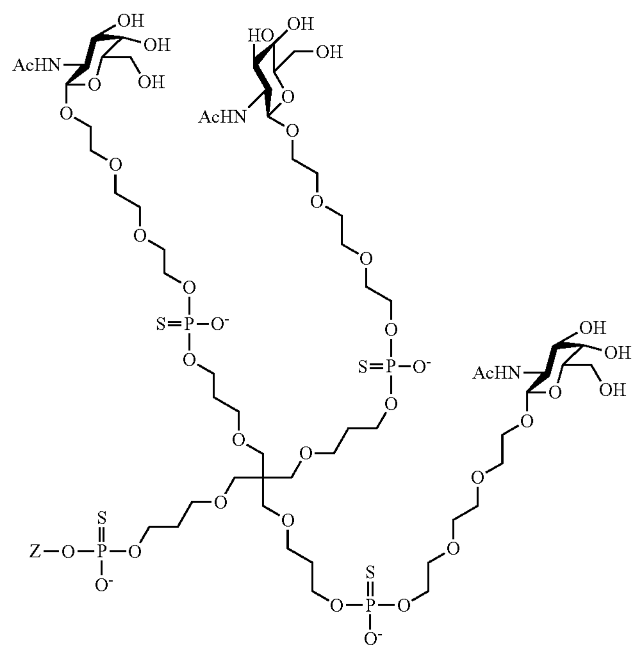

-continued
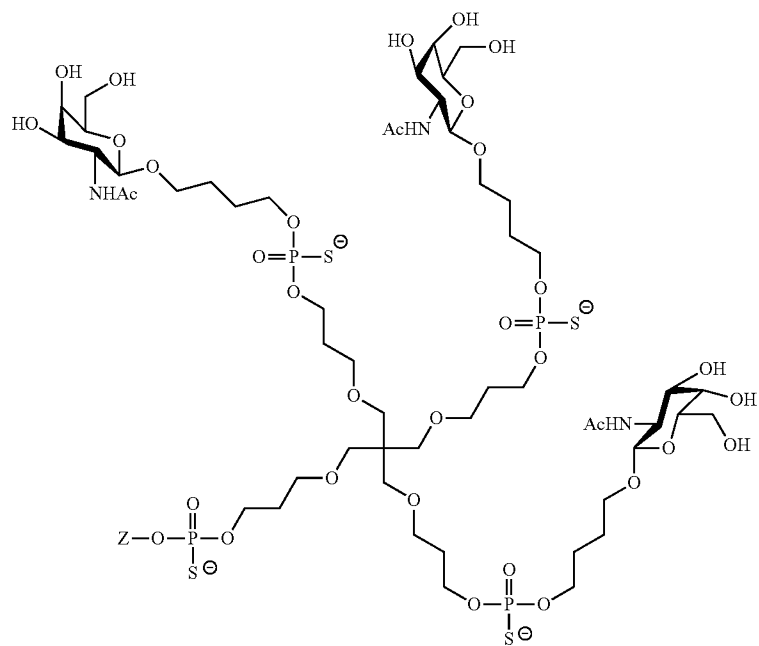
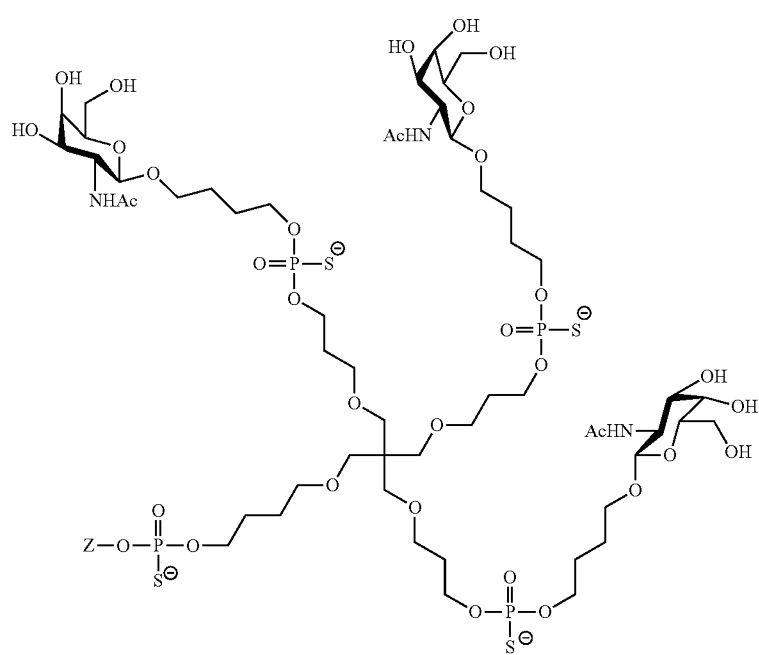

-continued
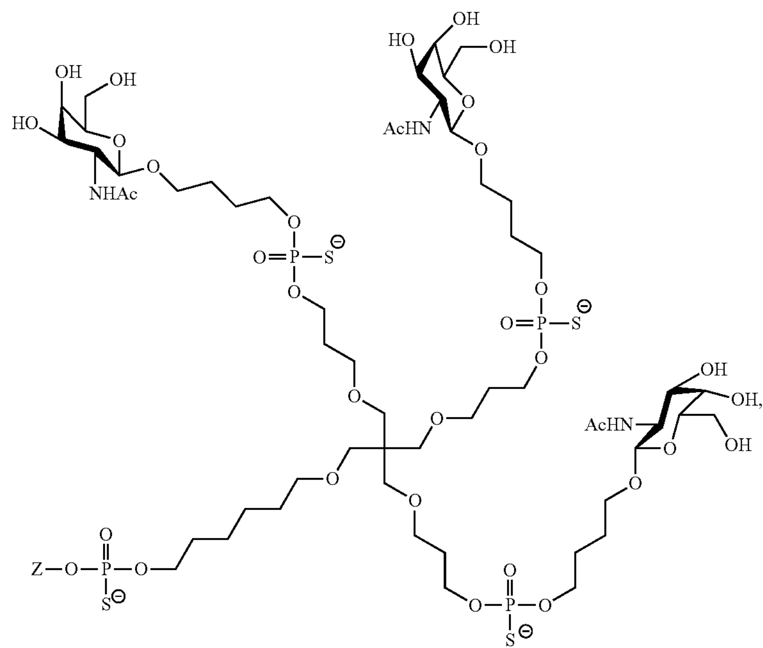
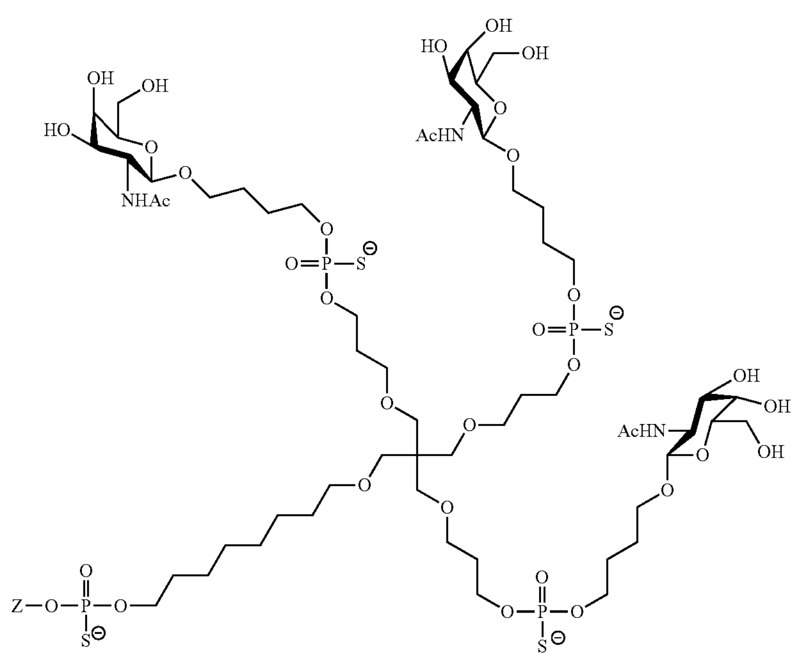

-continued
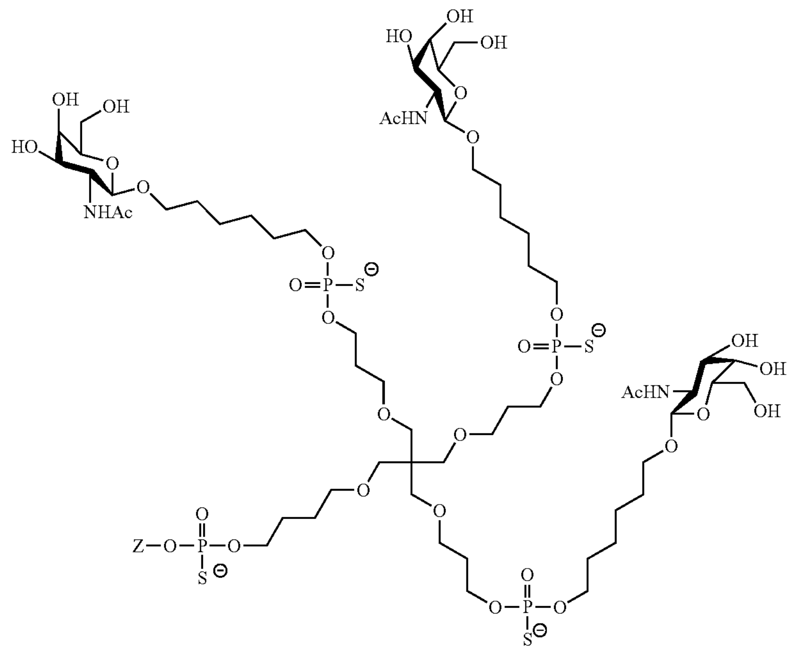
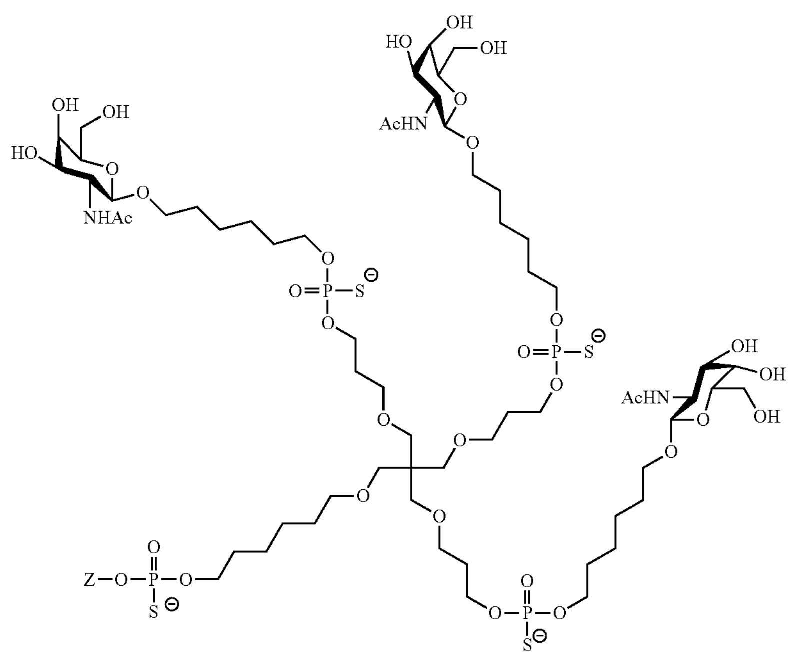

-continued
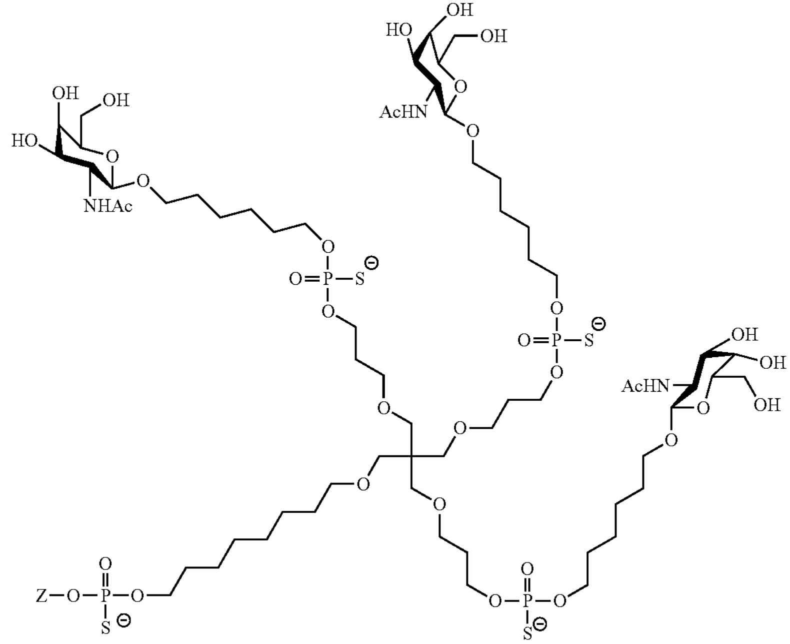
wherein Z represents a nucleic acid as defined herein before.
Preferably, the nucleic acid is a conjugated nucleic acid, wherein the nucleic acid is conjugated to a triantennary ligand with the following structures:
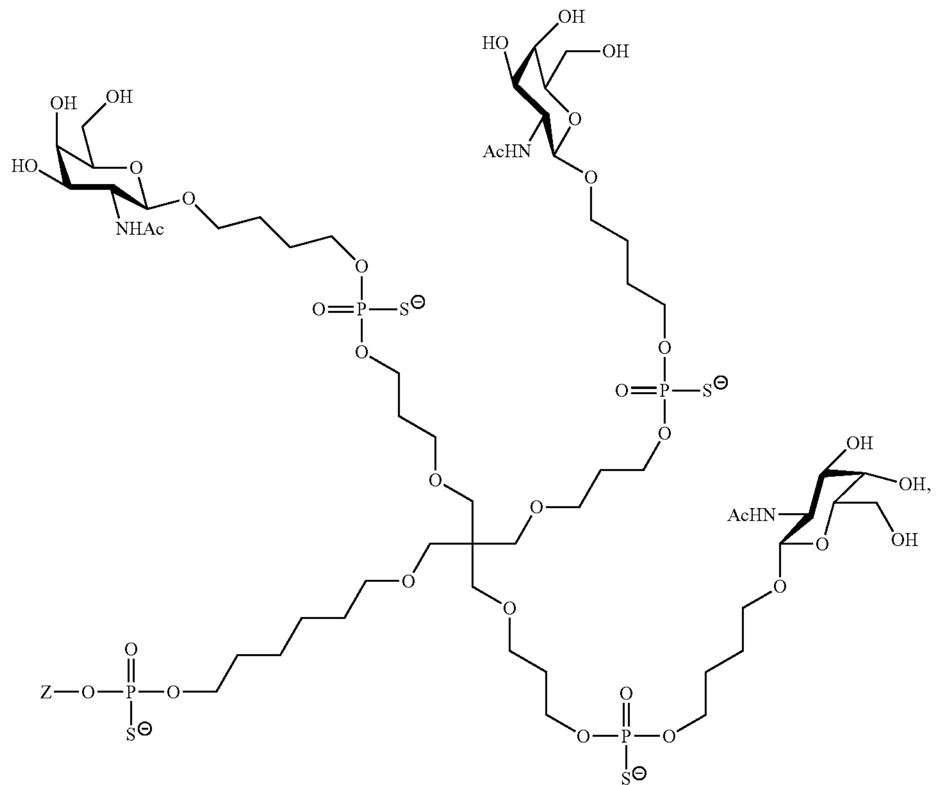

wherein Z represents a nucleic acid as defined herein before.

In one aspect, the nucleic acid is conjugated to a triantennary ligand with the following structure:

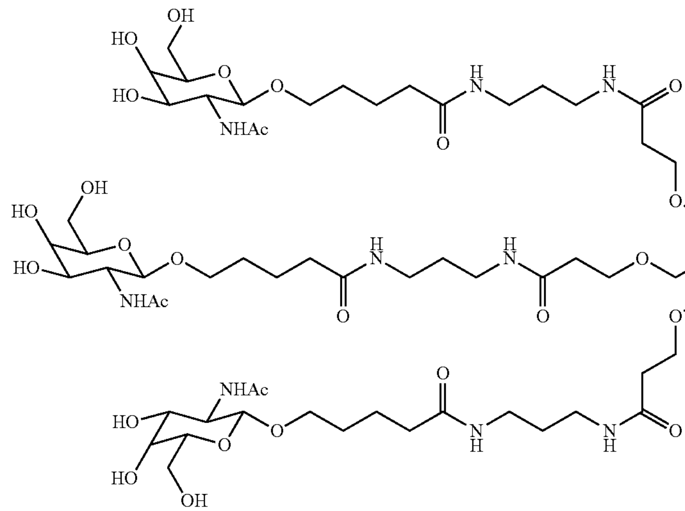

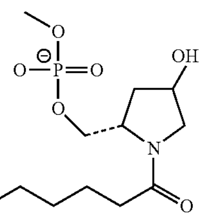

wherein the nucleic acid is conjugated to the ligand via the phosphate group of the ligand a) to the last nucleotide at the 5' end of the second strand; b) to the last nucleotide at the 3' end of the second strand; or c) to the last nucleotide at the 3' end of the first strand.

A ligand of formula (II), (III) or (IV) or any one of the triantennary ligands disclosed herein can be attached at the 3' end of the first (antisense) strand and/or at any of the 3' and/or 5' end of the second (sense) strand. The nucleic acid can comprise more than one ligand of formula (II), (III) or (IV) or any one of the triantennary ligands disclosed herein. However, a single ligand of formula (II), (III) or (IV) or any one of the triantennary ligands disclosed herein is preferred because a single such ligand is sufficient for efficient targeting of the nucleic acid to the target cells. Preferably in that case, at least the last two, preferably at least the last three and more preferably at least the last four nucleotides at the end of the nucleic acid to which the ligand is attached are linked by a phosphodiester linkage.

Preferably, the 5' end of the first (antisense) strand is not attached to a ligand of formula (II), (III) or (IV) or any one of the triantennary ligands disclosed herein, since a ligand in this position can potentially interfere with the biological activity of the nucleic acid.

A nucleic acid with a single ligand of formula (II), (III) or (IV) or any one of the triantennary ligands disclosed herein at the 5' end of a strand is easier and therefore cheaper to synthesis than the same nucleic acid with the same ligand at the 3' end. Preferably therefore, a single ligand of any of formulae (II), (III) or (IV) or any one of the triantennary ligands disclosed herein is covalently attached to (conjugated with) the 5' end of the second strand of the nucleic acid.

One embodiment is a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited, wherein the first strand has a terminal 5' (E)-vinylphosphonate nucleotide, wherein i) the terminal 5' (E)-vinylphosphonate nucleotide is linked to the second nucleotide in the first strand by a phosphodiester linkage, preferably wherein the first strand comprises phosphodiester linkages between at least the terminal three 5' nucleotides;

ii) the first strand comprises at least one phosphorothioate linkage, preferably the first strand comprises a phosphorothioate linkage between the terminal two and more preferably between the terminal three 3' nucleotides;

iii) the second strand is conjugated at the 5' end to a ligand of formula (II), (III) or (IV), preferably to a ligand as shown in FIG. 13*a*, 13*b*, or 13c, more preferably FIG. 13*c*, and the second strand preferably comprises phosphorothioate linkages only between the terminal two, three or four 3' nucleotides, preferably only between the three 3' terminal nucleotides;

iv) at least one, several or all of the nucleotides of the nucleic acid are 2' modified nucleotides;

v) the internucleotide linkages of both strands that are not phosphorothioate linkages are preferably phosphodiester linkages.

The invention provides as a further aspect, a nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of a RNA transcribed from said target gene to be inhibited and wherein the first strand has a terminal 5'-(E)-vinylphosphonate nucleotide, wherein the terminal 5'-(E)-vinylphosphonate nucleotide is linked to the second nucleotide in the first strand by a phosphodiester linkage, and wherein the nucleic acid molecule is conjugated to a ligand.

The nucleic acid may be conjugated to a ligand as herein described. The nucleotides of the first and/or second strand may be modified, as herein described.

The ligand may comprise GalNAc and may be of the structure set out in FIGS. 13*a* or 13*b* or 13*c*, preferably FIG. 13*c*.

In the conjugate of the invention, the ligand portion may comprise a linker moiety and a targeting ligand, and wherein the linker moiety links the targeting ligand to the nucleic acid portion.

The present invention also relates to a conjugate for inhibiting expression of a target gene in a cell, said conjugate comprising a nucleic acid portion and ligand portions, said nucleic acid portion comprising the nucleic acid according to the invention defined anywhere herein, said ligand portions comprising a linker moiety, such as a serinol-derived linker moiety, and a targeting ligand for in vivo targeting of cells and being conjugated exclusively to the 3' and/or 5' ends of one or both RNA strands, wherein the 5' end of the first RNA strand is not conjugated, wherein:

(i) the second RNA strand is conjugated at the 5' end to the targeting ligand, and wherein (a) the second RNA strand is also conjugated at the 3' end to the targeting ligand and the 3' end of the first RNA strand is not conjugated; or (b) the first RNA strand is conjugated at the 3' end to the targeting ligand and the 3' end of the second RNA strand is not conjugated; or (c) both the second RNA strand and the first RNA strand are also conjugated at the 3' ends to the targeting ligand; or (ii) both the second RNA strand and the first RNA strand are conjugated at the 3' ends to the targeting ligand and the 5' end of the second RNA strand is not conjugated.

The present invention also includes a conjugate for inhibiting expression of a TMPRSS6 gene in a cell, said conjugate comprising a nucleic acid portion and ligand portions, said nucleic acid portion comprising a nucleic acid according to the invention defined anywhere herein, wherein the first strand of the nucleic acid is at least partially complementary to at least a portion of RNA transcribed from said TMPRSS6 gene, said ligand portions comprising a linker moiety, such as a serinol-derived linker moiety, and a targeting ligand for in vivo targeting of cells and being conjugated exclusively to the 3' and/or 5' ends of one or both RNA strands, wherein the 5' end of the first RNA strand is not conjugated, wherein:

(i) the second strand is conjugated at the 5' end to the targeting ligand, and wherein (a) the second strand is also conjugated at the 3' end to the targeting ligand and the 3' end of the first strand is not conjugated; and (ii) wherein said first strand includes modified nucleotides at a plurality of positions, and wherein the nucleotides at positions 2 and 14 from the 5' end of the first strand are not modified with a 2'-OMe modification and the second strand positions opposite first strand positions 11, 12, and 13 (corresponding to second strand positions 7, 8, and 9 from the 5' end in a 19-mer) are not modified with 2'-OMe modification.

Optionally, the first strand may comprise the nucleotide sequence:

```
                                          (SEQ ID NO: 9)
(vp)-mU fA mC fC mA fG mA fA mG fA mA fG mC fA mG
fG mU (ps) fG (ps) mA
```

and/or (preferably and) the second strand may comprise the nucleotide sequence:

```
                                         (SEQ ID NO: 10)
Ser(GN) (ps) fU (ps) mC (ps) fA mC fC mU fG mC fU
mU fC mU fU mC fU mG fG (ps) mU (ps) fA (ps)
Ser(GN).
```

The linker moiety may for example be a serinol-derived linker moiety or one of the other linker types described herein.

In an embodiment of the present invention, the second RNA strand (i.e. the sense strand) is conjugated at the 5' end to the targeting ligand, the first RNA strand (i.e. the antisense strand) is conjugated at the 3' end to the targeting ligand and the 3' end of the second RNA strand (i.e. the sense strand) is not conjugated, such that a conjugate with the following schematic structure is formed:

Antisense 5' 3' ligand
Sense 3' 5' ligand.

In an embodiment of the present invention, the second RNA strand (i.e. the sense strand) is conjugated at the 5' end to the targeting ligand, the second RNA strand (i.e. the sense strand) is also conjugated at the 3' end to the targeting ligand and the 3' end of the first RNA strand (i.e. the antisense strand) is not conjugated, such that a conjugate with the following schematic structure is formed:

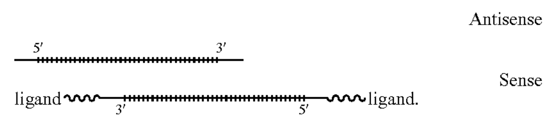

In an embodiment of the present invention, both the second RNA strand (i.e. the sense strand) and the first RNA strand (i.e. the antisense strand) are conjugated at the 3' ends to the targeting ligand and the 5' end of the second RNA strand (i.e. the sense strand) is not conjugated, such that a conjugate with the following schematic structure is formed:

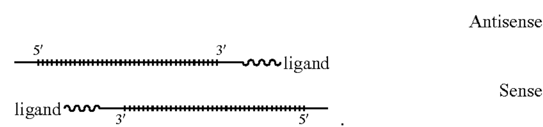

In an embodiment of the present invention, the second RNA strand (i.e. the sense strand) is conjugated at the 5' end to the targeting ligand and both the second RNA strand (i.e. the sense strand) and the first RNA strand (i.e. the antisense strand) are also conjugated at the 3' ends to the targeting ligand, such that a conjugate with the following schematic structure is formed:

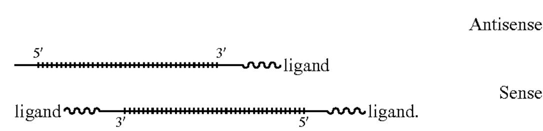

In any one of the above embodiments, ~~~~ indicates the linker which conjugates the ligand to the ends of the nucleic acid portion; the ligand may be a GalNAc moiety such as GalNAc; and wherein represents the nucleic acid portion.

These schematic diagrams are not intended to limit the number of nucleotides in the first or second strand, nor do the diagrams represent any kind of limitation on complementarity of the bases or any other limitation.

The ligands may be monomeric or multimeric (e.g. dimeric, trimeric, etc.).

Suitably, the ligands are monomeric, thus containing a single targeting ligand moiety, e.g. a single GalNAc moiety.

Alternatively, the ligands may be dimeric ligands wherein the ligand portions comprise two linker moieties, such as serinol-derived linker moieties, each linked to a single targeting ligand moiety.

The ligands may be trimeric ligands wherein the ligand portions comprise three linker moieties, such as serinol-derived linker moieties, each linked to a single targeting ligand moiety.

The two or three linker moieties, such as serinol-derived linker moieties may be linked in series e.g. as shown below:

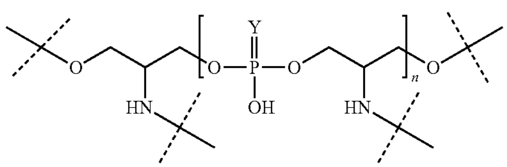

wherein n is 1 or 2 and Y is S or O.

Preferably, the ligands are monomeric.

Suitably, the conjugated RNA strands are conjugated to a targeting ligand via a linker moiety, preferably a serinol-derived linker moiety, including a further linker wherein the further linker is or comprises a saturated, unbranched or branched $C_{1-15}$ alkyl chain, wherein optionally one or more carbons (for example 1, 2 or 3 carbons, suitably 1 or 2, in particular 1) is/are replaced by a heteroatom selected from O, N, $S(O)_p$, wherein p is 0, 1 or 2 (for example a $CH_2$ group is replaced with 0, or with NH, or with S, or with $SO_2$ or a —$CH_3$ group at the terminus of the chain or on a branch is replaced with OH or with $NH_2$) wherein said chain is optionally substituted by one or more oxo groups (for example 1 to 3, such as 1 group).

Suitably, the linker moiety is a serinol-derived linker moiety. The term "serinol-derived linker moiety" means the linker moiety comprises the following structure:

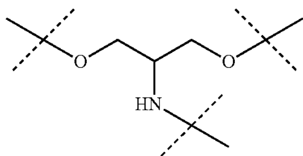

An O atom of said structure typically links to an RNA strand and the N atom typically links to the targeting ligand.

More suitably, the further linker comprises a saturated, unbranched C1-15 alkyl chain wherein one or more carbons (for example 1, 2 or 3 carbons, suitably 1 or 2, in particular 1) is/are replaced by an oxygen atom.

More suitably, the further linker comprises a PEG-chain.

More suitably, the further linker comprises a saturated, unbranched $C_{1-15}$ alkyl chain.

More suitably, the further linker comprises a saturated, unbranched $C_{1-6}$ alkyl chain.

More suitably, the further linker comprises a saturated, unbranched $C_4$ or $C_6$ alkyl chain, e.g. a $C_4$ alkyl chain.

In an embodiment, 〰 is a linking moiety of formula (V):

(V)

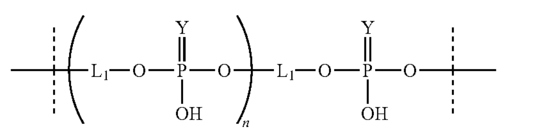

wherein n, Y and L, are defined below and the O of the phosphoro-group is attached to the terminal oligonucleoside of the RNA strands.

Thus in an embodiment, the targeting ligand portion is a linking moiety of formula (VI):

(VI)

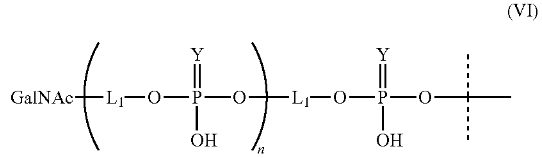

wherein n, Y and L, are defined below and the O of the phosphoro-group is attached to the terminal oligonucleoside of the RNA strands.

Suitably 〰 is a linking moiety of formula (VII):

(VII)

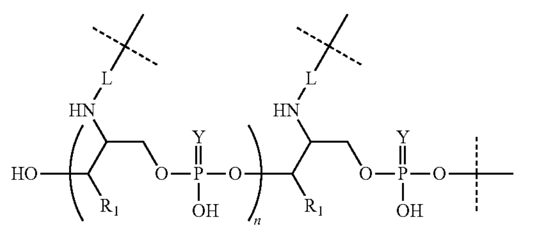

wherein n, Y, $R_1$ and L are defined below, L is connected to the targeting ligand e.g. GalNAc and the O of the phosphoro-group is attached to the terminal oligonucleoside of the RNA strands.

Suitably, the targeting ligand portion is a linking moiety of formula (VIII):

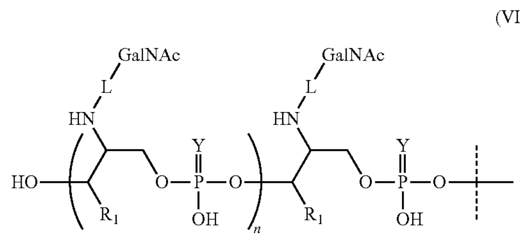

wherein n, Y, $R_1$ and L are defined below and the O of the phosphoro-group is attached to the terminal oligonucleoside of the RNA strands.

Suitably, ∿∿∿ is a linking moiety of formula (IX):

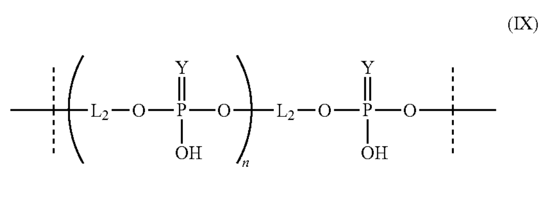

wherein n, Y and $L_2$ are defined below an the o the phosphoro-group is attached to the terminal oligonucleoside of the RNA strands.

Suitably, the targeting ligand portion is a linking moiety of formula (X):

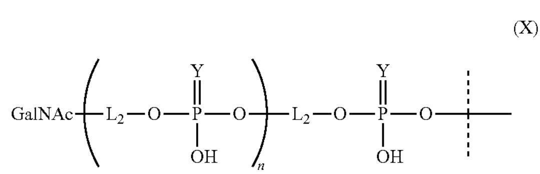

wherein n, Y and $L_2$ are defined below an the o the phosphoro-group is attached to the terminal oligonucleoside of the RNA strands.

Suitably, ∿∿∿ is a linking moiety of formula (XI):

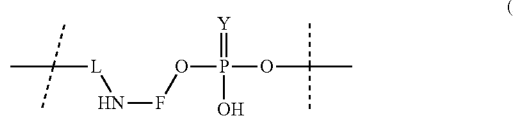

wherein F, Y and L are defined below and the O of the phosphoro-group is attached to the terminal oligonucleoside of the RNA strands.

Suitably, the targeting ligand portion is a linking moiety of formula (XII):

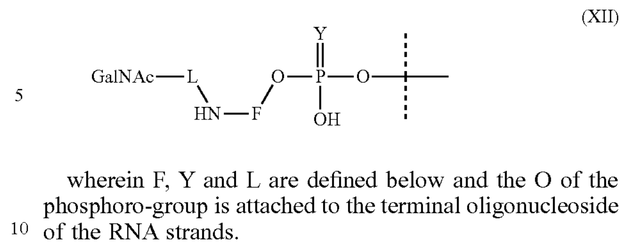

wherein F, Y and L are defined below and the O of the phosphoro-group is attached to the terminal oligonucleoside of the RNA strands.

In any of the above structures, suitably the ligands are selected from GalNAc and galactose moieties, especially GalNAc moieties. Alternatively, GalNac may be replaced by another targeting ligand, e.g. a saccharide.

In an embodiment of the invention, the first RNA strand is a compound of formula (XIII):

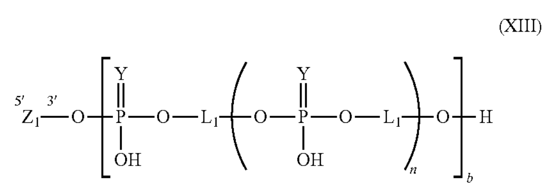

wherein b is preferably 0 or 1; and the second RNA strand is a compound of formula (XIV):

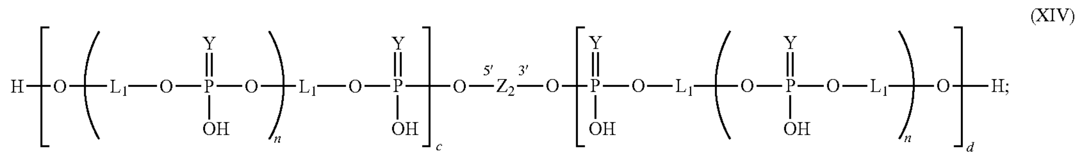

wherein:

c and d are independently preferably 0 or 1;

$Z_1$ and $Z_2$ are the RNA portions of the first and second RNA strands respectively;

Y is O or S;

n is 0, 1, 2 or 3; and $L_1$ is a linker to which a ligand is attached;

and wherein b+c+d is preferably 2 or 3.

Preferably, L, in formulae (XIII) and (XIV) is of formula (XV):

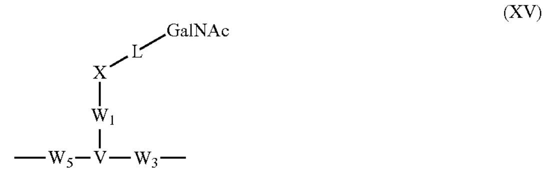

wherein:

L is selected from the group comprising, or preferably consisting of:

—$(CH_2)_r$—C(O)—, wherein r=2-12;

—$(CH_2$—$CH_2$—$O)_s$—$CH_2$—C(O)—, wherein s=1-5;

—$(CH_2)_t$—CO—NH—$(CH_2)_t$—NH—C(O)—, wherein t is independently 1-5;

—$(CH_2)_u$—CO—NH—$(CH_2)$, —C(O)—, wherein u is independently 1-5; and

—$(CH_2)_v$—NH—C(O)—, wherein v is 2-12; and wherein the terminal C(O), if present, is attached to X of formula (XV), or if X is absent, to $W_1$ of formula (XV), or if $W_1$ is also absent, to V of formula (XV); $W_1$, $W_3$ and $W_5$ are individually absent or selected from the group comprising, or preferably consisting of:

—$(CH_2)_r$—, wherein r=1-7;

—$(CH_2)_s$—O—$(CH_2)_s$—, wherein s is independently 0-5;

—$(CH_2)_t$—S—$(CH_2)_t$—, wherein t is independently 0-5;

X is absent or is selected from the group comprising, or preferably consisting of: NH, $NCH_3$ or $NC_2H_5$;

V is selected from the group comprising, or preferably consisting of:

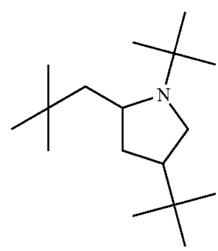

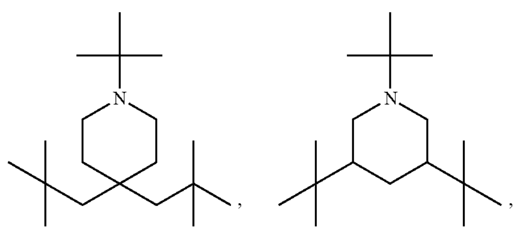

-continued

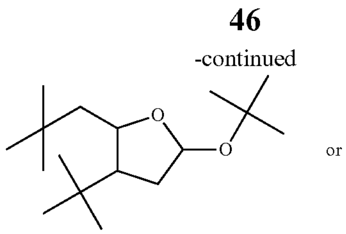

or

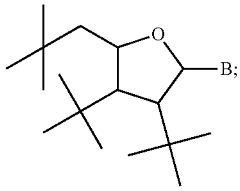

wherein B, if present, is a modified or natural nucleobase.

Suitably, the first RNA strand is a compound of formula (XVI):

(XVI)

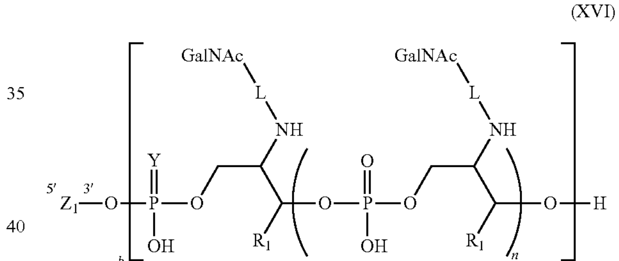

wherein b is 0 or 1; and the second RNA strand is a compound of formula (XVII):

(XVII)

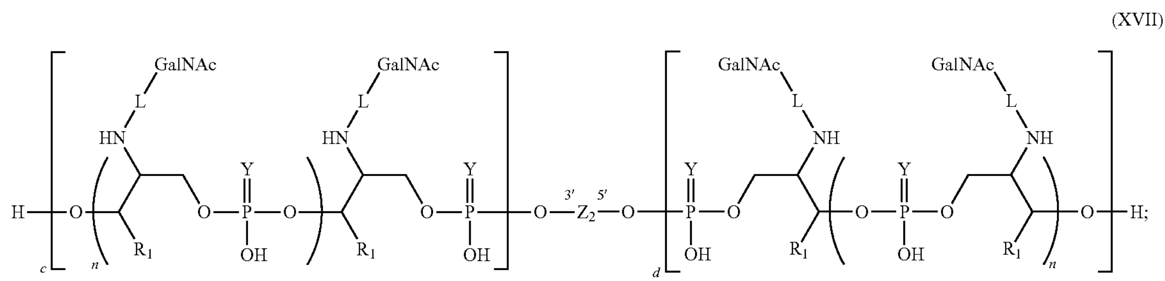

wherein c and d are independently 0 or 1;

wherein:

$Z_1$ and $Z_2$ are the RNA portions of the first and second RNA strands respectively;

Y is O or S;

$R_1$ is H or methyl;

n is 0, 1, 2 or 3; and

L is the same or different in formulae (XVI) and (XVII) and is selected from the group consisting of:

—$(CH_2)_r$—C(O)—, wherein r=2-12;

—$(CH_2$—$CH_2$—$O)_s$—$CH_2$—C(O)—, wherein s=1-5;

—$(CH_2)_t$—CO—NH—$(CH_2)_t$—NH—C(O)—, wherein t is independently is 1-5;

—$(CH_2)_u$—CO—NH—$(CH_2)$, —C(O)—, wherein u is independently is 1-5; and

—$(CH_2)_v$—NH—C(O)—, wherein v is 2-12; and wherein the terminal C(O) (if present) is attached to the NH group;

and wherein b+c+d is 2 or 3.

In one instance, b is 0, c is 1 and d is 1. In another instance, b is 1, c is 0 and d is 1. In another instance, b is 1, c is 1 and d is 0. In another instance, b is 1, c is 1 and d is 1.

In one instance, Y is O. In another instance, Y is S.

In one instance, $R_1$ is H. In another instance, $R_1$ is methyl.

In one instance, n is 0.

In one instance, L is —$(CH_2)_r$—C(O)—, wherein r=2-12. Preferably, r=2-6. More preferably, r=4 or 6 e.g. 4.

In one aspect, the first strand is a compound of formula (XVIII)

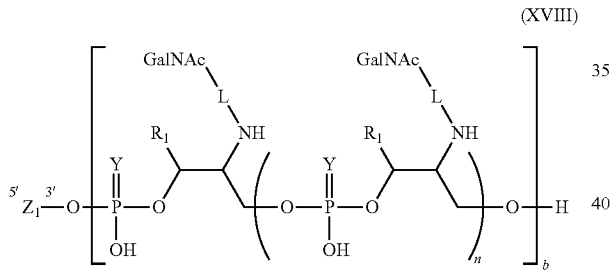

wherein b is preferably 0 or 1; and the second strand is a compound of formula (XIX):

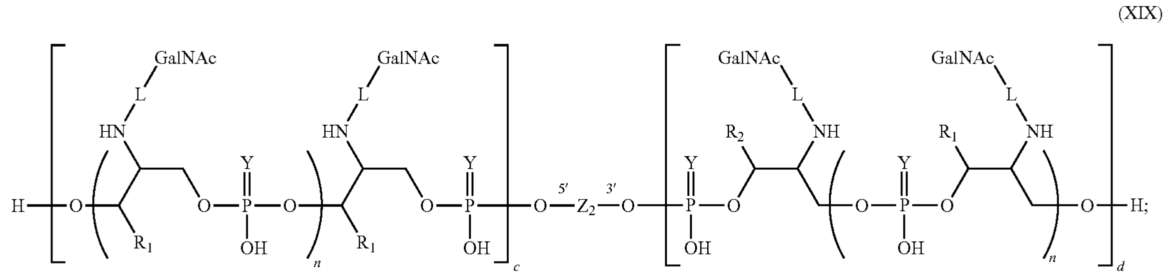

wherein c and d are independently preferably 0 or 1;

wherein:

$Z_1$ and $Z_2$ are the RNA portions of the first and second RNA strands respectively;

Y is independently O or S;

$R_1$ is H or methyl;

n is independently preferably 0, 1, 2 or 3; and

L is the same or different in formulae (XVIII) and (XIX), and is the same or different within formulae (XVIII) and (XIX) when L is present more than once within the same formula, and is selected from the group comprising, or preferably consisting of:

—$(CH_2)_r$—C(O)—, wherein r=2-12;

—$(CH_2$—$CH_2$—$O)_s$—$CH_2$—C(O)—, wherein s=1-5;

—$(CH_2)_t$—CO—NH—$(CH_2)_t$—NH—C(O)—, wherein t is independently 1-5;

—$(CH_2)_u$—CO—NH—$(CH_2)$, —C(O)—, wherein u is independently 1-5; and

—$(CH_2)_v$—NH—C(O)—, wherein v is 2-12; and wherein the terminal C(O), if present, is attached to the NH group (of the linker, not of the targeting ligand);

and wherein b+c+d is preferably 2 or 3.

Suitably, the first RNA strand is a compound of formula (XX):

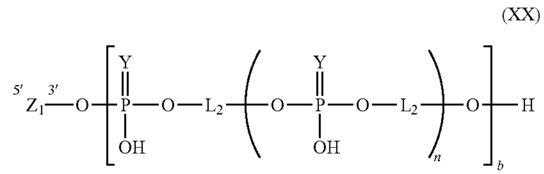

wherein b is preferably 0 or 1; and the second RNA strand is a compound of formula (XXI):

(XXI)

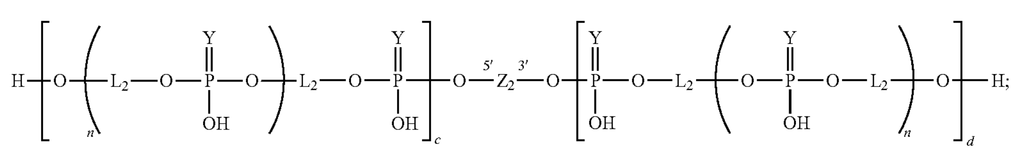

wherein:

c and d are independently preferably 0 or 1;

$Z_1$ and $Z_2$ are the RNA portions of the first and second RNA strands respectively;

Y is O or S;

n is 0, 1, 2 or 3; and $L_2$ is the same or different in formulae (XX) and (XXI) and is the same or different in moieties bracketed by b, c and d, and is selected from the group consisting of:

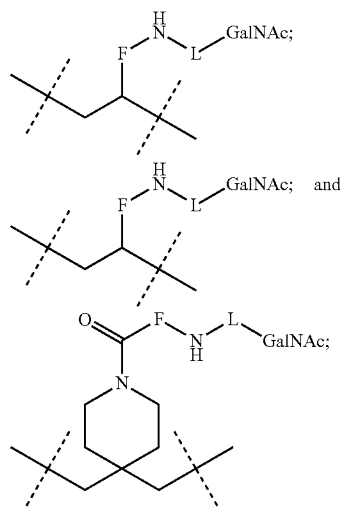

or n is 0 and $L_2$ is:

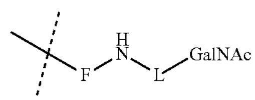

and the terminal OH group is absent such that the following moiety is formed:

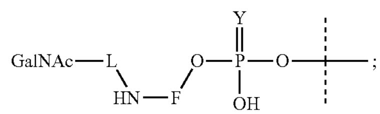

wherein

F is a saturated branched or unbranched (such as unbranched) $C_{1-8}$alkyl (e.g. $C_{1-6}$alkyl) chain wherein one of the carbon atoms is optionally replaced with an oxygen atom provided that said oxygen atom is separated from another heteroatom (e.g. an O or N atom) by at least 2 carbon atoms;

L is the same or different in formulae (XX) and (XXI) and is selected from the group consisting of:

—$(CH_2)_r$—C(O)—, wherein r=2-12;

—$(CH_2$—$CH_2$—$O)_s$—$CH_2$—C(O)—, wherein s=1-5;

—$(CH_2)_t$—CO—NH—$(CH_2)_t$—NH—C(O)—, wherein t is independently is 1-5;

—$(CH_2)_u$—CO—NH—$(CH_2)$, —C(O)—, wherein u is independently is 1-5; and

—$(CH_2)_v$—NH—C(O)—, wherein v is 2-12; and wherein the terminal C(O) (if present) is attached to the NH group;

and wherein b+c+d is preferably 2 or 3.

In any one of the above formulae where GalNAc is present, the GalNAc may be substituted for any other targeting ligand, such as those mentioned herein.

Suitably, b is 0, c is 1 and d is 1; b is 1, c is 0 and d is 1; b is 1, c is 1 and d is 0; or b is 1, c is 1 and d is 1.

More suitably, b is 0, c is 1 and d is 1; b is 1, c is 0 and d is 1; or b is 1, c is 1 and d is 1.

Most suitably, b is 0, c is 1 and d is 1.

In one embodiment, Y is O. In another embodiment, Y is S.

In one embodiment, $R_1$ is H or methyl. In one embodiment, $R_1$ is H. In another embodiment, $R_1$ is methyl.

In one embodiment, n is 0, 1, 2 or 3. Suitably, n is 0.

In one embodiment, L is selected from the group consisting of:

—$(CH_2)_r$C(O)—, wherein r=2-12;

—$(CH_2$—$CH_2$—$O)_s$—$CH_2$—C(O)—, wherein s=1-5;

—$(CH_2)_t$—CO—NH—$(CH_2)_t$—NH—C(O)—, wherein t is independently is 1-5;

—$(CH_2)_u$—CO—NH—$(CH_2)$, —C(O)—, wherein u is independently is 1-5; and

—$(CH_2)^v$—NH—C(O)—, wherein v is 2-12;

wherein the terminal C(O) is attached to the NH group.

Suitably, L is —$(CH_2)_r$—C(O)—, wherein r=2-12. Suitably, r=2-6. More suitably, r=4 or 6 e.g. 4.

Suitably, L is:

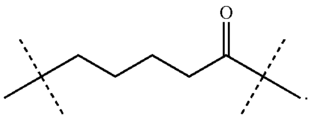

Example F moieties include $(CH_2)_{1-6}$ e.g. $(CH_2)_{1-4}$ e.g. $CH_2$, $(CH_2)_4$, $(CH_2)_5$ or $(CH_2)_6$, or $CH_2O(CH_2)_{2-3}$, e.g. $CH_2O(CH_2)CH_3$.

Suitably, $L_2$ is:

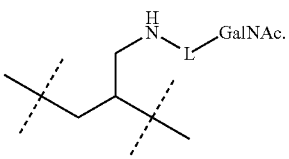

Suitably, $L_2$ is:

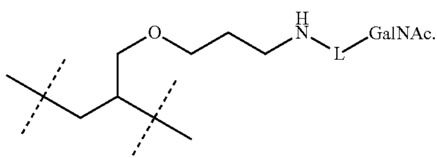

Suitably, $L_2$ is:

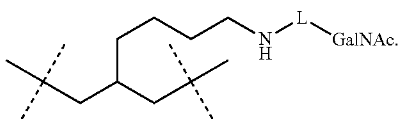

Suitably, $L_2$ is:

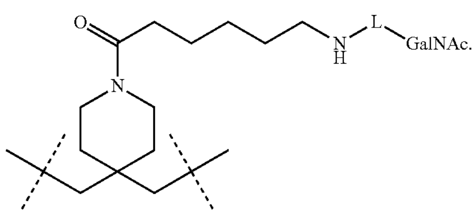

Suitably, n is 0 and $L_2$ is:

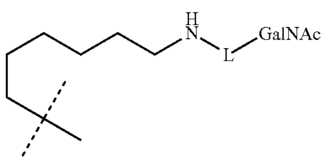

and the terminal OH group is absent such that the following moiety is formed:

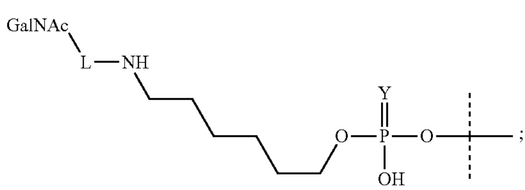

wherein Y is as defined elsewhere herein.

Within the moiety bracketed by b, c and d, $L_2$ is typically the same. Between moieties bracketed by b, c and d, $L_2$ may be the same or different. In an embodiment, $L_2$ in the moiety bracketed by c is the same as the $L_2$ in the moiety bracketed by d. In an embodiment, $L_2$ in the moiety bracketed by c is not the same as $L_2$ in the moiety bracketed by d. In an embodiment, the $L_2$ in the moieties bracketed by b, c and d is the same, for example when the linker moiety is a serinol-derived linker moiety.

Serinol-derived linker moieties may be based on serinol in any stereochemistry i.e. derived from L-serine isomer, D-serine isomer, a racemic serine or other combination of isomers. In a preferred aspect of the invention, the serinol-GalNAc moiety (SerGN) has the following stereochemistry:

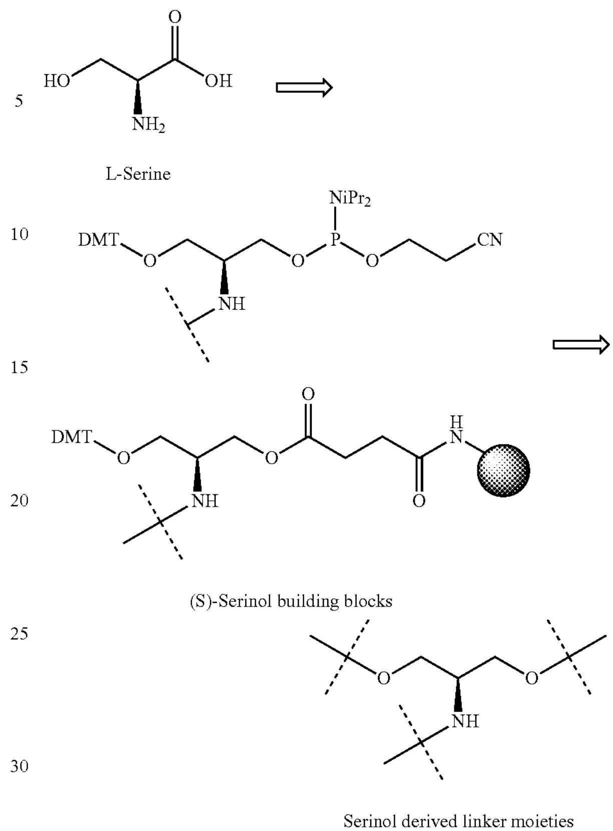

i.e. is based on an (S)-serinol-amidite or (S)-serinol succinate solid supported building block derived from L-serine isomer.

In a preferred aspect, the first strand of the nucleic acid is a compound of formula (XVIII) and the second strand of the nucleic acid is a compound of formula (XIX), wherein:

b is 0;

c and d are 1;

n is 0;

$Z_1$ and $Z_2$ are respectively the first and second strand of the nucleic acid;

Y is S;

$R_1$ is H; and

L is —$(CH_2)_4$—C(O)—, wherein the terminal C(O) of L is attached to the N atom of the linker (ie not a possible N atom of a targeting ligand).

In another preferred aspect, the first strand of the nucleic acid is a compound of formula (XIII) and the second strand of the nucleic acid is a compound of formula (XIV), wherein:

b is 0;

c and d are 1;

n is 0;

$Z_1$ and $Z_2$ are respectively the first and second strand of the nucleic acid;

Y is S; and $L_1$ is of formula (XV), wherein:

$W_1$ is —$CH_2$—O—$(CH_2)_3$—;

$W_3$ is —$CH_2$—;

$W_5$ is absent;

V is CH;

X is NH; and

L is —$(CH_2)_4$—C(O)— wherein the terminal C(O) of L is attached to the N atom of X in formula (XV).

In another preferred aspect, the first strand of the nucleic acid is a compound of formula (XIII) and the second strand of the nucleic acid is a compound of formula (XIV), wherein:

b is 0;

c and d are 1;

n is 0;

$Z_1$ and $Z_2$ are respectively the first and second strand of the nucleic acid;

Y is S;

$L_1$ is of formula (XV), wherein:

$W_1$, $W_3$ and $W_5$ are absent;

V is

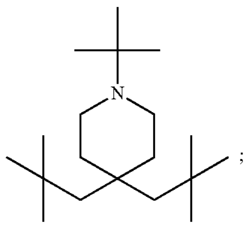 [SMILES: CC(C)(C)CC1(CC(C)(C)C)CCN(C(C)(C)C)CC1]

X is absent; and

L is —$(CH_2)_4$—C(O)—NH—$(CH_2)_5$—C(O)—, wherein the terminal C(O) of L is attached to the N atom of V in formula (XV).

In one embodiment, the targeted cells are hepatocytes.

In one embodiment, the linker moiety is a serinol-derived linker moiety, and the targeting ligand is conjugated exclusively to the 3' and/or 5' ends of one or both of the first and seconds strands of the nucleic acid, wherein the 5' end of the first strand is not conjugated, wherein:

(i) the second strand is conjugated at the 5' end to the targeting ligand, and wherein (a) the second strand is also conjugated at the 3' end to the targeting ligand and the 3' end of the first strand is not conjugated; or (b) the first strand is conjugated at the 3' end to the targeting ligand and the 3' end of the second strand is not conjugated; or (c) both the second strand and the first strand are also conjugated at the 3' ends to the targeting ligand; or (ii) both the second strand and the first strand are conjugated at the 3' ends to the targeting ligand and the 5' end of the second strand is not conjugated; and (iii) wherein said first strand includes modified nucleotides at a plurality of positions, and wherein the nucleotides at positions 2 and 14 from the 5' end of the first strand are not modified with a 2'-OMe modification (i.e. they have a modification other than 2'-OMe or are unmodified).

In one embodiment of the conjugate of the invention, the second strand is conjugated at the 5' end to the targeting ligand, the second strand is also conjugated at the 3' end to the targeting ligand and the 3' end of the first strand is not conjugated.

In one embodiment of the conjugate of the invention, the second strand is conjugated at the 5' end to the targeting ligand, the first strand is conjugated at the 3' end to the targeting ligand and the 3' end of the second strand is not conjugated.

In one embodiment of the conjugate of the invention, the second strand is conjugated at the 5' end to the targeting ligand and both the second strand and the first strand are also conjugated at the 3' ends to the targeting ligand.

In one embodiment of the conjugate of the invention, both the second strand and the first strand are conjugated at the 3' ends to the targeting ligand and the 5' end of the second strand is not conjugated.

Inverted Nucleotide

In one embodiment of the nucleic acid or conjugate of the invention, the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, or wherein the nucleic acid comprises a phosphorodithioate linkage.

The nucleic acid of the invention may comprise an inverted RNA nucleotide at one or several of the strand ends. Such inverted nucleotides provide stability to the nucleic acid. Preferably, the nucleic acid comprises at least an inverted nucleotide at the 3' end of the first and/or the second strand and/or at the 5' end of the second strand. More preferably, the nucleic acid comprises an inverted nucleotide at the 3' end of the second strand. Most preferably, the nucleic acid comprises an inverted RNA nucleotide at the 3' end of the second strand and this nucleotide is preferably an inverted A. An inverted nucleotide is a nucleotide that is linked to the 3' end of a nucleic acid through its 3' carbon, rather than its 5' carbon as would normally be the case or is linked to the 5' end of a nucleic acid through its 5' carbon, rather than its 3' carbon as would normally be the case. The inverted nucleotide is preferably present at an end of a strand not as an overhang but opposite a corresponding nucleotide in the other strand. Accordingly, the nucleic acid is preferably blunt-ended at the end that comprises the inverted RNA nucleotide. An inverted RNA nucleotide being present at the end of a strand preferably means that the last nucleotide at this end of the strand is the inverted RNA nucleotide. A nucleic acid with such a nucleotide is stable and easy to synthesise. The inverted RNA nucleotide is preferably an unmodified nucleotide in the sense that it does not comprise any modifications compared to the natural nucleotide counterpart. Specifically, the inverted RNA nucleotide is preferably a 2'-OH nucleotide.

Cleavable Linker

A cleavable linking group is a linker which is stable outside the cell but is cleaved upon entry into a target cell. Cleavage releases the two parts the linker is holding together.

In a preferred embodiment, the nucleic acid of the invention comprises a cleavable linking group that is cleaved at least 10 times or more, preferably at least 100-fold faster in a target cell or under a first reference condition (which can, for example, be selected to mimic or represent intracellular conditions) than in the blood of a subject, or under a second reference condition (which can, for example, be selected to mimic or represent conditions found in the blood or serum).

Cleavable linking groups are susceptible to cleavage agents, e.g. pH, redox potential, or the presence of degradative molecules. Degradative molecules include oxidative or reductive enzymes, reductive agents (such as mercaptans), esterases, endosomes or agents than can create an acidic environment, enzymes that can hydrolyze or degrade an acid cleavable linking group by acting as a general acid, peptidases, and phosphatases.

A cleavable linking group may be a disulphide bond, which is susceptible to pH.

A linker may include a cleavable linking group that is cleavable by a particular enzyme. The type of cleavable linking group incorporated into a linker can depend on the target cell. For example, a linker that includes an ester group is preferred when a liver cell is the target. Linkers that contain peptide bonds can be used when targeting cells rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. In preferred embodiments, useful candidate compounds are cleaved at least 2, 4, 10 or 100 times faster in the cell (or under in vitro conditions selected to mimic intracellular conditions) as compared to blood or serum (or under in vitro conditions selected to mimic extracellular conditions).

In one aspect, the cleavable linking group may be a redox cleavable linking group. The redox cleavable linking group may be a disulphide linking group.

In one aspect, the linking group may be a phosphate-based cleavable linking group.

Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O—, —S—P(S)(H)—O—, —S—P(O)(H)—S—, —O—P(S)(H)—S—. A preferred embodiment is —O—P(O)(OH)—O—.

In one aspect, the cleavable linking group may be an acid cleavable linking group. Preferably the acid cleavable linking group are cleaved in environments where the pH is 6.5 or lower, or are cleaved by agents such as enzymes that can act as a general acid. Examples of acid cleavable linking groups include but are not limited to hydrazones, esters, and esters of amino acids. Acid cleavable groups can have the general formula —C═NN—; C(O)O, or —OC(O). A preferred embodiment is a linking group where the carbon attached to the oxygen of the ester (the alkoxy group) is an aryl group, substituted alkyl group, or tertiary alkyl group such as dimethyl pentyl or t-butyl.

In one embodiment, the cleavable linking group may be an ester-based cleavable linking group. Examples of ester-based cleavable linking groups include but are not limited to esters of alkylene, alkenylene and alkynylene groups.

In one embodiment, the cleavable linking group may be a peptide-based cleavable linking group. Peptide-based cleavable linking groups are peptide bonds formed between amino acids to yield oligopeptides (e.g., dipeptides, tripeptides etc.) and polypeptides. The peptide based cleavage group is generally limited to the peptide bond (i.e., the amide bond) formed between amino acids yielding peptides and proteins and does not include the entire amide functional group. Peptide-based cleavable linking groups have the general formula —NHCHR$^A$C(O)NHCHR$^B$C(O)—, where R$^A$ and RB are the R groups of the two adjacent amino acids.

Lipid Formulation

The nucleic acid as described herein may be formulated with a lipid in the form of a liposome. Such a formulation may be described in the art as a lipoplex. The composition with a lipid/liposome may be used to assist with delivery of the nucleic acid of the invention to the target cells. The lipid delivery system herein described may be used as an alternative to a conjugated ligand. The modifications herein described may be present when using the nucleic acid of the invention with a lipid delivery system or with a ligand conjugate delivery system.

Such a lipoplex may comprise a lipid composition comprising:

i) a cationic lipid, or a pharmaceutically acceptable salt thereof;
ii) a steroid;
iii) a phosphatidylethanolamine phospholipid;
iv) a PEGylated lipid.

The cationic lipid may be an amino cationic lipid.

The cationic lipid may have the formula (XXII):

(XXII)

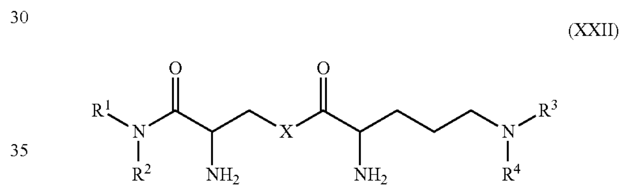

or a pharmaceutically acceptable salt thereof, wherein:

X represents O, S or NH;

R$^1$ and R$^2$ each independently represents a $C_4$-$C_{22}$ linear or branched alkyl chain or a $C_4$-$C_{22}$ linear or branched alkenyl chain with one or more double bonds, wherein the alkyl or alkenyl chain optionally contains an intervening ester, amide or disulfide; when X represents S or NH, R$^3$ and R$^4$ each independently represent hydrogen, methyl, ethyl, a mono- or polyamine moiety, or R$^3$ and R$^4$ together form a heterocyclyl ring; when X represents 0, R$^3$ and R$^4$ each independently represent hydrogen, methyl, ethyl, a mono- or polyamine moiety, or R$^3$ and R$^4$ together form a heterocyclyl ring, or R$^3$ represents hydrogen and R$^4$ represents C(NH)(NH$_2$).

The cationic lipid may have the formula (XXIII):

(XXIII)

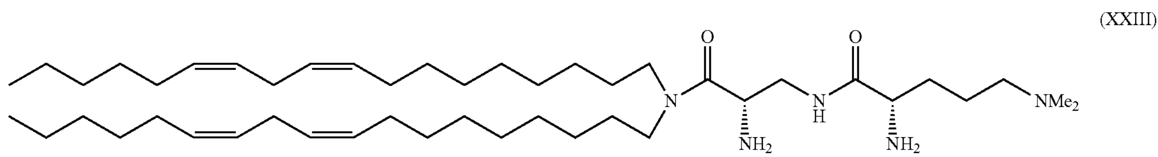 [SMILES: CCCCC/C=C\C/C=C\CCCCCCCCN(CCCCCCCC/C=C\C/C=C\CCCCC)C(=O)[C@@H](N)CNC(=O)[C@@H](N)CCCN(C)C]

or a pharmaceutically acceptable salt thereof.

The cationic lipid may have the formula (XXIV):

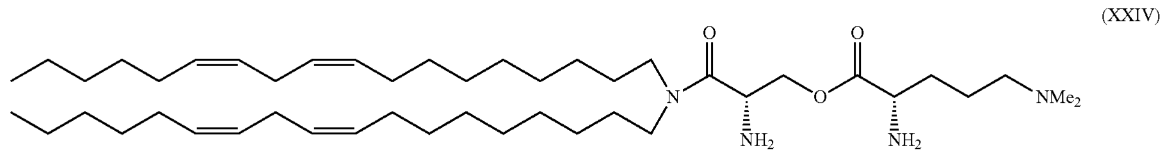 [SMILES: CCCCC/C=C\C/C=C\CCCCCCCCN(CCCCCCCC/C=C\C/C=C\CCCCC)C(=O)[C@@H](N)COC(=O)[C@@H](N)CCCN(C)C]

or a pharmaceutically acceptable salt thereof.

The content of the cationic lipid component may be from about 55 mol % to about 65 mol % of the overall lipid content of the formulation. In particular, the cationic lipid component is about 59 mol % of the overall lipid content of the formulation.

The formulations further comprise a steroid. the steroid may be cholesterol. The content of the steroid may be from about 26 mol % to about 35 mol % of the overall lipid content of the lipid formulation. More particularly, the content of steroid may be about 30 mol % of the overall lipid content of the lipid formulation.

The phosphatidylethanolamine phospholipid may be selected from group consisting of 1,2-diphytanoyl-sn-glycero-3-phosphoethanolamine (DPhyPE), 1,2-dioleoyl-sn-glycero-3-phosphoethanolamine (DOPE), 1,2-distearoyl-sn-glycero-3-phosphoethanolamine (DSPE), 1,2-Dilauroyl-sn-glycero-3-phosphoethanolamine (DLPE), 1,2-Dimyristoyl-sn-glycero-3-phosphoethanolamine (DMPE), 1,2-Dipalmitoyl-sn-glycero-3-phosphoethanolamine (DPPE), 1,2-Dilinoleoyl-sn-glycero-3-phosphoethanolamine (DLoPE), 1-Palmitoyl-2-oleoyl-sn-glycero-3-phosphoethanolamine (POPE), 1,2-Dierucoyl-sn-glycero-3-phosphoethanolamine (DEPE), 1,2-Disqualeoyl-sn-glycero-3-phosphoethanolamine (DSQPE) and 1-Stearoyl-2-linoleoyl-sn-glycero-3-phosphoethanolamine (SLPE). The content of the phospholipid may be about 10 mol % of the overall lipid content of the composition.

The PEGylated lipid may be selected from the group consisting of 1,2-dimyristoyl-sn-glycerol, methoxypolyethylene glycol (DMG-PEG) and C16-Ceramide-PEG. The content of the PEGylated lipid may be about 1 to 5 mol % of the overall lipid content of the formulation.

The content of the cationic lipid component in the composition may be from about 55 mol % to about 65 mol % of the overall lipid content of the lipid formulation, preferably about 59 mol % of the overall lipid content of the lipid formulation.

The composition may have a molar ratio of the components of i):ii):iii):iv) selected from 55:34:10:1; 56:33:10:1; 57:32:10:1; 58:31:10:1; 59:30:10:1; 60:29:10:1; 61:28:10:1; 62:27:10:1; 63:26:10:1; 64:25:10:1; and 65:24:10:1.

The composition may comprise a cationic lipid having the structure

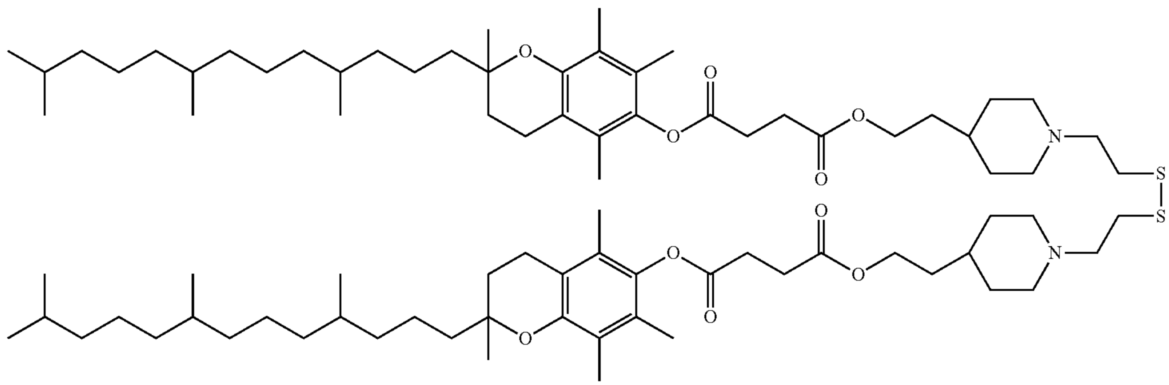 [SMILES: Cc1c(C)c2c(c(C)c1OC(=O)CCC(=O)OCCC1CCN(CCSSCCN3CCC(CCOC(=O)CCC(=O)Oc4c(C)c(C)c5c(c4C)CCC(C)(CCCC(C)CCCC(C)CCCC(C)C)O5)CC3)CC1)CCC(C)(CCCC(C)CCCC(C)CCCC(C)C)O2]

a steroid having the structure

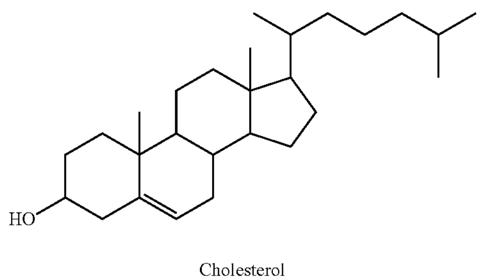 [SMILES: CC(C)CCCC(C)C1CCC2C3CC=C4CC(O)CCC4(C)C3CCC12C]

Cholesterol a phosphatidylethanolamine phospholipid having the structure

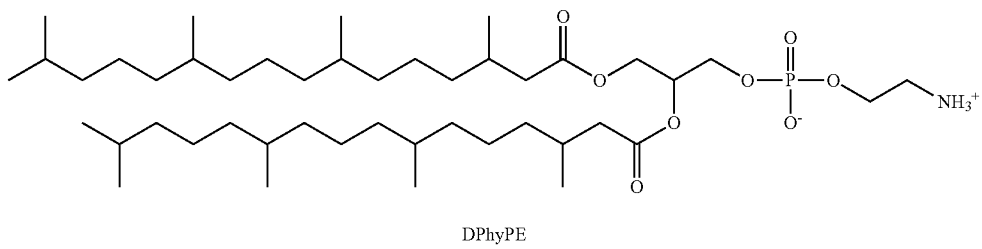 [SMILES: CC(C)CCCC(C)CCCC(C)CCCC(C)CC(=O)OCC(COP(=O)([O-])OCC[NH3+])OC(=O)CC(C)CCCC(C)CCCC(C)CCCC(C)C]

DPhyPE and a PEGylated lipid having the structure

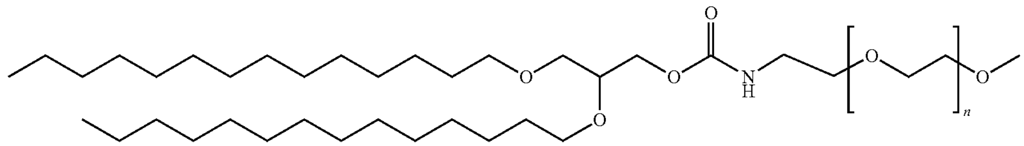

Neutral liposome compositions may be formed from, for example, dimyristoyl phosphatidylcholine (DMPC) or dipalmitoyl phosphatidylcholine (DPPC). Anionic liposome compositions may be formed from dimyristoyl phosphatidylglycerol, while anionic fusogenic liposomes may be formed primarily from dioleoyl phosphatidylethanolamine (DOPE). Another type of liposomal composition may be formed from phosphatidylcholine (PC) such as, for example, soybean PC, and egg PC. Another type is formed from mixtures of phospholipid and/or phosphatidylcholine and/or cholesterol.

A positively charged synthetic cationic lipid, N-[I-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells. DOTMA analogues can also be used to form liposomes.

Derivatives and analogues of lipids described herein may also be used to form liposomes.

A liposome containing a nucleic acid can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The nucleic acid preparation is then added to the micelles that include the lipid component. The cationic groups on the lipid interact with the nucleic acid and condense around the nucleic acid to form a liposome. After condensation, the detergent is removed, e.g., by dialysis, to yield a liposomal preparation of nucleic acid.

If necessary a carrier compound that assists in condensation can be added during the condensation reaction, e.g., by controlled addition. For example, the carrier compound can be a polymer other than a nucleic acid (e.g., spermine or spermidine). pH can also be adjusted to favour condensation.

Surfactants

Nucleic acid formulations may include a surfactant. In one embodiment, the nucleic acid is formulated as an emulsion that includes a surfactant.

A surfactant that is not ionized is a non-ionic surfactant. Examples include non-ionic esters, such as ethylene glycol esters, propylene glycol esters, glyceryl esters etc., nonionic alkanolamides, and ethers such as fatty alcohol ethoxylates, propoxylated alcohols, and ethoxylated/propoxylated block polymers.

A surfactant that carries a negative charge when dissolved or dispersed in water is an anionic surfactant. Examples include carboxylates, such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates.

A surfactant that carries a positive charge when dissolved or dispersed in water is a cationic surfactant. Examples include quaternary ammonium salts and ethoxylated amines.

A surfactant that has the ability to carry either a positive or negative charge is an amphoteric surfactant. Examples include acrylic acid derivatives, substituted alkylamides, N-alkylbetaines and phosphatides.

"Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic. A micelle may be formed by mixing an aqueous solution of the nucleic acid, an alkali metal alkyl sulphate, and at least one micelle forming compound.

Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof.

Phenol and/or m-cresol may be added to the mixed micellar composition to act as a stabiliser and preservative. An isotonic agent such as glycerine may as be added.

A nucleic acid preparation may be incorporated into a particle such as a microparticle. Microparticles can be produced by spray-drying, lyophilisation, evaporation, fluid bed drying, vacuum drying, or a combination of these methods.

Pharmaceutical Compositions

The present invention also provides pharmaceutical compositions comprising the nucleic acid or conjugated nucleic acid of the invention. The pharmaceutical compositions may be used as medicaments or as diagnostic agents, alone or in combination with other agents. For example, a nucleic acid or conjugated nucleic acid of the invention can be combined with a delivery vehicle (e.g., liposomes) and excipients, such as carriers, diluents. Other agents such as preservatives and stabilizers can also be added. Methods for the delivery of a nucleic acid or conjugated nucleic acid are known in the art and within the knowledge of the person skilled in the art.

The nucleic acid or conjugated nucleic acid of the present invention can also be administered in combination with other therapeutic compounds, either administrated separately or simultaneously, e.g., as a combined unit dose. The invention also includes a pharmaceutical composition comprising a nucleic acid or conjugated nucleic acid according to the present invention in a physiologically/pharmaceutically acceptable excipient, such as a stabilizer, preservative, diluent, buffer, and the like.

The pharmaceutical composition may be specially formulated for administration in solid or liquid form. The composition may be formulated for oral administration, parenteral administration (including, for example, subcutaneous, intramuscular, intravenous, or epidural injection), topical application, intravaginal or intrarectal administration, sublingual administration, ocular administration, transdermal administration, or nasal administration. Delivery using subcutaneous or intravenous methods are preferred.

Dosage

Dosage levels for the medicament and pharmaceutical compositions of the invention can be determined by those skilled in the art by routine experimentation. In one embodiment, a unit dose may contain between about 0.01 mg/kg and about 100 mg/kg body weight of nucleic acid. Alternatively, the dose can be from 10 mg/kg to 25 mg/kg body weight, or 1 mg/kg to 10 mg/kg body weight, or 0.05 mg/kg to 5 mg/kg body weight, or 0.1 mg/kg to 5 mg/kg body weight, or 0.1 mg/kg to 1 mg/kg body weight, or 0.1 mg/kg to 0.5 mg/kg body weight, or 0.5 mg/kg to 1 mg/kg body weight. Dosage levels may also be calculated via other parameters such as, e.g., body surface area.

The pharmaceutical composition may be a sterile injectable aqueous suspension or solution, or in a lyophilized form. In one embodiment, the pharmaceutical composition may comprise lyophilized lipoplexes or an aqueous suspension of lipoplexes. The lipoplexes preferably comprises a nucleic acid of the present invention. Such lipoplexes may be used to deliver the nucleic acid of the invention to a target cell either in vitro or in vivo.

The pharmaceutical compositions and medicaments of the present invention may be administered to a mammalian subject in a pharmaceutically effective dose. The mammal may be selected from humans, dogs, cats, horses, cattle, pig, goat, sheep, mouse, rat, hamster and guinea pig.

Medical Use

A further aspect of the invention relates to a nucleic acid or conjugated nucleic acid of the invention or the pharmaceutical composition comprising the nucleic acid or conjugated nucleic acid of the invention for use in the treatment or prevention of a disease or disorder. The invention includes a pharmaceutical composition comprising one or more RNAi molecules according to the present invention in a physiologically/pharmaceutically acceptable excipient, such as a stabiliser, preservative, diluent, buffer and the like. The nucleic acids or conjugated nucleic acids of the invention or the pharmaceutical compositions comprising a nucleic acid or conjugated nucleic acid of the invention are preferably for use in the treatment or prevention of a disease or disorder for which it is desirable to reduce the expression level of the target gene targeted by the nucleic acid of the invention.

The pharmaceutical composition may be a sterile injectable aqueous suspension or solution, or in a lyophilised form.

Pharmaceutical Combinations

Pharmaceutically acceptable compositions may comprise a therapeutically-effective amount of one or more nucleic acid(s) in any embodiment according to the invention, taken alone or formulated with one or more pharmaceutically acceptable carriers, excipient and/or diluents.

Examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatine; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerine, sorbitol, mannitol and polyethylene glycol; (12) esters, such as ethyl oleate and ethyl laurate; (13) agar; (14) buffering agents, such as magnesium hydroxide and aluminium hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

Stabilisers may be agents that stabilise the nucleic acid agent, for example a protein that can complex with the nucleic acid, chelators (e.g. EDTA), salts, RNAse inhibitors, and DNAse inhibitors.

In some cases it is desirable to slow the absorption of the drug from subcutaneous or intramuscular injection in order to prolong the effect of a drug. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Inhibition

The nucleic acid described herein may be capable of inhibiting the expression of a target gene in a cell. The nucleic acid described herein may be capable of partially inhibiting the expression of a target gene in a cell. Inhibition may be complete, i.e. 0% of the expression level of target gene expression in the absence of the nucleic acid of the invention. Inhibition of target gene expression may be partial, i.e. it may be 15%, 20%, 30%, 40%, 50%, 60%, 70%, 75%, 80%, 85%, 90%, 95% of target gene expression in the absence of a nucleic acid of the invention. Inhibition may last 4 weeks, 5 weeks, 6 weeks, 7 weeks, 8 weeks, 10 weeks, 11 weeks, 12 weeks, 13 weeks, 14 weeks or up to 3 months, when used in a subject, such as a human subject. The nucleic acid or composition comprising the nucleic acid composition may be for use once, every week, every two weeks, every three weeks, every four weeks, every five weeks, every six weeks, every seven weeks, or every eight weeks. The nucleic acid may be for use subcutaneously, intravenously or using any other application routes such as oral, rectal or intraperitoneal.

The expression may be measured in the cells to which the nucleic acid is applied. Alternatively, especially if the nucleic acid is administered to a subject, the level can be measured in a different group of cells or a tissue or an organ or in a body fluid such as blood or plasma or lymph. The level of inhibition is preferably measured in conditions that have been chosen because they show the greatest effect of the nucleic acid on the target mRNA level in cells treated with the nucleic acid in vitro. The level of inhibition may for example be measured after 24 hours or 48 hours of treatment with a nucleic acid of the invention at a concentration of between 0.038 nM-10 μM, preferably 1 nm, 10 nm or 100 nm. These conditions may be different for different nucleic acid sequences or different types of nucleic acids, such as for nucleic acids that are unmodified or modified or conjugated to a ligand or not. Examples of suitable conditions for determining levels of inhibition are described in the examples.

In cells and/or subjects treated with or receiving the nucleic acid of the present invention, the target gene expression may be inhibited compared to untreated cells and/or subjects by at least about 30%, 35%, 40%, 45%, 50%, 55%, 60%, 65%, 70%, 75%, 80%, 85%, 90%, 95%, 98%, or 100%. The level of inhibition may allow treatment of a disease associated with target gene expression or overexpression, or may allow further investigation into the functions of the target gene product.

Target Gene

The target gene may be TMPRSS6, ALDH2, LPA, Factor VII, Eg5, PCSK9, TPX2, apoB, SAA, TTR, RSV, PDGF beta gene, Erb-B gene, Src gene, CRK gene, GRB2 gene, RAS gene, MEKK gene, JNK gene, RAF gene, Erkl/2 gene, PCNA(p21) gene, MYB gene, JU gene, FOS gene, BCL-2 gene, hepcidin, Activated Protein C, Cyclin D gene, VEGF gene, EGFR gene, Cyclin A gene, Cyclin E gene, WNT-1 gene, beta-catenin gene, c-MET gene, PKC gene, NFKB gene, STAT3 gene, survivin gene, Her2/Neu gene, topoisomerase I gene, topoisomerase II alpha gene, mutations in the p73 gene, mutations in the p21(WAF I/CIPI) gene, mutations in the p27(KIPI) gene, mutations in the PPM ID gene, mutations in the RAS gene, mutations in the caveolin I gene, mutations in the MIB I gene, mutations in the MTAI gene, mutations in the M68 gene, mutations in tumor suppressor genes, and mutations in the p53 tumor suppressor gene.

In one embodiment, the target gene is TMPRSS6.

In one embodiment, the target gene is TMPRSS6 and the first strand comprises:

```
(SEQ ID NO: 68)
(vp)-UACCAGAAGAAGCAGGUGA
```

and/or (preferably and the second strand comprises

```
(SEQ ID NO: 69)
UCACCUGCUUCUUCUGGUA.
```

In another embodiment, the target gene is TMPRSS6 and the first strand comprises:

```
(SEQ ID NO: 9)
(vp)-mU fA mC fC mA fG mA fA mG fA mA fG mC fA mG
fG mU (ps) fG (ps) mA
```

and/or (preferably and) the second strand comprises

```
(SEQ ID NO: 70)
fU (ps) mC (ps) fA mC fC mU fG mC fU mU fC mU fU
mC fU mG fG (ps) mU (ps) fA
```

wherein mA, mU, mC, and mG each represent 2'-OMe RNA; fA, fU, fC and fG each represent 2'-deoxy-2'-F RNA; (ps) represents a phosphorothioate linkage; and (vp)-mU represents a (E)-vinylphosphonate mU.

In another embodiment, the target gene is not TMPRSS6.

In one embodiment, the target gene is TTR.

In one embodiment, the target gene is TTR and the first strand comprises:

```
(SEQ ID NO: 71)
(vp)-UUAUAGAGCAAGAACACUGUU
```

and/or (preferably and) the second strand comprises

```
(SEQ ID NO: 72)
AACAGUGUUCUUGCUCUAUAA.
```

In another embodiment, the target gene is TTR and the first strand comprises:

```
(SEQ ID NO: 3)
(vp)-mUfUmAfUmAfGmAfGmCfAmAfGmAfAmCfAmCfUmG(ps)fU
(ps)mU
```

and/or (preferably and) the second strand comprises

```
(SEQ ID NO: 73)
fA(ps)mA(ps)fCmAfGmUfGmUfUmCfUmUfGmCfUmCfUmAfU(ps)
mA(ps)fA
```

wherein mA, mU, mC, and mG each represent 2'-OMe RNA; fA, fU, fC and fG each represent 2'-deoxy-2'-F RNA;

(ps) represents a phosphorothioate linkage; and (vp)-mU represents a (E)-vinylphosphonate mU.

In one embodiment, the target gene is ALDH2.

In one embodiment, the target gene is ALDH2 and the first strand comprises:

```
(SEQ ID NO: 74)
(vp)-UCUUCUUAAACUGAGUUUC
```

and/or (preferably and) the second strand comprises

```
(SEQ ID NO: 75)
GAAACUCAGUUUAAGAAGA.
```

In another embodiment, the target gene is ALDH2 and the first strand comprises:

```
(SEQ ID NO: 19)
(vp)-mUfCmUfUmCfUmUfAmAfAmCfUmGfAmGfUmU(ps)fU(ps)mC
```

and/or (preferably and) the second strand comprises

```
(SEQ ID NO: 76)
mG(ps)mA(ps)mAmAmCmUfCfAfGmUmUmUmAmAmGmAmA(ps)mG
(ps)mA
```

wherein mA, mU, mC, and mG each represent 2'-OMe RNA; fA, fU, fC and fG each represent 2'-deoxy-2'-F RNA; (ps) represents a phosphorothioate linkage; and (vp)-mU represents a (E)-vinylphosphonate mU.

In another embodiment, the target gene is ALDH2 and the first strand comprises:

```
(SEQ ID NO: 19)
(vp)-mUfCmUfUmCfUmUfAmAfAmCfUmGfAmGfUmU(ps)fU(ps)
mC
```

and/or (preferably and) the second strand comprises

```
(SEQ ID NO: 77)
fG(ps)mA(ps)fAmAfCmUfCmAfGmUfUmUfAmAfGmAfA(ps)mG
(ps)fA
```

wherein mA, mU, mC, and mG each represent 2'-OMe RNA; fA, fU, fC and fG each represent 2'-deoxy-2'-F RNA; (ps) represents a phosphorothioate linkage; and (vp)-mU represents a (E)-vinylphosphonate mU.

In one embodiment, the target gene is a gene other than: LPA and/or a complement component gene (genes that encode proteins of the immune system's complement system or pathway) and/or ALDH2 and/or TMPRSS6, and/or TTR.

Swiss

A further aspect of the invention relates to nucleic acid of the invention in the manufacture of a medicament for treating or preventing a disease or disorder.

Method of Treatment

Also included in the invention is a method of treating or preventing a disease or disorder comprising administration of a pharmaceutical composition comprising a nucleic acid or conjugated nucleic acid as described herein, to an individual in need of treatment. The nucleic acid composition may be administered twice every week, once every week, every two weeks, every three weeks, every four weeks, every five weeks, every six weeks, every seven weeks, or every eight weeks. The nucleic acid or conjugated nucleic acid may be administered to the subject subcutaneously, intravenously or using any other application routes such as oral, rectal or intraperitoneal.

In one embodiment, a subject is administered an initial dose and one or more maintenance doses of a nucleic acid agent. The maintenance dose or doses can be the same or lower than the initial dose, e.g., one-half less of the initial dose. The maintenance doses are, for example, administered no more than once every 2, 5, 10, or 30 days. The treatment regimen may last for a period of time which will vary depending upon the nature of the particular disease, its severity and the overall condition of the patient.

Combinations

In one embodiment, the composition includes a plurality of nucleic acid agent species. In another embodiment, the nucleic acid agent species has sequences that are non-overlapping and non-adjacent to another species with respect to a naturally occurring target sequence. In another embodiment, the plurality of nucleic acid agent species is specific for different naturally occurring target genes. In another embodiment, the nucleic acid agent is allele specific.

The nucleic acid or conjugated nucleic acid of the present invention can also be administered or for use in combination with other therapeutic compounds, either administered separately or simultaneously, e.g. as a combined unit dose.

Methods of Manufacture

The nucleic acid or conjugated nucleic acid of the present invention can be produced using routine methods in the art including chemically synthesis or expressing the nucleic acid either in vitro (e.g., run off transcription) or in vivo. For example, using solid phase chemical synthesis or using an expression vector. In one embodiment, the expression vector can produce the nucleic acid of the invention in a target cell. Methods for the synthesis of the nucleic acid described herein are known to persons skilled in the art.

Statements

Some aspects of the invention are defined by the following statements:

1. A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited, wherein the first strand has a terminal 5' (E)-vinylphosphonate nucleotide, characterised in that the terminal 5' (E)-vinylphosphonate nucleotide is linked to the second nucleotide in the first strand by a phosphodiester linkage.

2. A nucleic acid according to statement 1, wherein the first strand includes more than 1 phosphodiester linkage.

3. A nucleic acid according to statement 2, wherein the first strand comprises phosphodiester linkages between at least the terminal three 5' nucleotides.

4. A nucleic acid according to statement 3, wherein the first strand comprises phosphodiester linkages between at least the terminal four 5' nucleotides.

5. A nucleic acid according to statement 3, wherein the first strand comprises formula (Ia):

$$(vp)\text{-}N(po)[N(po)]_n \quad \text{(Ia)}$$

where '(vp)-' is the 5' (E)-vinylphosphonate, 'N' is a nucleotide, 'po' is a phosphodiester linkage, and n is from 1 to (the total number of nucleotides in the first strand—2), preferably wherein n is from 1 to (the total number of nucleotides in the first strand—3), more preferably wherein n is from 1 to (the total number of nucleotides in the first strand—4).

6. A nucleic acid according to any of statements 1 to 5, wherein the first strand includes at least one phosphorothioate (ps) linkage.

7. A nucleic acid according to statement 6, wherein the first strand further comprises a phosphorothioate linkage between the terminal two 3' nucleotides or phosphorothioate linkages between the terminal three 3' nucleotides.

8. A nucleic acid according to statement 7, wherein the linkages between the other nucleotides in the first strand are phosphodiester linkages.

9. A nucleic acid according to statement 6, wherein the first strand includes more than 1 phosphorothioate linkage.

10. A nucleic acid according to statements 1-9, wherein the second strand comprises a phosphorothioate linkage between the terminal two 3' nucleotides or phosphorothioate linkages between the terminal three 3' nucleotides.

11. A nucleic acid according to statements 1-10, wherein the second strand comprises a phosphorothioate linkage between the terminal two 5' nucleotides or phosphorothioate linkages between the terminal three 5' nucleotides.

12. A nucleic acid according to any one of the preceding statements, wherein the terminal 5' (E)-vinylphosphonate nucleotide is an RNA nucleotide.

13. A nucleic acid of any preceding statements, wherein the first strand of the nucleic acid has a length in the range of 15-30 nucleotides.

14. A nucleic acid according to statement 13, wherein the first strand of the nucleic acid has a length in the range of 19-25 nucleotides.

15. A nucleic acid of any preceding statements, wherein the second strand of the nucleic acid has a length in the range of 15-30 nucleotides.

16. A nucleic acid according to statement 15, wherein the second strand of the nucleic acid has a length in the range of 19-25 nucleotides.

17. A nucleic acid of any preceding statement, which is blunt ended at both ends.

18. A nucleic acid according to any preceding statements, wherein one or more nucleotides on the first strand is modified, to form modified nucleotides.

19. A nucleic acid according to statement 18, wherein one or more nucleotides on the second strand is modified, to form modified nucleotides.

20. A nucleic acid according to statements 18 or 19, wherein the modification is a modification at the 2'—OH group of the ribose sugar, optionally selected from 2'-OMe or 2'-F modifications.

21. A nucleic acid according to statements 18-20, wherein one or more of the odd numbered nucleotides of the first strand is a modified nucleotide having a first modification at the 2'OH group of the ribose sugar and one or more of the even numbered nucleotides of the first strand is a differently modified nucleotide having a second modification at the 2' OH group of the ribose sugar, where the first and second modifications are different.

22. A nucleic acid according to statement 21, wherein the first modification is a 2'-OMe and the second modification is a 2'-F, or vice versa.

23. A nucleic acid according to any preceding statements, wherein there are no 2'-methoxyethyl modified nucleotides in the first strand.

24. A nucleic acid according to any preceding statements, wherein the target gene is TMPRSS6.

25. A nucleic acid according to statement 24, wherein the first strand comprises

```
                                        (SEQ ID NO: 68)
              (vp)-UACCAGAAGAAGCAGGUGA
```

and/or (preferably and) the second strand comprises

```
                                        (SEQ ID NO: 69)
               UCACCUGCUUCUUCUGGUA.
```

26. A nucleic acid according to statement 25, wherein the first strand comprises

```
                                         (SEQ ID NO: 9)
(vp)-mU fA mC fC mA fG mA fA mG fA mA fG mC fA mG
fG mU (ps) fG (ps) mA
```

and/or (preferably and) the second strand comprises

```
                                        (SEQ ID NO: 70)
fU (ps) mC (ps) fA mC fC mU fG mC fU mU fC mU fU
mC fU mG fG (ps) mU (ps) fA
```

wherein mA, mU, mC, and mG each represent 2'-OMe RNA; fA, fU, fC and fG each represent 2'-deoxy-2'-F RNA; (ps) represents a phosphorothioate linkage; and (vp)-mU represents a (E)-vinylphosphonate mU.

27. A conjugate for inhibiting expression of a target gene in a cell, said conjugate comprising a nucleic acid portion and ligand portion, said nucleic acid portion comprising a nucleic acid as defined in any one of statements 1-26.

28. A conjugate according to statement 27, wherein the second strand of the nucleic acid is conjugated to the ligand portion.

29. A conjugate according to any one of statements 27 or 28, wherein the ligand portion comprises one or more GalNAc ligands and derivatives thereof, such as comprising a GalNAc moiety at the 5' end of the second strand of the nucleic acid.

30. A conjugate according to any one of statements 27-29, wherein the ligand portion comprises a linker moiety and a targeting ligand, and wherein the linker moiety links the targeting ligand to the nucleic acid portion.

31 A conjugate according to statement 30, wherein the linker moiety is a serinol-derived linker moiety, and the targeting ligand is conjugated exclusively to the 3' and/or 5' ends of one or both of the first and second strands of the nucleic acid, wherein the 5' end of the first strand is not conjugated, wherein:

(i) the second strand is conjugated at the 5' end to the targeting ligand, and wherein (a) the second strand is also conjugated at the 3' end to the targeting ligand and the 3' end of the first strand is not conjugated; or (b) the first strand is conjugated at the 3' end to the targeting ligand and the 3' end of the second strand is not conjugated; or (c) both the second strand and the first strand are also conjugated at the 3' ends to the targeting ligand; or (ii) both the second strand and the first strand are conjugated at the 3' ends to the targeting ligand and the 5' end of the second strand is not conjugated; and (iii) wherein said first strand includes modified nucleotides at a plurality of positions, and wherein the nucleotides at positions 2 and 14 from the 5' end of the first strand are not modified with a 2'-OMe modification.

32. A conjugate of statement 31 wherein the nucleotides at positions 2 and 14 from the 5' end of the first strand are modified.

33. A conjugate according to statement 32, wherein the nucleotides at positions 2 and 14 from the 5' end of the first strand are not modified with a 2'-OMe modification, and the nucleotide on the second strand which corresponds to position 13 of the first strand is not modified with a 2'-OMe modification.

34. A conjugate according to statements 32, wherein the nucleotides at positions 2 and 14 from the 5' end of the first strand are not modified with a 2'-OMe modification, and the nucleotide on the second strand which corresponds to position 11 of the first strand is not modified with a 2'-OMe modification.

35. A conjugate according to statements 32-34 wherein the nucleotides at positions 2 and 14 from the 5' end of the first strand are not modified with a 2'-OMe modification, and the nucleotides on the second strand which corresponds to position 11 and 13 of the first strand are not modified with a 2'-OMe modification.

36. A conjugate of any statements 31-35 wherein the nucleotides on the second strand corresponding to positions 11 and/or 13 from the 5' end of the first strand are modified.

37 A conjugate according to statements 32-36, wherein the nucleotides at positions 2 and 14 from the 5' end of the first strand are not modified with a 2'-OMe modification, and the nucleotides on the second strand which correspond to position 11, or 13, or 11 and 13, or 11-13 of the first strand are modified with a 2' fluoro modification.

38 A conjugate according to any one of statements 32-37, wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are not modified with a 2'-OMe modification.

39 A conjugate according to any of statements 32-38 wherein the nucleotides at positions 2 and 14 from the 5' end of the first strand are modified with a 2' fluoro modification, and the nucleotides on the second strand which correspond to position 11, or 13, or 11 and 13, or 11-13 of the first strand are modified with a 2' fluoro modification.

40 A conjugate according to any one of statements 31-39 wherein greater than 50% of the nucleotides of the first and/or second strand comprise a 2'-OMe modification, such as greater than 55%, 60%, 65%, 70%, 75%, 80%, or 85%, or more, of the first and/or second strand comprise a 2'-OMe modification, preferably measured as a percentage of the total nucleotides of both the first and second strands.

41 A conjugate according to any one of statements 31-40 comprising no more than 20%, (such as no more than 15% or no more than 10%) of 2' fluoro modifications on the first and/or second strand, as a percentage of the total nucleotides of both strands.

42 A conjugate according to any one of statements 31-42 wherein the terminal nucleotide at the 3' end of at least one of the first strand and the second strand is an inverted nucleotide and is attached to the adjacent nucleotide via the 3' carbon of the terminal nucleotide and the 3' carbon of the adjacent nucleotide and/or the terminal nucleotide at the 5' end of at least one of the first strand and the second strand is an inverted nucleotide and is attached to the adjacent nucleotide via the 5' carbon of the terminal nucleotide and the 5' carbon of the adjacent nucleotide, or wherein the nucleic acid comprises a phosphorodithioatelinkage.

43 The conjugate according to statements 31-42 wherein the second strand is conjugated at the 5' end to the targeting ligand, the second strand is also conjugated at the 3' end to the targeting ligand and the 3' end of the first strand is not conjugated.

44. The conjugate according to statements 31-42 wherein the second strand is conjugated at the 5' end to the targeting ligand, the first strand is conjugated at the 3' end to the targeting ligand and the 3' end of the second strand is not conjugated.

45. The conjugate according to statements 31-42 wherein the second strand is conjugated at the 5' end to the targeting ligand and both the second strand and the first strand are also conjugated at the 3' ends to the targeting ligand.

46. The conjugate according to statements 31-42 wherein both the second strand and the first strand are conjugated at the 3' ends to the targeting ligand and the 5' end of the second strand is not conjugated.

47. The conjugate according to any one of statements 31-46 wherein the ligands are monomeric ligands.

48. The conjugate according to any one of statements 31-47 wherein the conjugated strands are conjugated to a targeting ligand via a serinol-derived linker moiety including a further linker wherein the further linker is or comprises a saturated, unbranched or branched $C_{1-15}$ alkyl chain, wherein optionally one or more carbons (for example 1, 2 or 3 carbons, suitably 1 or 2, in particular 1) is/are replaced by a heteroatom selected from O, N, $S(O)_p$ wherein p is 0, 1 or 2, (for example a $CH_2$ group is replaced with 0, or with NH, or with S, or with $SO_2$ or a —$CH_3$ group at the terminus of the chain or on a branch is replaced with OH or with $NH_2$) wherein said chain is optionally substituted by one or more oxo groups (for example 1 to 3, such as 1 group).

49. The conjugate according to statement 48 wherein the further linker comprises a saturated, unbranched $C_{1-15}$ alkyl chain wherein one or more carbons (for example 1, 2 or 3 carbons, suitably 1 or 2, in particular 1) is/are replaced by an oxygen atom.

50. The conjugate according to statement 49 wherein the further linker comprises a PEG-chain.

51. The conjugate according to statement 48 wherein the further linker comprises a saturated, unbranched $C_{1-15}$ alkyl chain.

52. The conjugate according to statement 51 wherein the further linker comprises a saturated, unbranched $C_{1-6}$ alkyl chain.

53. The conjugate according to statement 52 wherein the further linker comprises a saturated, unbranched $C_4$ or C alkyl chain, e.g. a $C_4$ alkyl chain.

54. The conjugate according to statements 31-42 wherein the first strand is a compound of formula (XXV):

(XXV)

wherein b is 0 or 1; and the second strand is a compound of formula (XXVI):

(XXVI)

wherein c and d are independently 0 or 1;

wherein:

$Z_1$ and $Z_2$ are the the first and second strands respectively;

Y is O or S;

$R_1$ is H or methyl;

n is 0, 1, 2 or 3; and L is the same or different in formulae (XXV) and (XXVI) and is selected from the group consisting of:

—$(CH_2)_q$, wherein q=2-12;

—$(CH_2)_r$—C(O)—, wherein r=2-12;

—$(CH_2$—$CH_2$—$O)_s$—$CH_2$—C(O)—, wherein s=1-5;

—$(CH_2)_t$—CO—NH—$(CH_2)_t$—NH—C(O)—, wherein t is independently is 1-5;

—$(CH_2)_u$—CO—NH—$(CH_2)$, —C(O)—, wherein u is independently is 1-5; and

—$(CH_2)_v$—NH—C(O)—, wherein v is 2-12; and wherein the terminal C(O) (if present) is attached to the NH group;

and wherein b+c+d is 2 or 3.

55. The conjugate according to statement 54 wherein b is 0, c is 1 and d is 1.

56. The conjugate according to statement 54 wherein b is 1, c is 0 and d is 1.

57. The conjugate according to statement 54 wherein b is 1, c is 1 and d is 0.

58. The conjugate according to statement 54 wherein b is 1, c is 1 and d is 1.

59. The conjugate according to any one of statements 54-58 wherein Y is O.

60. The conjugate according to any one of statements 54-58 wherein Y is S.

61. The conjugate according to any one of statements 54-60 wherein $R_1$ is H.

62. The conjugate according to any one of statements 54-60 wherein $R_1$ is methyl.

63. The conjugate according to any one of statements 54-62 wherein n is 0.

64. The conjugate according to any one of statements 51-63 wherein L is —$(CH_2)_r$—C(O)—, wherein r=2-12.

65. The conjugate according to statement 64 wherein r=2-6.

66. The conjugate according to statement 65 wherein r=4 or 6 e.g. 4.

67 A conjugate for inhibiting expression of a TMPRSS6 gene in a cell, comprising a first strand comprising

```
                                       (SEQ ID NO: 9)
(vp)-mU fA mC fC mA fG mA fA mG fA mA fG mC fA mG
fG mU (ps) fG (ps) mA
```

and/or (preferably and) the second strand comprises

```
                                      (SEQ ID NO: 10)
Ser(GN) (ps) fU (ps) mC (ps) fA mC fC mU fG mC fU
mU fC mU fU mC fU mG fG (ps) mU (ps) fA (ps)
Ser(GN)
```

wherein mA, mU, mC, and mG each represent 2'-OMe RNA; fA, fU, fC and fG each represent 2'-deoxy-2'-F RNA; (ps) represents a phosphorothioate linkage; (vp)-mU represents a (E)-vinylphosphonate mU and Ser(GN) represents a GalNAc-C4 targeting ligand attached to serinol-derived linker moiety.

68. A composition comprising a nucleic acid of any of statements 1-26 or conjugate of any of statements 27-67 and a physiologically acceptable excipient.

69. A nucleic acid of any of statements 1-26 or conjugate of any of statements 27-67 or composition according to statement 68 for use in the treatment of a disease or disorder.

EXAMPLES

Figure 1:
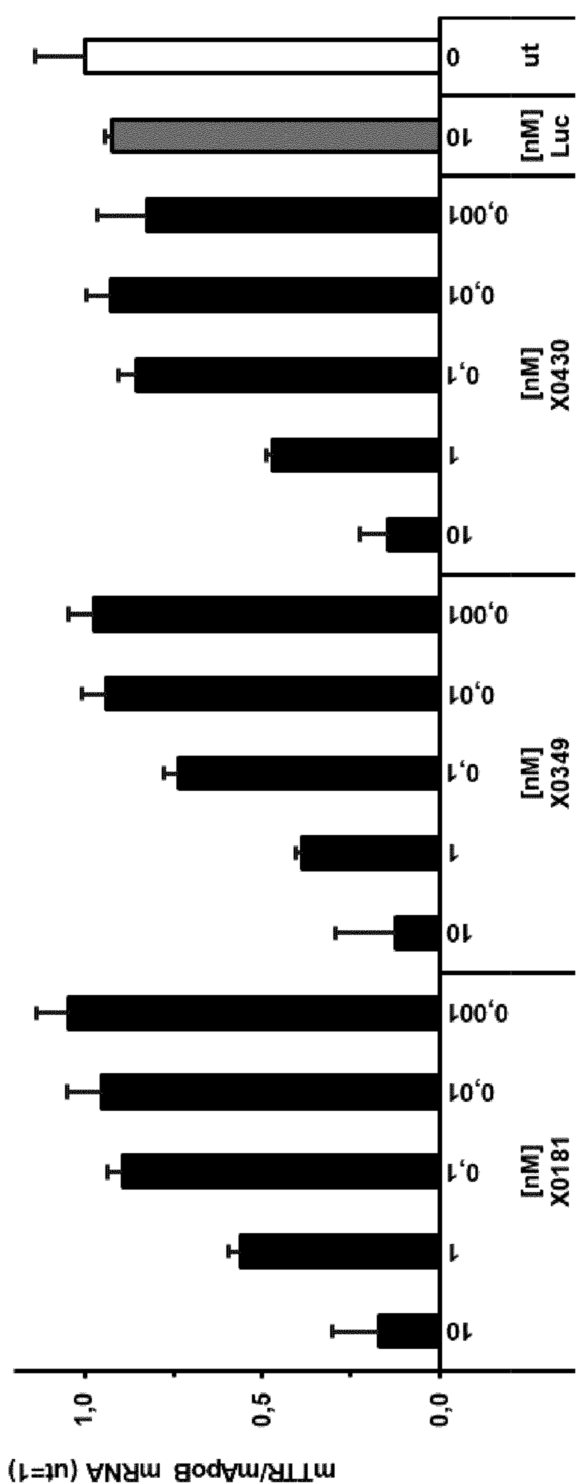
FIG. 1—GalNAc siRNA conjugates with vinylphosphonate at the 5' end of the first strand and phosphodiester internucleotide linkages at the 5' end of the first strand effect improved reduction of TTR target mRNA levels in vitro.

Herein we show examples of GalNAc siRNA conjugates which are modified with (E)-vinylphosphonate (VP) at the 5' end of the first strand and, in addition to that, contain either phosphorothioate (PS) internucleotide linkages or phosphodiester internucleotide linkages between the first, second and third nucleotide at the 5' end of the first strand. In context of siRNA conjugates with each one serinol-linked GalNAc moiety at the 5' end and at the 3' end of the second strand, siRNA conjugates with either (I) PS, or (II) VP without PS, or (III) VP with PS at the 5' end of the first strand are equally stable when incubated with acidic tritosome lysate. However, we show better dose response for target gene knockdown with GalNAc siRNA conjugates with VP and without PS at the 5' end of the first strand.

Material & Methods

Primers:

| | | |
|---|---|---|
| TTR | fw | TGGACACCAAATCGTACTGGAA |
| | rev | CAGAGTCGTTGGCTGTGAAAAC |
| | probe | BHQ1-ACTTGGCATTTCCCCGTTCCATGAATT-FAM |
| TMPRSS6 | fw | CCGCCAAAGCCCAGAAG |
| | rev | GGTCCCTCCCCAAAGGAATAG |
| | probe | BHQ1-CAGCACCCGCCTGGGAACTTACTACAAC-FAM |
| ALDH2 | fw | GGCAAGCCTTATGTCATCTCGT |
| | rev | GGAATGGTTTTCCCATGGTACTT |
| | probe | BHQ1-TGAAATGTCTCCGCTATTACGCTGGCTG-FAM |
| ApoB | fw | AAAGAGGCCAGTCAAGCTGTTC |
| | rev | GGTGGGATCACTTCTGTTTTGG |
| | probe | BHQ1-CAGCAACACACTGCATCTGGTCTCTACCA-VIC |
| PTEN | fw | CACCGCCAAATTTAACTGCAGA |
| | rev | AAGGGTTTGATAAGTTCTAGCTGT |
| | probe | BHQ1-TGCACAGTATCCTTTTGAAGACCATAACCCA-VIC |

Cell Culture

Primary murine hepatocytes (Thermo Scientific: GIBCO Lot: #MC798) were thawn and cryo-preservation medium exchanged for Williams E medium supplemented with 5% FBS, 1 μM dexamethasone, 2 mM GlutaMax, 1% PenStrep, 4 mg/ml human recombinant insulin, 15 mM Hepes. Cell density was adjusted to 250,000 cells per 1 ml. 100 μl per well of this cell suspension were seeded into collagen pre-coated 96 well plates. The test article was prediluted in the same medium (5 times concentrated) for each concentration and 25 μl of this prediluted siRNA or medium only were added to the cells. Cells were cultured in at 37° C. and 5% $CO_2$. 24 h post treatment the supernatant was discarded, and cells were washed in cold PBS and 250 μl RNA-Lysis Buffer S (Stratec) was added. Following 15 min incubation at room temperature plates were storage at −80° C. until RNA isolation according to the manufacturer's protocol.

TaqMan Analysis

For mTTR & ApoB MultiPlex TaqMan analysis 10 μl isolated RNA for each treatment group were mixed with 10

μl PCR mastermix (TAKYON low Rox) containing 600 nM mTTR-primer, 400 nM ApoB-primer and 200 nM of each probe as well as 0.5 units Euroscript II RT polymerase with 0.2 units RNAse inhibitor. TaqMan analysis was performed in 384-well plate with a 10 min RT step at 48° C., 3 min initial denaturation at 95° C. and 40 cycles of 95° C. for 10 s and 60° C. for 1 min.

For TMPRSS6 & ApoB MultiPlex TaqMan analysis 10 μl isolated RNA for each treatment group were mixed with 10 μl PCR mastermix (TAKYON low Rox) containing 800 nM TMPRSS6 primer, 100 nM ApoB primer and 200 nM of either probe as well as 0.5 units Euroscript II RT polymerase with 0.2 units RNAse inhibitor. TaqMan analysis was performed in 384-well plate with a 10 min reverse transcription step at 48° C., 3 min initial denaturation at 95° C. and 40 cycles of 95° C. for 10 s and 60° C. for 1 min.

Tritosome Stability Assay

To probe for RNAase stability in the endosomal/lysosomal compartment of hepatic cells in vitro siRNA was incubated for 0 h, 4 h, 24 h or 72 h in Sprague Dawley Rat Liver Tritosomes (Tebu-Bio, CatN.: R0610.LT, lot: 1610405, pH: 7.4, 2.827 Units/ml). To mimic the acidified environment the Tritosomes were mixed 1:10 with low pH buffer (1.5 M acetic acid, 1.5 M sodium acetate pH 4.75). 30 μl of this acidified Tritosomes Following 10 μl siRNA (20 μM) were mixed with and incubated for the indicated times at 37° C. Following incubation RNA was isolated with the Clarity OTX Starter Kit-Cartridges (Phenomenex CatNo: KSO-8494) according to the manufacturer's protocol for biological fluids. Lyophilized RNA was reconstituted in 30 μl $H_2O$, mixed with 4× loading buffer and 5 μl were loaded to a 20% TBE-polyacrylamide gel electrophoresis (PAGE) for separation qualitative semi-quantitative analysis. PAGE was run at 120 V for 2 h and RNA visualized by Ethidium-bromide staining with subsequent digital imaging with a Biorad Imaging system.

Sequences

| Duplex | Strand | Sequence (A first strand; B, second strand, both 5'-3') |
|---|---|---|
| X0181 | X0181A | mU(ps)fU(ps)mAfUmAfGmAfGmCfAmAfGmAfAmCfAmCfUmG(ps)fU(ps)mU |
| | X0181B | Ser(GN)(ps)fA(ps)mA(ps)fCmAfGmUfGmUfUmCfUmUfGmCfUmCfUmAfU(ps)mA(ps)fA(ps)Ser(GN) |
| X0349 | X0349A | (vp)-mUfUmAfUmAfGmAfGmCfAmAfGmAfAmCfAmCfUmG(ps)fU(ps)mU |
| | X0349B | Ser(GN)(ps)fA(ps)mA(ps)fCmAfGmUfGmUfUmCfUmUfGmCfUmCfUmAfU(ps)mA(ps)fA(ps)Ser(GN) |
| X0430 | X0430A | (vp)-mU(ps)fU(ps)mAfUmAfGmAfGmCfAmAfGmAfAmCfAmCfUmG(ps)fU(ps)mU |
| | X0430B | Ser(GN)(ps)fA(ps)mA(ps)fCmAfGmUfGmUfUmCfUmUfGmCfUmCfUmAfU(ps)mA(ps)fA(ps)Ser(GN) |
| X0322 | X0322A | mA(ps)fA(ps)mCfCmAfGmAfAmGfAmAfGmCfAmGfGmU(ps)fG(ps)mA |
| | X0322B | Ser(GN)(ps)fU(ps)mC(ps)fAmCfCmUfGmCfUmUfCmUfUmCfUmGfG(ps)mU(ps)fU(ps)Ser(GN) |
| X0365 | X0365A | (vp)-mUfAmCfCmAfGmAfAmGfAmAfGmCfAmGfGmU(ps)fG(ps)mA |
| | X0365B | Ser(GN)(ps)fU(ps)mC(ps)fAmCfCmUfGmCfUmUfCmUfUmCfUmGfG(ps)mU(ps)fA(ps)Ser(GN) |
| X0431 | X0431A | (vp)-mU(ps)fA(ps)mCfCmAfGmAfAmGfAmAfGmCfAmGfGmU(ps)fG(ps)mA |
| | X0431B | Ser(GN)(ps)fU(ps)mC(ps)fAmCfCmUfGmCfUmUfCmUfUmCfUmGfG(ps)mU(ps)fA(ps)Ser(GN) |
| X0319 | X0319A | mA(ps)fA(ps)mUfGmUfUmUfUmCfCmUfGmCfUmGfAmC(ps)fG(ps)mG |
| | X0319B | Ser(GN)(ps)fC(ps)mC(ps)fGmUfCmAfGmCfAmGfGmAfAmAfAmCfA(ps)mU(ps)fU(ps)Ser(GN) |
| X0362 | X0362A | (vp)-mUfAmUfGmUfUmUfUmCfCmUfGmCfUmGfAmC(ps)fG(ps)mG |
| | X0362B | Ser(GN)(ps)fC(ps)mC(ps)fGmUfCmAfGmCfAmGfGmAfAmAfAmCfA(ps)mU(ps)fA(ps)Ser(GN) |
| X0320 | X0320A | mU(ps)fC(ps)mUfUmCfUmUfAmAfAmCfUmGfAmGfUmU(ps)fU(ps)mC |
| | X0320B | Ser(GN)(ps)fG(ps)mA(ps)fAmAfCmUfCmAfGmUfUmUfAmAfGmAfA(ps)mG(ps)fA(ps)Ser(GN) |
| X0363 | X0363A | (vp)-mUfCmUfUmCfUmUfAmAfAmCfUmGfAmGfUmU(ps)fU(ps)mC |
| | X0363B | Ser(GN)(ps)fG(ps)mA(ps)fAmAfCmUfCmAfGmUfUmUfAmAfGmAfA(ps)mG(ps)fA(ps)Ser(GN) |
| X0028 | X0028A | mU(ps)fC(ps)mGfAmAfGmUfAmUfUmCfCmGfCmGfUmA(ps)fC(ps)mG |
| | X0028B | [ST23(ps)]3ST41(ps)fCmGUmAfCmGfCmGfGmAfAmUfAmCfUmUfC(ps)mG(ps)fA |
| X0027 | X0027A | mA(ps)fA(ps)mCfCmAfGmAfAmGfAmAfGmCfAmGfGmU(ps)fG(ps)mA |
| | X0027B | [ST23(ps)]3ST41(ps)fU(ps)mC(ps)fAmCfCmUfGmCfUmUfCmUfUmCfUmGfG(ps)mU(ps)fU |
| X0204 | X0204A | (vp)-mU(ps)fA(ps)mCfCmAfGmAfAmGfAmAfGmCfAmGfGmU(ps)fG(ps)mA |
| | X0204B | [ST23(ps)]3ST41(ps)fUmCfAmCfCmUfGmCfUmUfCmUfUmCfUmGfG(ps)mU(ps)fA |

-continued

| Sequences | | |
|---|---|---|
| Duplex | Strand | Sequence (A first strand; B, second strand, both 5'-3') |
| X0205 | X0205A | (vp)-mUfAmCfCmAfGmAfAmGfAmAfGmCfAmGfGmU(ps)fG(ps)mA |
| | X0205B | [ST23(ps)]3ST41(ps)fUmCfAmCfCmUfGmCfUmUfCmUfUmCfUmGfG(ps)mU (ps)fA |
| X0207 | X0207A | mU(ps)fA(ps)mCfCmAfGmAfAmGfAmAfGmCfAmGfGmU(ps)fG(ps)mA |
| | X0207B | [ST23(ps)]3ST41(ps)fUmCfAmCfCmUfGmCfUmUfCmUfUmCfUmGfG(ps)mU (ps)fA |
| X0477 | X0477A | mU(ps)fC(ps)mUfUmCfUmUfAmAfAmCfUmGfAmGfUmU(ps)fU(ps)mC |
| | X0477B | Ser(GN)(ps)mG(ps)mA(ps)mAmAmCmUfCfAfGmUmUmUmAmAmGmAmA (ps)mG(ps)mA(ps)Ser(GN) |
| X0478 | X0478A | (vp)-mUfCmUfUmCfUmUfAmAfAmCfUmGfAmGfUmU(ps)fU(ps)mC |
| | X0478B | Ser(GN)(ps)mG(ps)mA(ps)mAmAmCmUfCfAfGmUmUmUmAmAmGmAmA (ps)mG(ps)mA(ps)Ser(GN) |

Example 1

GalNAc siRNA conjugates with vinylphosphonate at the 5' end of the first strand and phosphodiester internucleotide linkages at the 5' end of the first strand effect improved reduction of TTR target mRNA levels in vitro.

All tested conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0181 contains two phosphorothioate internucleotide linkages at the 5' end of the first strand. X0430 contains a vinylphosphonate modification at the first nucleotide and two phosphorothioate internucleotide linkages at the 5' end of the first strand. X0349 contains a vinylphosphonate modification at the first nucleotide and no phosphorothioate internucleotide linkages at the 5' end of the first strand. Compared to X0181 and X0430, X0349 shows improved reduction of TTR target gene levels in vitro. “ut” indicates an untreated sample which the other samples were normalised to. “Luc” indicates an siRNA targeting Luciferase (X0028), which was used as non-targeting control and does not reduce target mRNA levels.

The experiment was conducted in mouse primary hepatocytes. 25,000 cells were seeded per 96-well and treated with 0.001-10 nM GalNAc-conjugated siRNA directly after plating. Cells were lysed after 24 h, total RNA was extracted and TTR and ApoB mRNA levels were determined by Taqman qRT-PCR. Each bar represents mean±SD from three technical replicates.

Data are shown in FIG. 1.

Example 2

GalNAc siRNA conjugates with vinylphosphonate at the 5' end of the first strand and phosphodiester internucleotide linkages at the 5' end of the first strand effect improved reduction of TMPRSS6 target mRNA levels in vitro.

All tested conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0322 contains two phosphorothioate internucleotide linkages at the 5' end of the first strand. X0431 contains a vinylphosphonate modification at the first nucleotide and two phosphorothioate internucleotide linkages at the 5' end of the first strand. X0365 contains a vinylphosphonate modification at the first nucleotide and no phosphorothioate internucleotide linkages at the 5' end of the first strand. Compared to X0322 and X0431, X0365 shows improved reduction of TMPRSS6 target gene levels in vitro. “ut” indicates an untreated sample, which the other samples were normalised to. “Luc” indicates an siRNA targeting Luciferase (X0028), which was used as non-targeting control and does not reduce target mRNA levels.

The experiment was conducted in mouse primary hepatocytes. 25,000 cells were seeded per 96-well and treated with 0.01-100 nM GalNAc-conjugated siRNA directly after plating. Cells were lysed after 24 h, total RNA was extracted and TMPRSS6 and ApoB mRNA levels were determined by Taqman qRT-PCR. Each bar represents mean±SD from three technical replicates.

Figure 2:
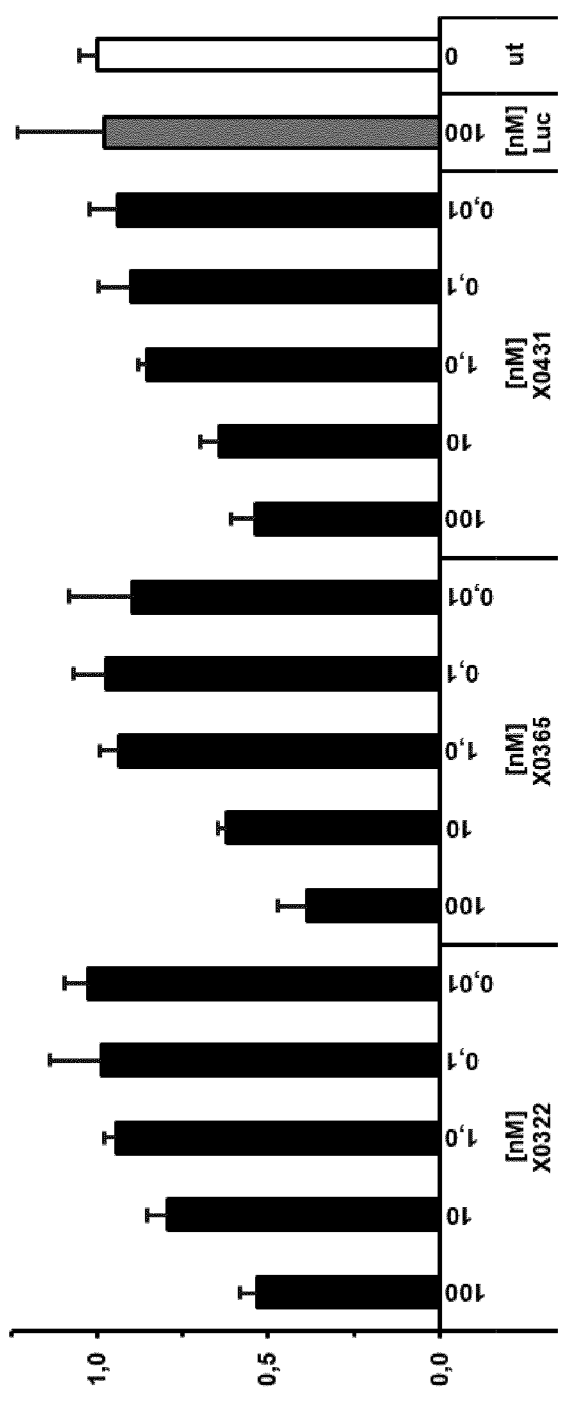
FIG. 2—GalNAc siRNA conjugates with vinylphosphonate at the 5' end of the first strand and phosphodiester internucleotide linkages at the 5' end of the first strand effect improved reduction of TMPRSS6 target mRNA levels in vitro.

Data are shown in FIG. 2.

It is clear from examples 1 and 2 that the presence of a vinylphosphonate at the 5' end of the antisense strand increases the activity of an siRNA. This activity is further increased when the linkages between the first three nucleotides at the 5' end of the first strand are phosphodiester linkages rather than phosphorothioate linkages. This effect is independent of the nucleotide sequence of the siRNAs.

Example 3

GalNAc siRNA conjugates with vinylphosphonate at the 5' end of the first strand and phosphodiester internucleotide linkages at the 5' end of the first strand effect reduction of ALDH2 target mRNA levels in vitro.

All tested conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0319 contains two phosphorothioate internucleotide linkages at the 5' end of the first strand. X0362 contains a vinylphosphonate modification at the first nucleotide and no phosphorothioate internucleotide linkages at the 5' end of the first strand. Both siRNA conjugates reduce ALDH2 target gene levels in vitro. “ut” indicates an untreated sample, which the other samples were normalised to. “Luc” indicates an siRNA targeting Luciferase (X0028), which was used as non-targeting control and does not reduce target mRNA levels.

The experiment was conducted in mouse primary hepatocytes. 25,000 cells were seeded per 96-well and treated with 0.1-100 nM GalNAc-conjugated siRNA directly after plating. Cells were lysed after 24 h, total RNA was extracted and ALDH2 and ApoB mRNA levels were determined by Taqman qRT-PCR. Each bar represents mean±SD from three technical replicates.

Figure 3:
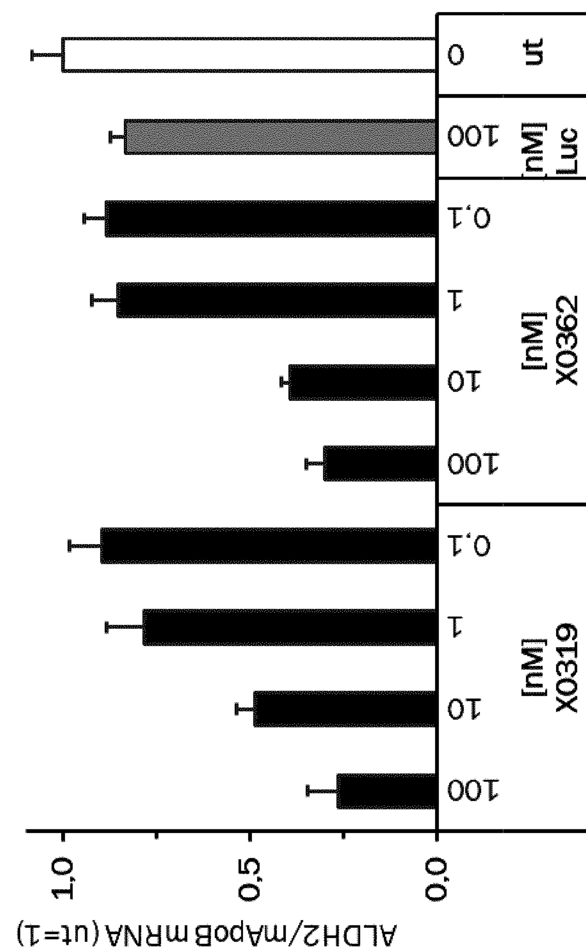
FIG. 3—GalNAc siRNA conjugates with vinylphosphonate at the 5' end of the first strand and phosphodiester internucleotide linkages at the 5' end of the first strand effect reduction of ALDH2 target mRNA levels in vitro.

Data are shown in FIG. 3.

Example 4

GalNAc siRNA conjugates with vinylphosphonate at the 5' end of the first strand and phosphodiester internucleotide linkages at the 5' end of the first strand effect improved reduction of ALDH2 target mRNA levels in vitro.

All tested conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0320 contains two phosphorothioate internucleotide linkages at the 5' end of the first strand. X0363 contains a vinylphosphonate modification at the first nucleotide and no phosphorothioate internucleotide linkages at the 5' end of the first strand. Compared to X0320, X0363 shows improved reduction of ALDH2 target gene levels in vitro. "ut" indicates an untreated sample, which the other samples were normalised to. "Luc" indicates an siRNA targeting Luciferase (X0028), which was used as non-targeting control and does not reduce target mRNA levels.

The experiment was conducted in mouse primary hepatocates. 25,000 cells were seeded per 96-well and treated with 0.1-100 nM GalNAc-conjugated siRNA directly after plating. Cells were lysed after 24 h, total RNA was extracted and ALDH2 and ApoB mRNA levels were determined by Taqman qRT-PCR. Each bar represents mean±SD from three technical replicates.

Figure 4:
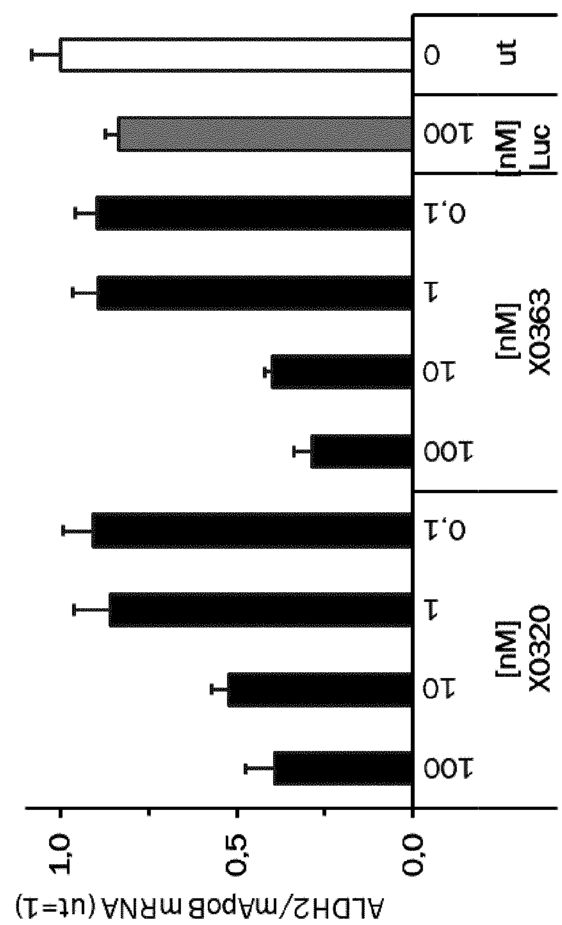
FIG. 4—GalNAc siRNA conjugates with vinylphosphonate at the 5' end of the first strand and phosphodiester internucleotide linkages at the 5' end of the first strand effect improved reduction of ALDH2 target mRNA levels in vitro.

Data are shown in FIG. 4.

The anti-ALDH2 siRNAs of examples 3 and 4 have different sequences. These examples show that the presence of a vinylphosphonate and phosphorothioate linkages at the 5' end of the first strand improve activity of the siRNA regardless of the sequence.

Example 5

GalNAc siRNA conjugates with vinylphosphonate at the 5' end of the first strand and phosphodiester internucleotide linkages at the 5' end of the first strand are stable in acidic tritosome lysate.

All tested conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0181 contains two phosphorothioate internucleotide linkages at the 5' end of the first strand. X0430 contains a vinylphosphonate modification at the first nucleotide ("vp-mU") and two phosphorothioate ("PS") internucleotide linkages at the 5' end of the first strand. X0349 contains a vinylphosphonate modification at the first nucleotide and no phosphorothioate internucleotide linkages at the 5' end of the first strand. All GalNAc siRNA conjugates are stable for at least 72 hours. This is surprising because it is generally thought in the art that a phosphorothioate internucleotide linkages are required at the ends of siRNAs to be stable. The inventors have surprisingly found that in the presence of a vinylphosphonate, phosphorothioate internucleotide linkages are not required at the end at which the vinylphosphonate is located. The number of phosphorothioate internucleotide linkages can therefore be unexpectedly reduced without leading to unstable molecules. This is an advantage because such molecules have fewer stereogenic centres (the phosphorothioate are stereogenic).

To assess stability, 5 μM siRNA conjugate was incubated with acidic rat tritosome extract (pH 5) at 37° C. for 0, 4, 24, and 72 hours. After incubation, RNA was purified, separated on 20% TBE polyacrylamide gels and visualised by ethidium bromide staining.

Figure 5:
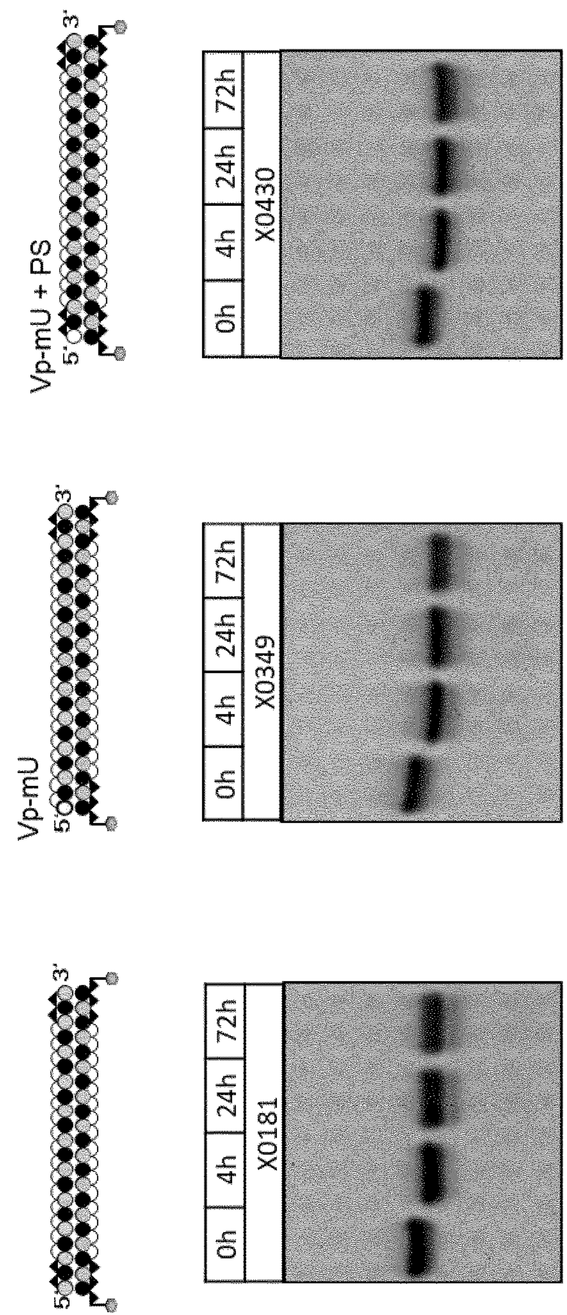
FIG. 5—GalNAc siRNA conjugates with vinylphosphonate at the 5' end of the first strand and phosphodiester internucleotide linkages at the 5' end of the first strand are stable in acidic tritosome lysate.

Data are shown in FIG. 5.

Example 6

GalNAc siRNA conjugates with vinylphosphonate at the 5' end of the first strand and phosphodiester internucleotide linkages at the 5' end of the first strand are stable in acidic tritosome lysate.

All tested conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0322 contains two phosphorothioate internucleotide linkages at the 5' end of the first strand. X0431 contains a vinylphosphonate modification at the first nucleotide ("vp-mU") and two phosphorothioate ("PS") internucleotide linkages at the 5' end of the first strand. X0365 contains a vinylphosphonate modification at the first nucleotide and no phosphorothioate internucleotide linkages at the 5' end of the first strand. All GalNAc siRNA conjugates are stable for at least 72 hours.

To assess stability, 5 μM siRNA conjugate was incubated with acidic rat tritosome extract (pH 5) at 37° C. for 0, 4, 24, and 72 hours. After incubation, RNA was purified, separated on 20% TBE polyacrylamide gels and visualised by ethidium bromide staining.

Figure 6:
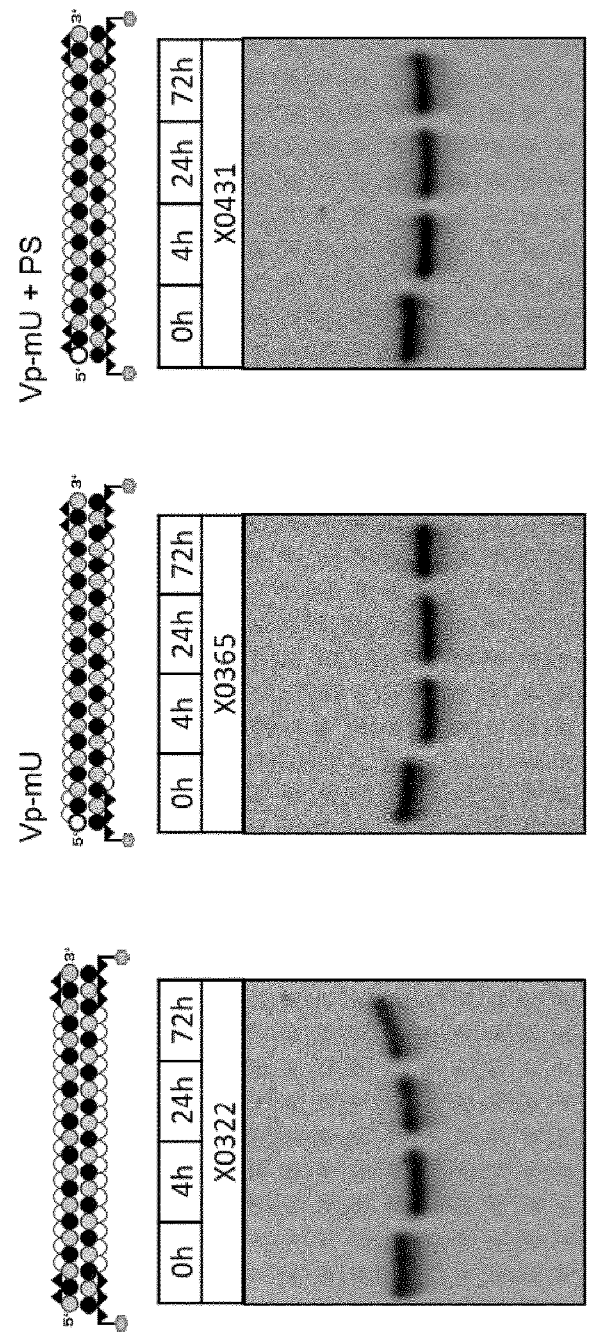
FIG. 6—GalNAc siRNA conjugates with vinylphosphonate at the 5' end of the first strand and phosphodiester internucleotide linkages at the 5' end of the first strand are stable in acidic tritosome lysate.

Data are shown in FIG. 6.

Example 7

GalNAc siRNA conjugates with vinylphosphonate at the 5' end of the first strand and phosphodiester internucleotide linkages at the 5' end of the first strand are stable in acidic tritosome lysate.

Both tested siRNA conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0319 contains two phosphorothioate internucleotide linkages at the 5' end of the first strand. X0362 contains a vinylphosphonate modification at the first nucleotide and no phosphorothioate internucleotide linkages at the 5' end of the first strand. Both GalNAc siRNA conjugates are stable for at least 72 hours.

To assess stability, 5 μM siRNA conjugate was incubated with acidic rat tritosome extract (pH 5) at 37° C. for 0, 4, and 72 hours. After incubation, RNA was purified, separated on 20% TBE polyacrylamide gels and visualised by ethidium bromide staining.

Figure 7:
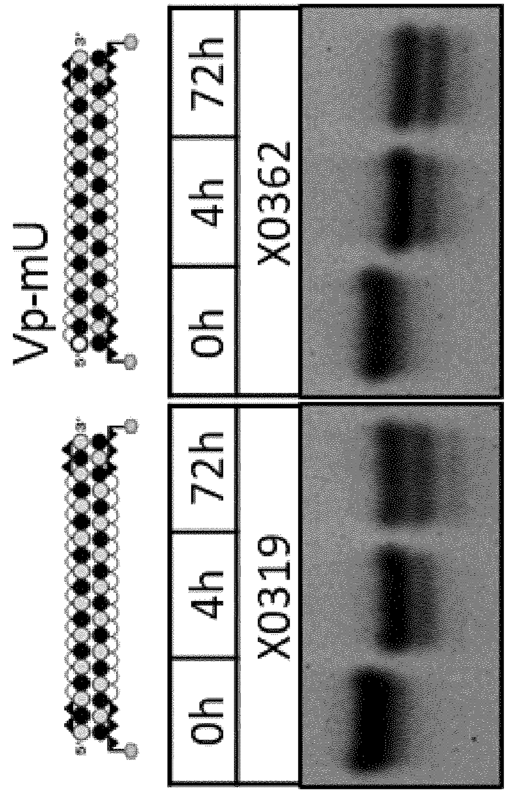
FIG. 7—GalNAc siRNA conjugates with vinylphosphonate at the 5' end of the first strand and phosphodiester internucleotide linkages at the 5' end of the first strand are stable in acidic tritosome lysate.

Data are shown in FIG. 7.

Example 8

GalNAc siRNA conjugates with vinylphosphonate at the 5' end of the first strand and phosphodiester internucleotide linkages at the 5' end of the first strand are stable in acidic tritosome lysate.

Both tested siRNA conjugates contain each one Serinol-linked GalNAc moiety at the 5' end and at the 3' end of the second strand. The siRNAs are modified with alternating 2'-OMe/2'-F and contain each two phosphorothioate internucleotide linkages at their 5' and 3' termini, if not stated differently. X0320 contains two phosphorothioate internucleotide linkages at the 5' end of the first strand. X0363 contains a vinylphosphonate modification at the first nucleotide and no phosphorothioate internucleotide linkages at the 5' end of the first strand. Both GalNAc siRNA conjugates are stable for at least 72 hours.

To assess stability, 5 μM siRNA conjugate was incubated with acidic rat tritosome extract (pH 5) at 37° C. for 0, 4, and 72 hours. After incubation, RNA was purified, separated on 20% TBE polyacrylamide gels and visualised by ethidium bromide staining.

Figure 8:
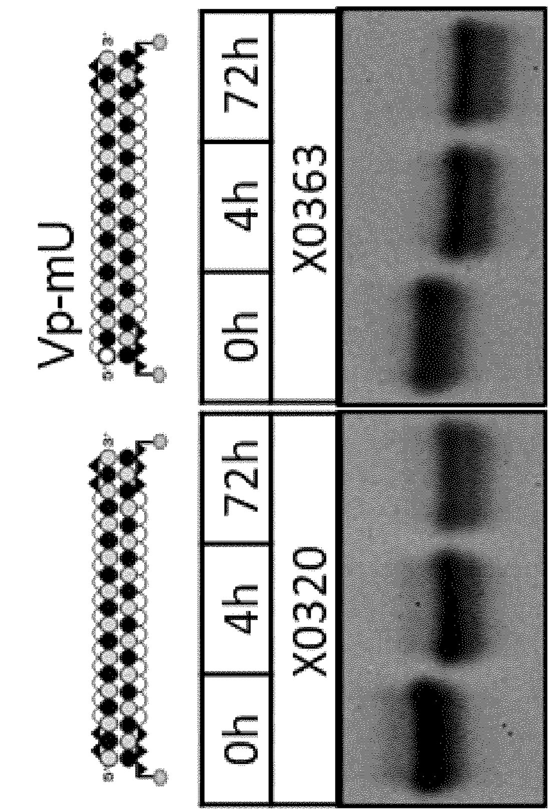
FIG. 8—GalNAc siRNA conjugates with vinylphosphonate at the 5' end of the first strand and phosphodiester internucleotide linkages at the 5' end of the first strand are stable in acidic tritosome lysate.

Data are shown in FIG. 8.

Collectively, examples 5-8 show that the stability of siRNAs that lack phosphorothioate internucleotide linkages at the 5' end of the sense strand is not a function of the sequences of the siRNAs because the same result is obtained with siRNAs that have four entirely different sequences.

Example 9

GalNAc siRNA conjugates with vinylphosphonate at the 5' end of the first strand and phosphodiester internucleotide linkages at the 5' end of the first strand effect improved reduction of TMPRSS6 target mRNA levels in vivo.

All tested conjugates contain a triantennary GalNAc moiety at the 5' end of the second strand. The siRNAs are modified with alternating 2'-OMe/2'-F and contain each two phosphorothioate internucleotide linkages at all non-conjugated ends if not stated differently. X0027 and X0207 contain two phosphorothioate internucleotide linkages at the 5' end of the first strand. X0204 contains a vinylphosphonate modification at the first nucleotide and two phosphorothioate internucleotide linkages at the 5' end of the first strand. X0205 contains a vinylphosphonate modification at the first nucleotide and no phosphorothioate internucleotide linkages at the 5' end of the first strand. X0205 shows improved reduction of TMPRSS6 transcript levels in vivo compared to X0027, X0207 and X0204. "PBS" indicates a group of animals, which was treated with PBS.

C57BL6 male mice (n=6) were subcutaneously treated with 0.3 mg/kg and 1 mg/kg GalNAc conjugate. Liver sections were prepared 7 days after treatment, total RNA was extracted from the tissue and TMPRSS6 and PTEN mRNA levels were determined by TaqMan qRT-PCR.

Figure 9:
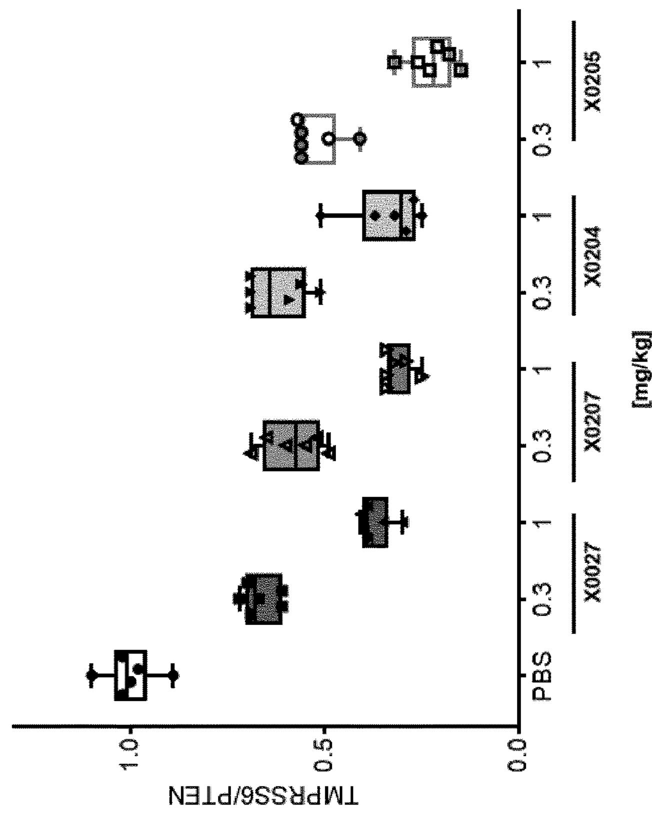
FIG. 9—GalNAc siRNA conjugates with vinylphosphonate at the 5' end of the first strand and phosphodiester internucleotide linkages at the 5' end of the first strand effect improved reduction of TMPRSS6 target mRNA levels in vivo.

Data are shown in FIG. 9.

Example 10

GalNAc siRNA conjugates with vinylphosphonate at the 5' end of the first strand and phosphodiester internucleotide linkages at the 5' end of the first strand effect improved reduction of TMPRSS6 target mRNA levels in vivo over six weeks.

The tested conjugates contain a triantennary GalNAc moiety at the 5' end of the second strand. The siRNAs are modified with alternating 2'-OMe/2'-F and contain each two phosphorothioate internucleotide linkages at all non-conjugated ends if not stated differently. X0027 contains two phosphorothioate internucleotide linkages at the 5' end of the first strand. X0205 contains a vinylphosphonate modification at the first nucleotide and no phosphorothioate internucleotide linkages at the 5' end of the first strand. X0027 and X0205 contain different nucleobases at position 1 of the first strand and at position 19 of the second strand, whereas the remaining nucleobase sequence is identical. Compared to X0027, X0205 shows improved initial reduction of TMPRSS6 target gene levels in vivo and improved duration of action in vivo. "PBS" indicates a group of animals, which was treated with PBS.

C57BL6 male mice (n=6) were subcutaneously treated with 1 mg/kg GalNAc conjugate. Liver sections were prepared 10, 20, and 41 days after treatment, total RNA was extracted from the tissue and TMPRSS6 and ACTB mRNA levels were determined by Taqman qRT-PCR.

Figure 10:
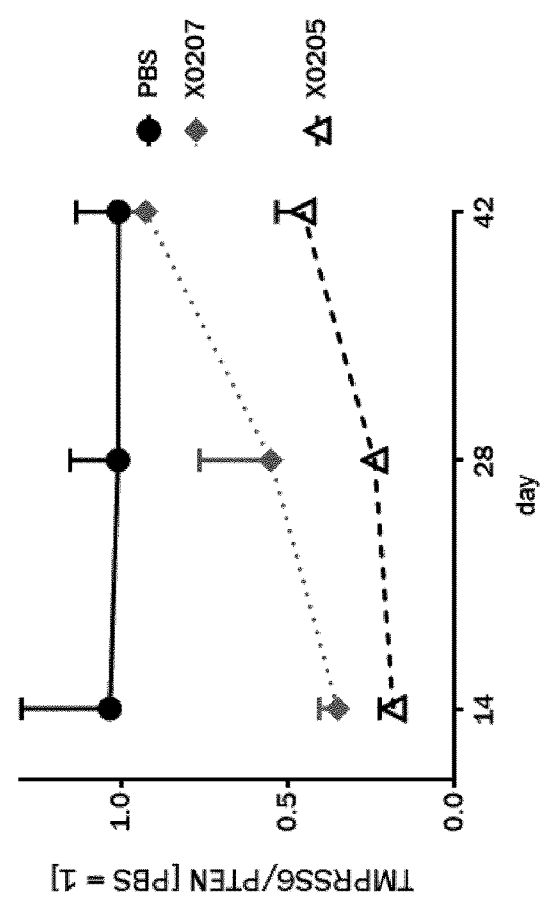
FIG. 10—GalNAc siRNA conjugates with vinylphosphonate at the 5' end of the first strand and phosphodiester internucleotide linkages at the 5' end of the first strand effect improved reduction of TMPRSS6 target mRNA levels in vivo over six weeks.

Data are shown in FIG. 10.

Example 11

GalNAc siRNA conjugates with vinylphosphonate at the 5' end of the first strand and phosphodiester internucleotide linkages at the 5' end of the first strand effect reduction of ALDH2 target mRNA levels in vitro.

All tested conjugates contain each one Serinol-linked GalNAc moiety at the 5' end and at the 3' end of the second strand. The siRNAs contain each two phosphorothioate internucleotide linkages at their 5' and 3' termini, if not stated differently. X0320 and X363 are modified with alternating 2'-OMe/2'-F. X0477 and X0478 are modified with alternating 2'-OMe/2'-F in the first strand and with 2'-OMe at positions 1-6 and 10-19 of the second strand and with 2'-F at positions 7-9 of the second strand. X0320 and X0477 contain two phosphorothioate internucleotide linkages at the 5' end of their first strands. X0363 and X0478 contains a vinylphosphonate modification at the first nucleotide and no phosphorothioate internucleotide linkages at the 5' end of the first strand. Compared to X0320, X0363 reduced ALDH2 mRNA levels more. Compared to X0477, X0478 reduced ALDH2 mRNA levels more. "ut" indicates an untreated sample, which the other samples were normalised to. "Luc" indicates an siRNA targeting Luciferase (X0028), which was used as non-targeting control and does not reduce target mRNA levels.

The experiment was conducted in mouse primary hepatocytes. 20,000 cells were seeded per 96-well and treated with 1-100 nM GalNAc-conjugated siRNA directly after plating. Cells were lysed after 24 h, total RNA was extracted and ALDH2 and ACTB mRNA levels were determined by Taqman qRT-PCR. Each bar represents mean±SD from three technical replicates.

Figure 11:
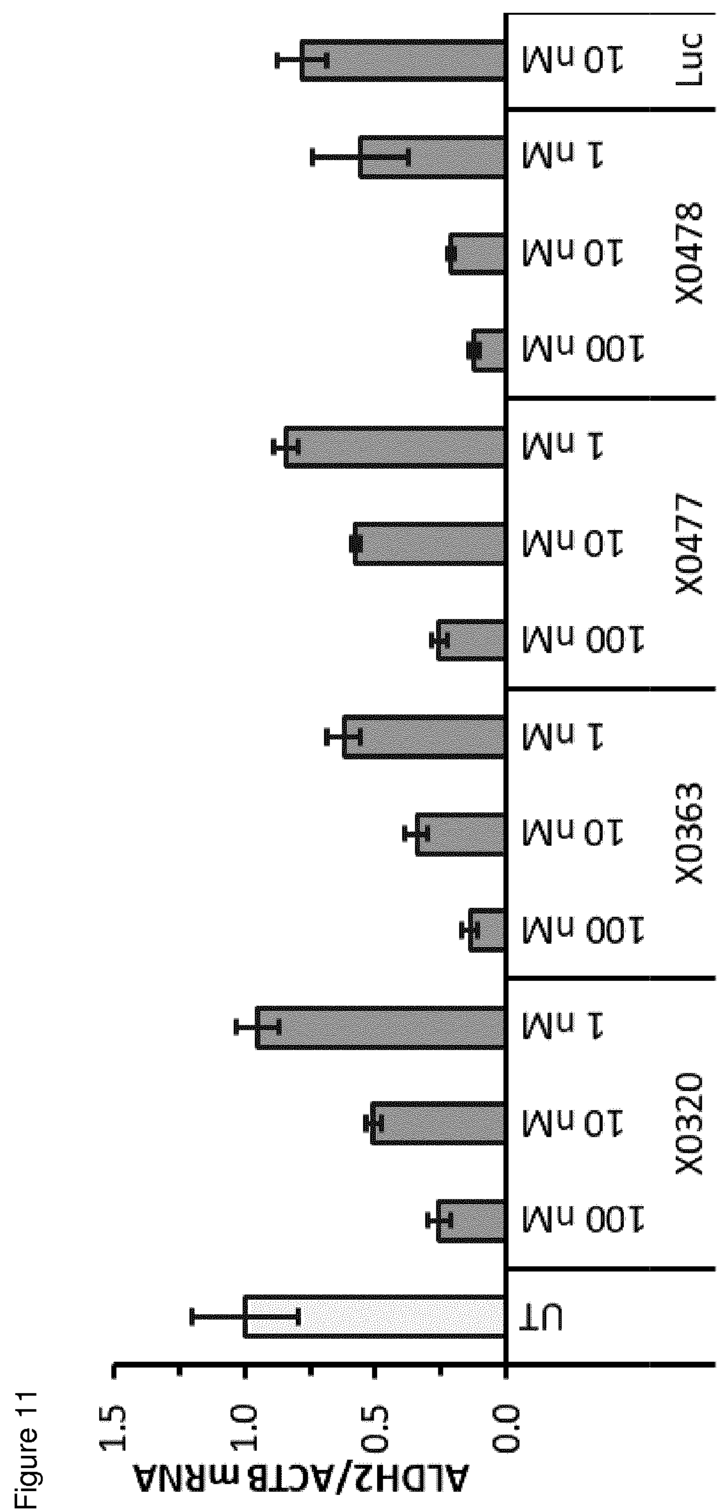
FIG. 11—GalNAc siRNA conjugates with vinylphosphonate at the 5' end of the first strand and phosphodiester internucleotide linkages at the 5' end of the first strand effect reduction of ALDH2 target mRNA levels in vitro.

Data are shown in FIG. 11.

Example 11 shows that a combination of a vinylphosphonate at the 5' end of the antisense strand and the 2' nucleotide modification pattern of the second strand of X0478 lead to an unexpectedly higher down-regulation of the target gene.

Example 12—Synthesis

General Synthesis Schemes

Example compounds can be synthesised according to methods described below and known to the person skilled in the art. Whilst the schemes illustrate the synthesis of particular conjugates, it will be understood that other claimed conjugates may be prepared by analogous methods. Assembly of the oligonucleotide chain and linker building blocks may, for example, be performed by solid phase synthesis applying phosphoramidte methodology. Solid phase synthesis may start from a base or modified building block loaded Icaa CPG. Phosphoramidite synthesis coupling cycle consists of 1) DMT-removal, 2) chain elongation using the required DMT-masked phosphoramidite and an activator, which may be benzylthiotetrazole (BTT), 3) capping of non-elongated oligonucleotide chains, followed by oxidation of the P(III) to P(V) either by Iodine (if phosphodiester linkage is desired) or EDITH (if phosphorothioate linkage is desired) and again capping (Cap/Ox/Cap or Cap/Thio/Cap). GalNAc conjugation may be achieved by peptide bond formation of a GalNAc-carboxylic acid building block to the prior assembled and purified oligonucleotide having the necessary number of amino modified linker building blocks attached. The necessary building blocks are either commercially available or synthesis is described below. All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products was proved by LC-MS analysis.

Synthesis of Synthons

Scheme 1

Synthesis of DMT-serinol(TFA) linker synthons

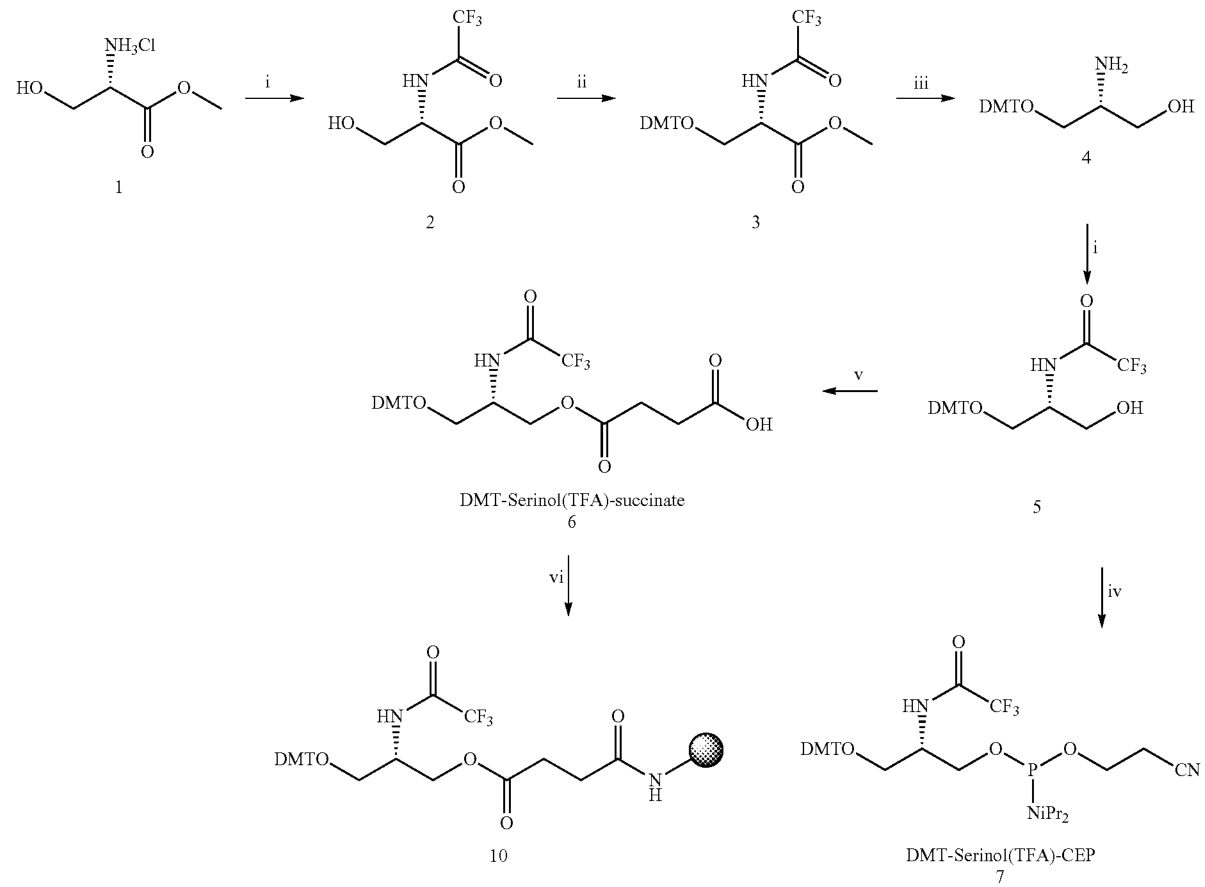

i) ethyl trifluoroacetate, $NEt_3$, MeOH, 0° C., 16 h, 2: 86% 5: 90%, ii) DMTCl, pyridine, 0° C., 16 h, 74%, iii) $LiBH_4$, EtOH/THF (1/1, v/v), 0° C., 1 h, 76%, iv) 2-cyanoethyl-N,N-diisopropylchloro phosphoramidite, $EtNiPr_2$, $CH_2Cl_2$, 56%, v) succinic anhydride, DMAP, pyridine, RT, 16 h, 38%, vi) HBTU, DIEA, amino-Icaa CPG (500A), RT, 18 h, 29% (26 umol/g loading).

(S)-DMT-Serinol(TFA)-phosphoramidite 7 can be synthesised from (L)-serine methyl ester derivative 1 according to literature published methods (Hoevelmann et al. Chem. Sci., 2016, 7, 128-135).

(S)-DMT-Serinol(TFA)-succinate 6 can be made by conversion of intermediate 5 with succinic anhydride in presence of a catalyst such as DMAP.

Loading of 6 to a solid support such as a controlled pore glass (CPG) support may be achieved by peptide bond formation to a solid support such as an amino modified native CPG support (500 A) using a coupling reagent such as HBTU. The (S)-DMT-Serinol(TFA)-succinate 6 and a coupling reagent such as HBTU is dissolved in a solvent such as $CH_3CN$. A base, such as diisopropylethylamine, is added to the solution, and the reaction mixture is stirred for 2 min. A solid support such as a native amino-Icaa-CPG support (500 A, 3 g, amine content: 136 umol/g) is added to the reaction mixture and a suspension forms. The suspension is gently shaken at room temperature on a wrist-action shaker for 16 h then filtered, and washed with solvent such as DCM and EtOH. The support is dried under vacuum for 2 h. The unreacted amines on the support can be capped by stirring with acetic anhydride/lutidine/N-methylimidazole at room temperature. Washing of the support may be repeated as above. The solid support is dried under vacuum to yield solid support 10.

Scheme 2
Synthesis of GalNAc synthon 9

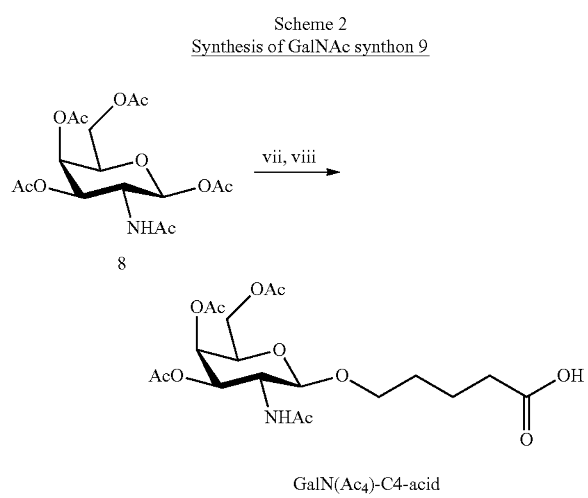

(vii) TMSOTf, DCM, hexenol, viii) $RuCl_3$, $NaIO_4$, DCM, $CH_3CN$, $H_2O$, 46% over two steps.

Synthesis of the GalNAc synthon 9 can be prepared according to methods as described in Nair et al. (2014), starting from commercially available per-acetylated galactose amine 8.

Synthesis of single stranded serinol-derived GalNAc conjugates

Scheme 3
General procedure of oligonucleotide synthesis for serinol-derived linkers

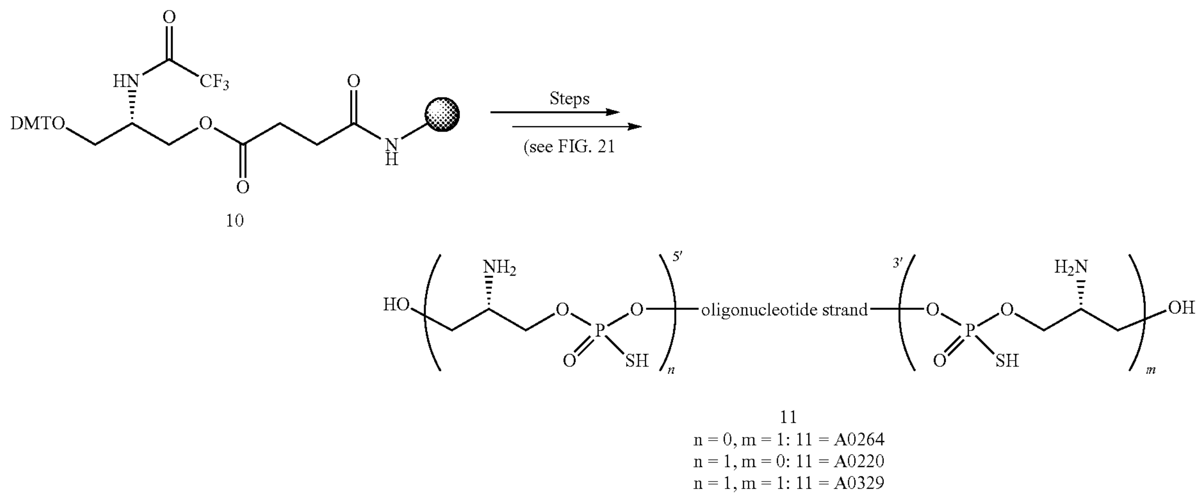

Figure 16:
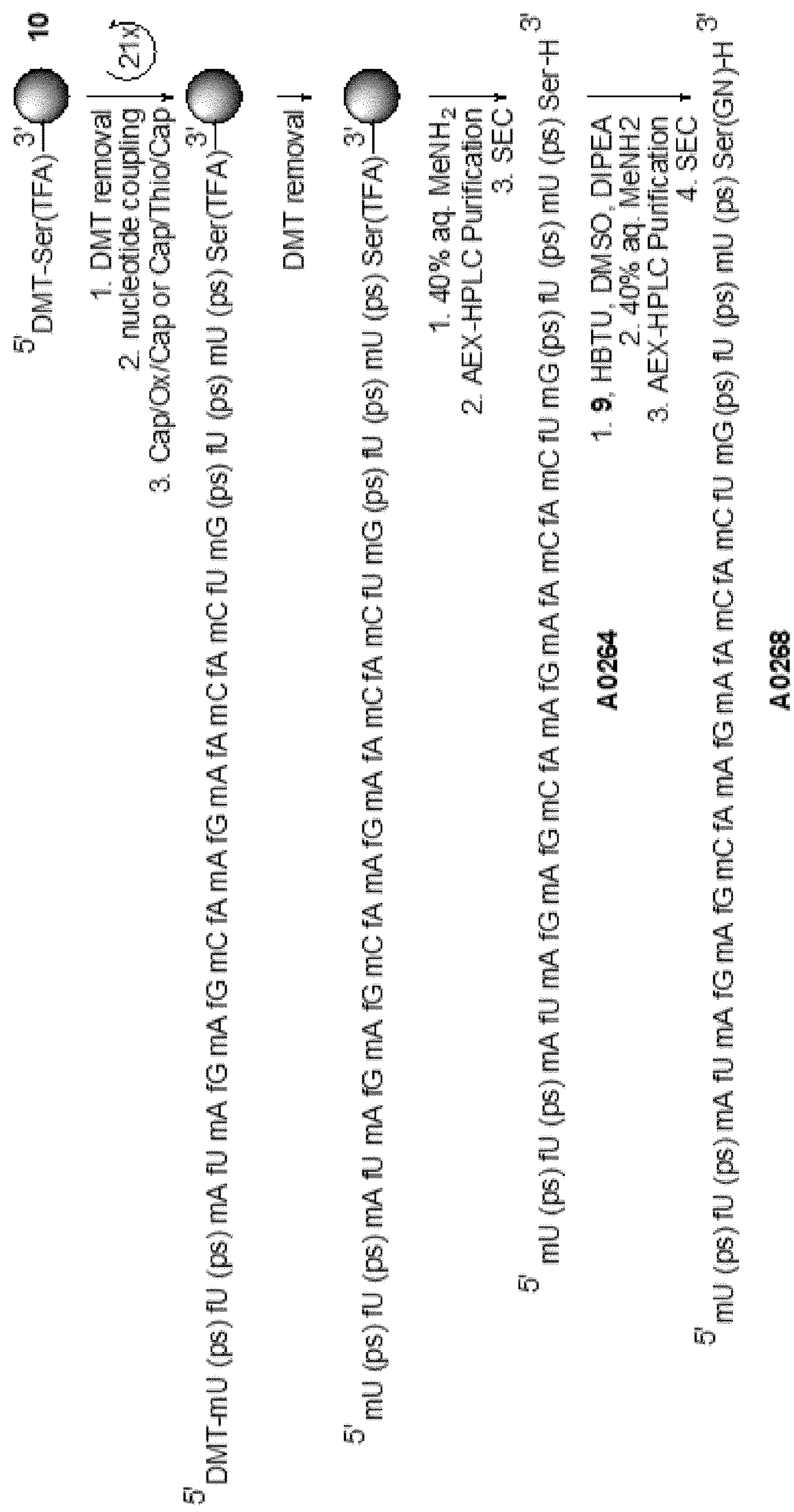
FIG. 16—shows the synthesis of A0268 which is a 3' mono-GalNAc conjugated single stranded oligonucleotide and is the second strand starting material in the synthesis of an exemplary conjugate of the invention.

Oligonucleotide synthesis of 3' mono-GalNAc conjugated oligonucleotides (such as compound A0264) is outlined in FIG. 16 and summarised in Scheme 3. Synthesis is commenced using (S)-DMT-Serinol(TFA)-succinate-Icaa-CPG 10 as in example compound A0264. In case additional serinol building blocks are needed the (S)-DMT-serinol (TFA) amidite (7) is used in the appropriate solid phase synthesis cycle. For example, to make compound A0329, the chain assembly is finished with an additional serinol amidite coupling after the base sequence is fully assembled. Further, oligonucleotide synthesis of 5' mono-GalNAc conjugated oligonucleotides may be commenced from a solid support loaded with the appropriate nucleoside of its respected sequence. In example compound A0220 this may be 2'fA. The oligonucleotide chain is assembled according to its sequence and as appropriate, the building block (S)-DMT-serinol(TFA)-amidite (7) is used. Upon completion of chain elongation, the protective DMT group of the last coupled amidite building block is removed, as in step 1) of the phosphoramidite synthesis cycle.

Upon completion of the last synthesizer step, the single strands can be cleaved off the solid support by treatment with an amine such as 40% aq. methylamine treatment. Any remaining protecting groups are also removed in this step and methylamine treatment also liberates the serinol amino function. The crude products were then purified each by AEX-HPLC and SEC to yield the precursor oligonucleotide for further GalNAc conjugation.

Scheme 4
GalNAc conjugation synthesis of serinol-derived precursor oligonucleotides

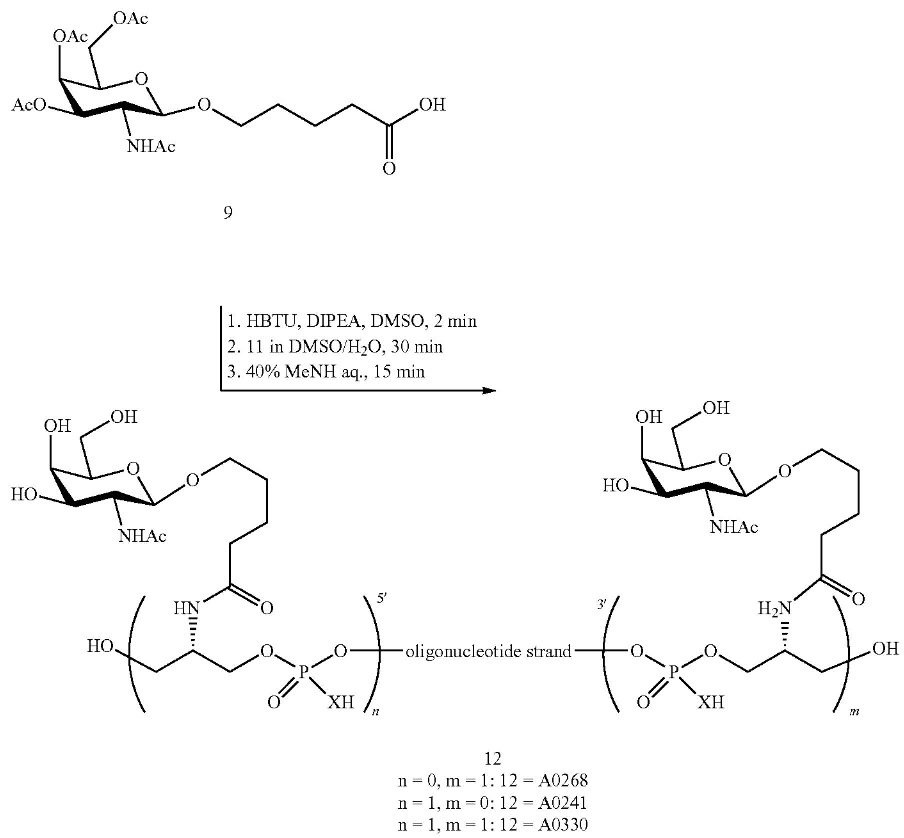

Post solid phase synthesis GalNAc-conjugation was achieved by pre-activation of the GalN(Ac4)-C4-acid (9) by a peptide coupling reagent such as HBTU. The pre-activated acid 9 was then reacted with the amino-groups in 11 (e.g. A0264) to form the intermediate GalN(Ac4)-conjugates. The acetyl groups protecting the hydroxyl groups in the GalNAc-moieties were cleaved off by methylamine treatment to yield the desired example compounds 12 (e.g. A0268), which were further purified by AEX-HPLC and SEC.

Synthesis of Single Stranded Non-Serinol-Derived GalNAc Conjugates

Amino modified building blocks other than serinol are commercially available from various suppliers and can be used instead of serinol to provide reactive amino-groups that allow for GalNAc conjugation. For example the commercially available building blocks shown in Table 1 below can be used to provide non-serinol-derived amino modified precursor oligonucleotides 14 (Scheme 5A) by using amino-modifier loaded CPG such as 10-1 to 10-3 followed by sequence assembly as described above and finally coupling of amino-modifier phosohoramidites such as 13-1, 13-2 or 13-4.

For example, to make 14 (A0653) GyC3Am-CPG (10-2) was used in combination with GlyC3Am-Amidite 13-2. Structurally differing modifiers can be used to make 14, for example for A0651 C7Am-CPG was used in combination with C6Am-Amidite as second amino modification. In a similar fashion commercially available amino-modifier loaded CPG 10-5 and amino-modified phosphoramidite 13-5 can be used to synthesise amino-modified precursor molecules 14 (A0655).

TABLE 1

| Commercially available building blocks |
|---|
| C3Am-CPG (10-1) is: |
| 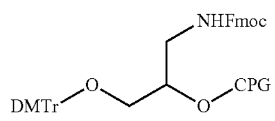 |
| GlyC3Am-CPG (10-2) is: |
| 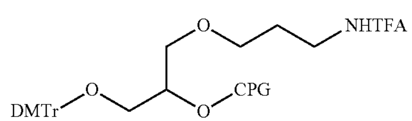 |
| C7Am-CPG (10-3) is: |
| 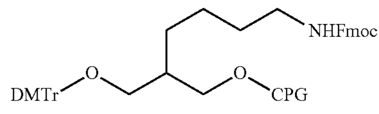 |

TABLE 1-continued

| Commercially available building blocks |
| --- |
| PipAm-CPG (10-5) is: |
| C3Am-Phos (13-1) is: |
| GlyC3Am-Phos (13-2) is: |
| C6Am-Phos (13-4) is: |
| PipAm-Phos (13-5) is: |

Scheme 5

General procedure for oligonucleotide synthesis

A)

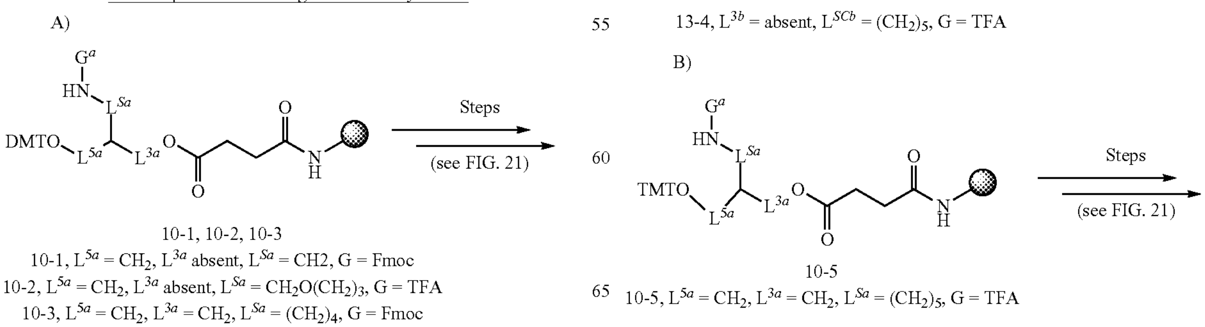

10-1, 10-2, 10-3

10-1, $L^{5a} = CH_2$, $L^{3a}$ absent, $L^{Sa}$ = CH2, G = Fmoc 10-2, $L^{5a} = CH_2$, $L^{3a}$ absent, $L^{Sa} = CH_2O(CH_2)_3$, G = TFA 10-3, $L^{5a} = CH_2$, $L^{3a} = CH_2$, $L^{Sa} = (CH_2)_4$, G = Fmoc -continued

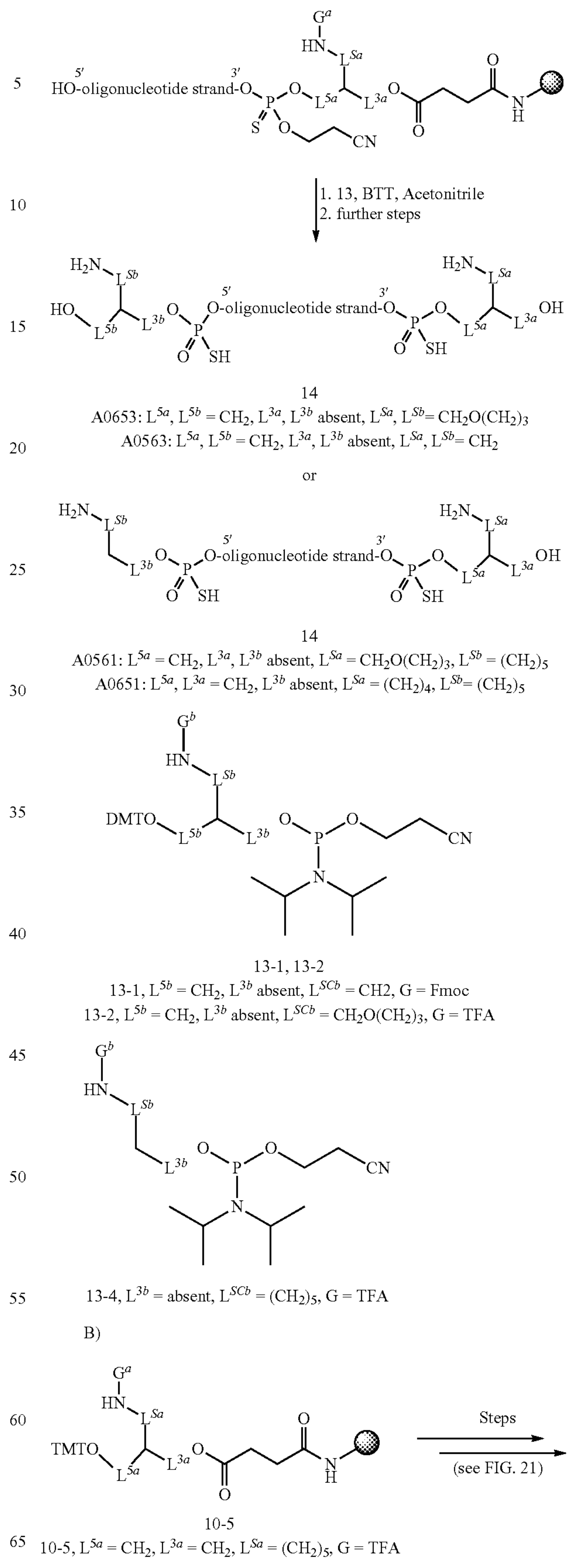

14

A0653: $L^{5a}$, $L^{5b} = CH_2$, $L^{3a}$, $L^{3b}$ absent, $L^{Sa}$, $L^{Sb} = CH_2O(CH_2)_3$ A0563: $L^{5a}$, $L^{5b} = CH_2$, $L^{3a}$, $L^{3b}$ absent, $L^{Sa}$, $L^{Sb} = CH_2$ or

14

A0561: $L^{5a} = CH_2$, $L^{3a}$, $L^{3b}$ absent, $L^{Sa} = CH_2O(CH_2)_3$, $L^{Sb} = (CH_2)_5$ A0651: $L^{5a}$, $L^{3a} = CH_2$, $L^{3b}$ absent, $L^{Sa} = (CH_2)_4$, $L^{Sb} = (CH_2)_5$ 13-1, 13-2

13-1, $L^{5b} = CH_2$, $L^{3b}$ absent, $L^{SCb}$ = CH2, G = Fmoc 13-2, $L^{5b} = CH_2$, $L^{3b}$ absent, $L^{SCb} = CH_2O(CH_2)_3$, G = TFA 13-4, $L^{3b}$ = absent, $L^{SCb} = (CH_2)_5$, G = TFA

B)

10-5

10-5, $L^{5a} = CH_2$, $L^{3a} = CH_2$, $L^{Sa} = (CH_2)_5$, G = TFA

-continued

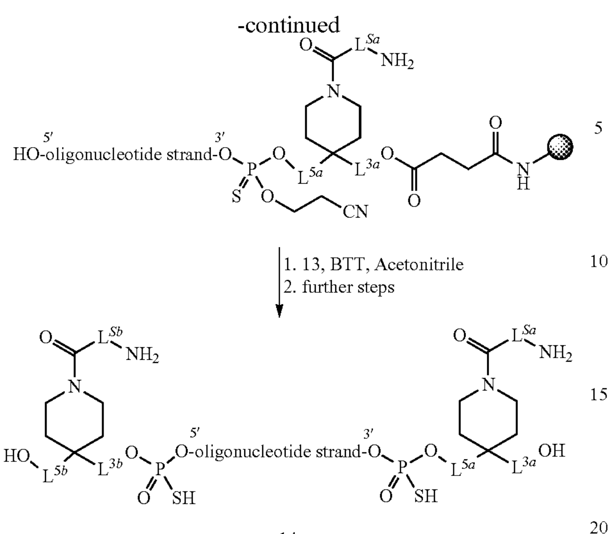

14

A0655: $L^{5a}$, $L^{5b}$ = $CH_2$, $L^{3a}$, $L^{3b}$ $CH_2$, $L^{Sa}$, $L^{Sb}$= $(CH_2)_5$

-continued

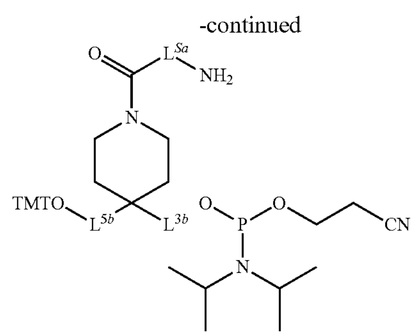

13-5, $L^{5b}$ = $CH_2$, $L^{3b}$ = $CH_2$, $L^{SCb}$ = $(CH_2)_5$, G = TFA

The resulting precursor oligonucleotides 14 can then be conjugated with GalN(Ac4)-$C_4$-acid (9) to yield the desired example compounds 15 (Scheme 6).

Scheme 6

GalNAc conjugation synthesis of precursor oligonucleotides

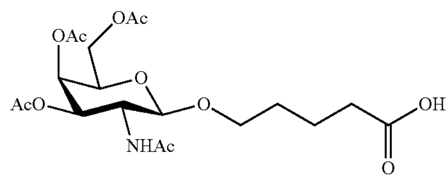

9

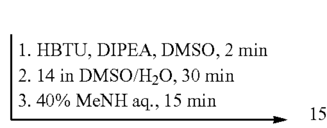

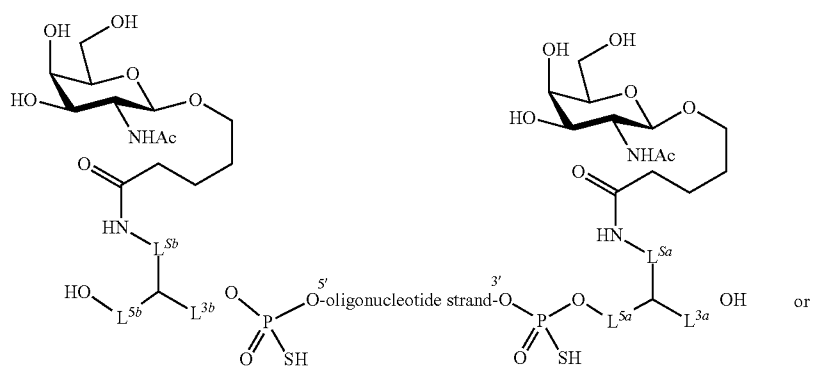

A0654: $L^{5a}$, $L^{5b}$ = $CH_2$, $L^{3a}$, $L^{3b}$ absent, $L^{Sa}$, $L^{Sb}$ = $CH_2O(CH_2)_3$ A0564: $L^{5a}$, $L^{5b}$ = $CH_2$, $L^{3a}$, $L^{3b}$ absent, $L^{Sa}$, $L^{Sb}$ = $CH_2$ -continued

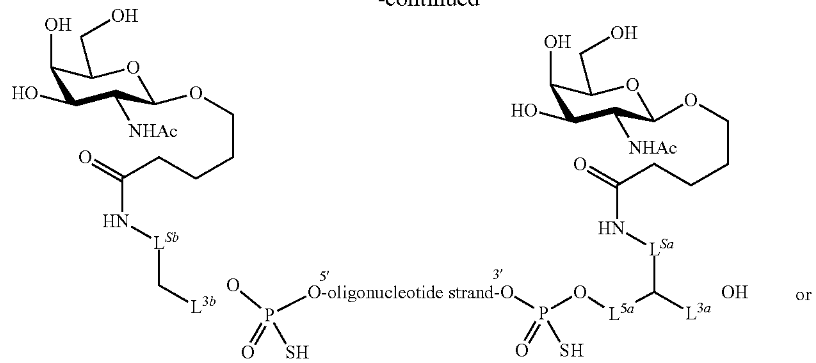

A0562: $L^{5a} = CH_2$, $L^{3a}$, $L^{3b}$ absent, $L^{Sa} = CH_2O(CH_2)_3$, $L^{Sb} = (CH_2)_5$ A0652: $L^{5a}$, $L^{3a} = CH_2$, $L^{3b}$ absent, $L^{Sa} = (CH_2)_4$, $L^{Sb} = (CH_2)_5$

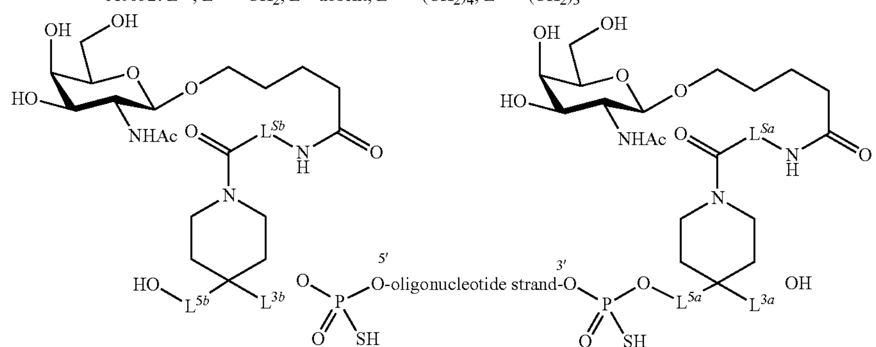

A0656: $L^{5a}$, $L^{5b} = CH_2$, $L^{3a}$, $L^{3b} = CH_2$, $L^{Sa}$, $L^{Sb} = (CH_2)_5$

Synthesis of the Single Stranded Tri-Antennary GalNAc Conjugates

Figure 17:
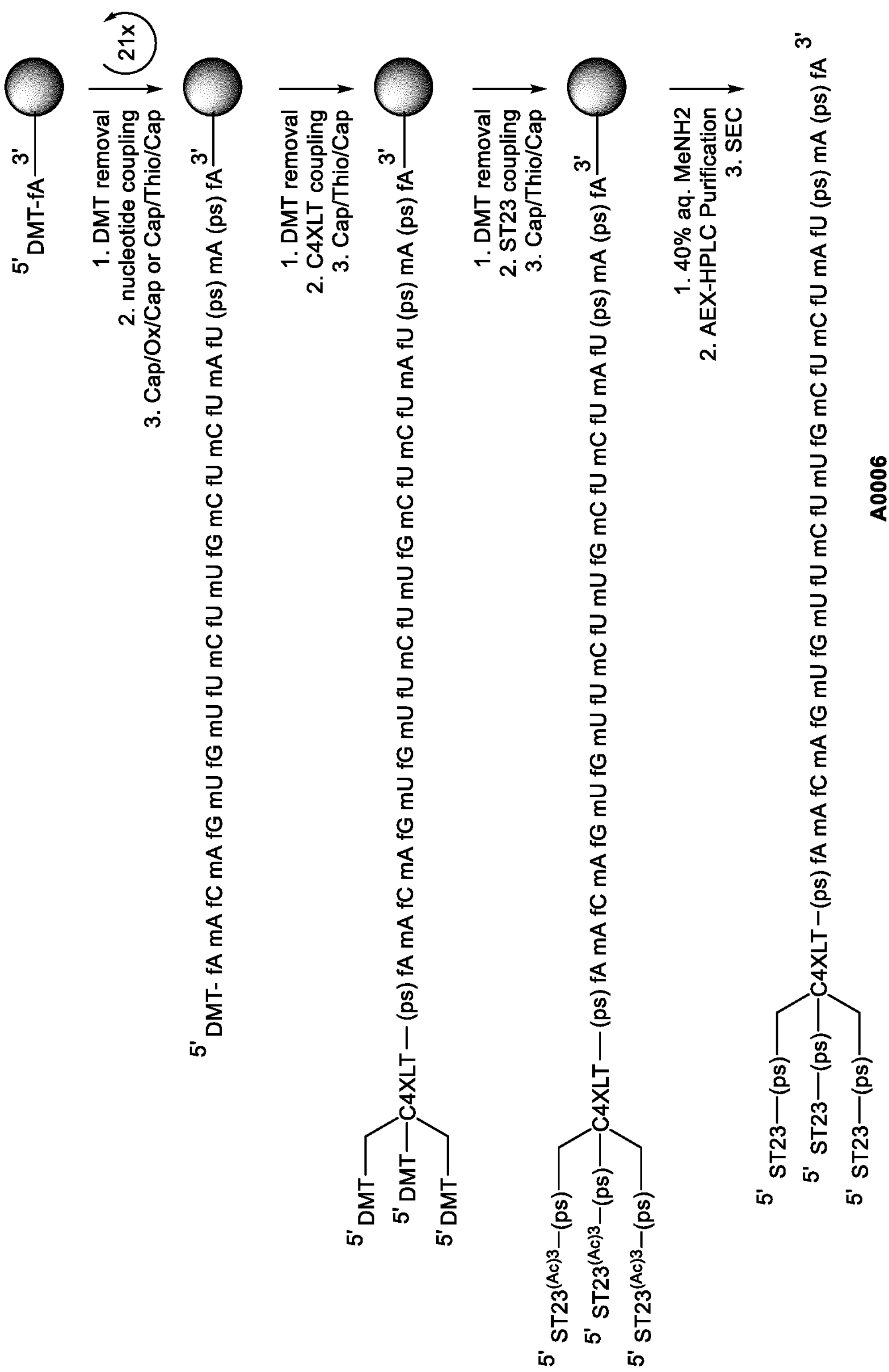
FIG. 17—shows the synthesis of A0006 which is a 5' tri-antennary GalNAc conjugated single stranded oligonucleotide is the second strand starting material in the synthesis of an exemplary conjugate of the invention.

Oligonucleotides synthesis of tri-antennary GalNAc-cluster conjugated siRNA is outlined in FIG. 17. Oligonucleotide chain assembly is commenced using base loaded support e.g. 5'DMT-2'FdA(bz)-succinate-Icaa-CPG as in example compound A0006. Phosphoramidite synthesis coupling cycle consisting of 1) DMT-removal, 2) chain elongation using the required DMT-masked phosphoramidite, 3) capping of non-elongated oligonucleotide chains, followed by oxidation of the P(III) to P(V) either by Iodine or EDITH (if phosphorothioate linkage is desired) and again capping (Cap/Ox/Cap or Cap/Thio/Cap) is repeated until full length of the product is reached. For the on-column conjugation of a trivalent tri-antennary GalNAc cluster the same synthesis cycle was applied with using the necessary trivalent branching amidite C4XLT-phos followed by another round of the synthesis cycle using the GalNAc amidite ST23-phos. Upon completion of this last synthesizer step, the oligonucleotide was cleaved from the solid support and additional protecting groups may be removed by methylamine treatment. The crude products were then purified each by AEX-HPLC and SEC.

General Procedure of Double Strand Formation

In order to obtain the double stranded conjugates, individual single strands are dissolved in a concentration of 60 OD/mL in $H_2O$. Both individual oligonucleotide solutions can be added together to a reaction vessel. For reaction monitoring a titration can be performed. The first strand is added in 25% excess over the second strand as determined by UV-absorption at 260 nm. The reaction mixture is heated e.g. to 80° C. for 5 min and then slowly cooled to RT. Double strand formation may be monitored by ion pairing reverse phase HPLC. From the UV-area of the residual single strand the needed amount of the second strand can be calculated and added to the reaction mixture. The reaction is heated e.g. to 80° C. again and slowly cooled to RT. This procedure can be repeated until less than 10% of residual single strand is detected.

The above process (including Schemes 1-6) may be easily adapted to replace GalNac with another targeting ligand e.g. a saccharide.

In any of the above aspects, instead of post solid phase synthesis conjugation it is possible to make a preformed Serinol(GN)-phosphoramidite and use this for on-column conjugation.

Example compounds were synthesised according to methods described below and methods known to the person skilled in the art. Assembly of the oligonucleotide chain and linker building blocks was performed by solid phase synthesis applying phosphoramidite methodology. GalNAc conjugation was achieved by peptide bond formation of a GalNAc-carboxylic acid building block to the prior assembled and purified oligonucleotide having the necessary number of amino modified linker building blocks attached.

Oligonucleotide synthesis, deprotection and purification followed standard procedures that are known in the art.

All oligonucleotides were synthesized on an AKTA oligopilot synthesizer using standard phosphoramidite chemistry. Commercially available solid support and 2'O-Methyl RNA phosphoramidites, 2'Fluoro, 2'Deoxy RNA phosphoramidites (all standard protection, ChemGenes, LinkTech) and commercially available 3'-Amino Modifier TFA Amino C-6

Icaa CPG 500 Å (Chemgenes) were used. Per-acetylated galactose amine 8 is commercially available.

Ancillary reagents were purchased from EMP Biotech. Synthesis was performed using a 0.1 M solution of the phosphoramidite in dry acetonitrile and benzylthiotetrazole (BTT) was used as activator (0.3M in acetonitrile). Coupling time was 15 min. A Cap/OX/Cap or Cap/Thio/Cap cycle was applied (Cap: $Ac_2O$/NMI/Lutidine/Acetonitrile, Oxidizer: 0.1M 12 in pyridine/$H_2O$). Phosphorothioates were introduced using standard commercially available thiolation reagent (EDITH, Link technologies). DMT cleavage was achieved by treatment with 3% dichloroacetic acid in toluene. Upon completion of the programmed synthesis cycles a diethylamine (DEA) wash was performed. All oligonucleotides were synthesized in DMT-off mode.

Attachment of the serinol-derived linker moiety was achieved by use of either base-loaded (S)-DMT-Serinol (TFA)-succinate-Icaa-CPG 10 or a (S)-DMT-Serinol(TFA) phosphoramidite 7 (synthesis was performed as described in literature Hoevelmann et al. Chem. Sci., 2016, 7, 128-135) in the appropriate synthesis cycle. Tri-antennary GalNAc clusters (ST23/C4XLT or ST23/C6XLT) were introduced by successive coupling of the respective trebler amidite derivatives (C4XLT-phos or C6XLT-phos) followed by the GalNAc amidite (ST23-phos).

Synthesis of the phosphoramidite derivatives of C4XLT (C4XLT-phos), C6XLT (C6XLT-phos) as well as ST23 (ST23-phos) can be performed as described in WO2017/174657. Synthesis of (vp)-mU-phos can be performed as described in Prakash, Nucleic Acids Res. 2015, 43(6), 2993-3011 and Haraszti, Nucleic Acids Res. 2017, 45(13), 7581-7592.

Attachment of vinylphosphonate-mU moiety was achieved by use of (vp)-mU-phos (synthesis was performed as described in Prakash, Nucleic Acids Res. 2015, 43(6), 2993-3011 and Nucleic Acids Res. 2017, 45(13), 7581-7592) in the last synthesis cycle. The (vp)-mU-phos does not provide a hydroxy group suitable for further synthesis elongation and therefore, does not possess an DMT-group. Hence coupling of (vp)-mU-phos results in synthesis termination. For the removal of the methyl-esters masking the phosphonate, the CPG carrying the fully assembled oligonucleotide was dried under reduced pressure and transferred into a 20 mL PP syringe reactor for solid phase peptide synthesis equipped with a disc frit (Carl Roth GmbH). The CPG was then brought into contact with 10 mL of a solution of 250 μL TMSBr and 177 μL pyridine in $CH_2Cl_2$ at room temperature and the reactor was sealed with a luer cap. The reaction vessels were slightly agitated over a period of 30 min, the excess reagent discarded, and the residual CPG washed 2× with 10 mL acetonitrile. Further downstream processing did not alter from any other example compound.

The single strands were cleaved off the CPG by 40% aq. methylamine treatment. The resulting crude oligonucleotide was purified by ion exchange chromatography (Resource Q, 6 mL, GE Healthcare) on a AKTA Pure HPLC System using a sodium chloride gradient. Product containing fractions were pooled, desalted on a size exclusion column (Zetadex, EMP Biotech) and lyophilized.

Individual single strands were dissolved in a concentration of 60 OD/mL in $H_2O$. Both individual oligonucleotide solutions were added together in a reaction vessel. For easier reaction monitoring a titration was performed. The first strand was added in 25% excess over the second strand as determined by UV-absorption at 260 nm. The reaction mixture was heated to 80° C. for 5 min and then slowly cooled to RT. Double strand formation was monitored by ion pairing reverse phase HPLC. From the UV-area of the residual single strand the needed amount of the second strand was calculated and added to the reaction mixture. The reaction was heated to 80° C. again and slowly cooled to RT. This procedure was repeated until less than 10% of residual single strand was detected.

Synthesis of Compounds 2-10

Compounds 2 to 5 and (S)-DMT-Serinol(TFA)-phosphoramidite 7 were synthesised according to literature published methods (Hoevelmann et al. Chem. Sci., 2016, 7, 128-135).

(S)-4-(3-(bis(4-methoxyphenyl)(phenyl)methoxy)-2-(2,2,2-trifluoroacetamido)propoxy)-4-oxobutanoic acid (6)

To a solution of 5 in pyridine was added succinic anhydride, followed by DMAP. The resulting mixture was stirred at room temperature overnight. All starting material was consumed, as judged by TLC. The reaction was concentrated. The crude material was chromatographed in silica gel using a gradient 0% to 5% methanol in DCM (+1% triethylamine) to afford 1.33 g of 6 (yield=38%). m/z (ESI−): 588.2 (100%), (calcd. for $C30H29F3NO8^-$ $[M-H]^-$ 588.6). 1H-NMR: (400 MHz, CDCl3) δ [ppm]=7.94 (d, 1H, NH), 7.39-7.36 (m, 2H, CHaryl), 7.29-7.25 (m, 7H, CHaryl), 6.82-6.79 (m, 4H, CHaryl), 4.51-4.47 (m, 1H), 4.31-4.24 (m, 2H), 3.77 (s, 6H, 2xDMTr-OMe), 3.66-3.60 (m, 16H, $HNEt_3^+$), 3.26-3.25 (m, 2H), 2.97-2.81 (m, 20H, $NEt_3$), 2.50-2.41 (4H, m), 1.48-1.45 (m, 26H, $HNEt_3^+$), 1.24-1.18 (m, 29H, $NEt_3$).

(S)-DMT-Serinol(TFA)-succinate-Icaa-CPG (10)

The (S)-DMT-Serinol(TFA)-succinate (159 mg, 270 umol) and HBTU (113 mg, 299 umol) were dissolved in $CH_3CN$ (10 mL). Diisopropylethylamine (DIPEA, 94 μL, 540 umol) was added to the solution, and the mixture was swirled for 2 min followed by addition native amino-Icaa-CPG (500 A, 3 g, amine content: 136 umol/g). The suspension was gently shaken at room temperature on a wrist-action shaker for 16 h then filtered and washed with DCM and EtOH. The solid support was dried under vacuum for 2 h. The unreacted amines on the support were capped by stirring with acetic anhydride/lutidine/N-methylimidazole at room temperature. The washing of the support was repeated as above. The solid was dried under vacuum to yield solid support 10 (3 g, 26 umol/g loading).

GalNAc Synthon (9)

Synthesis of the GalNAc synthon 9 was performed as described in Nair et al. J. Am. Chem. Soc., 2014, 136 (49), pp 16958-16961, in 46% yield over two steps.

The characterising data matched the published data.

Synthesis of Oligonucleotides

Figure 12:
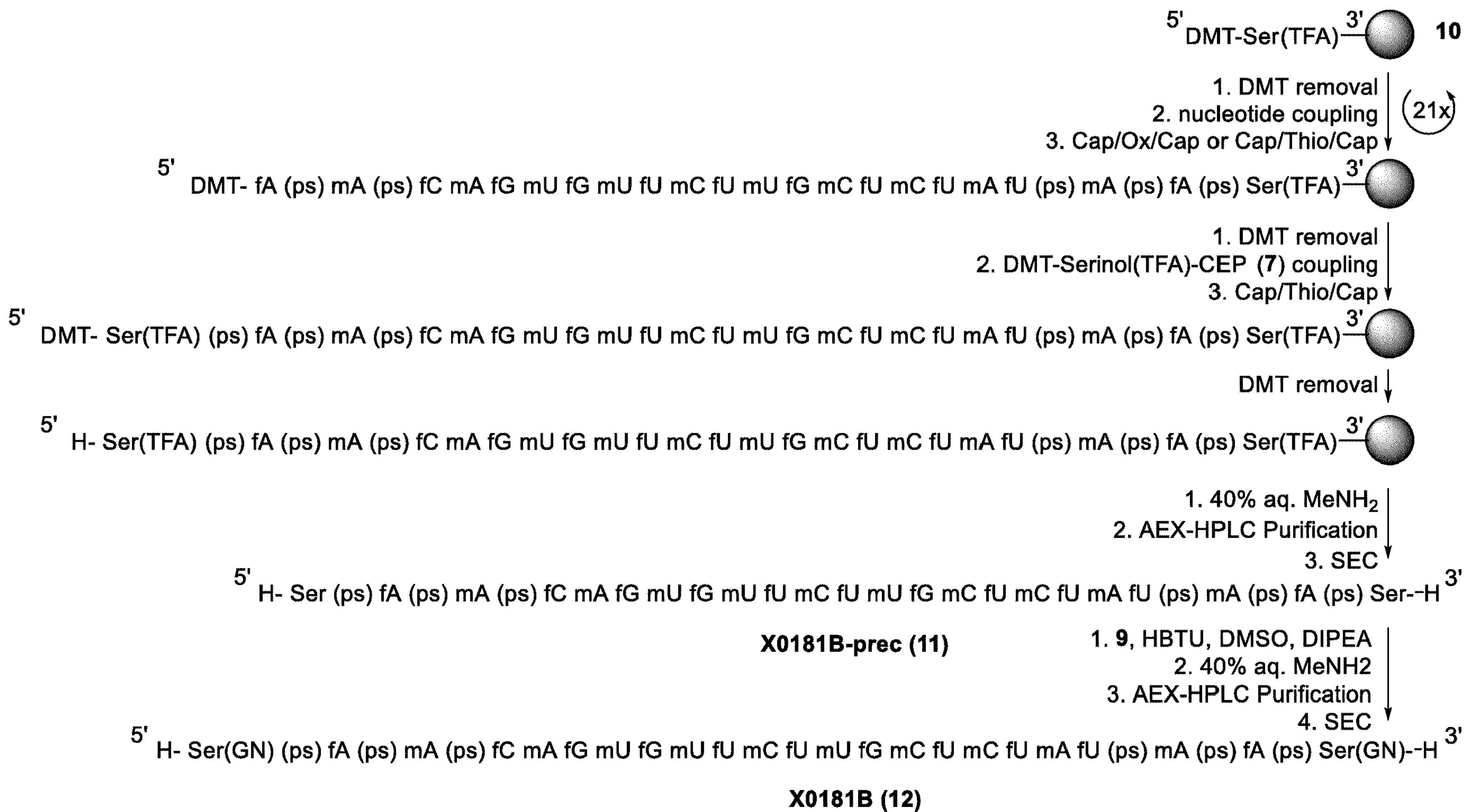
FIG. 12—Oligonucleotide synthesis of 3' and 5' GalNAc conjugated oligonucleotides precursors.
Figure 13B:
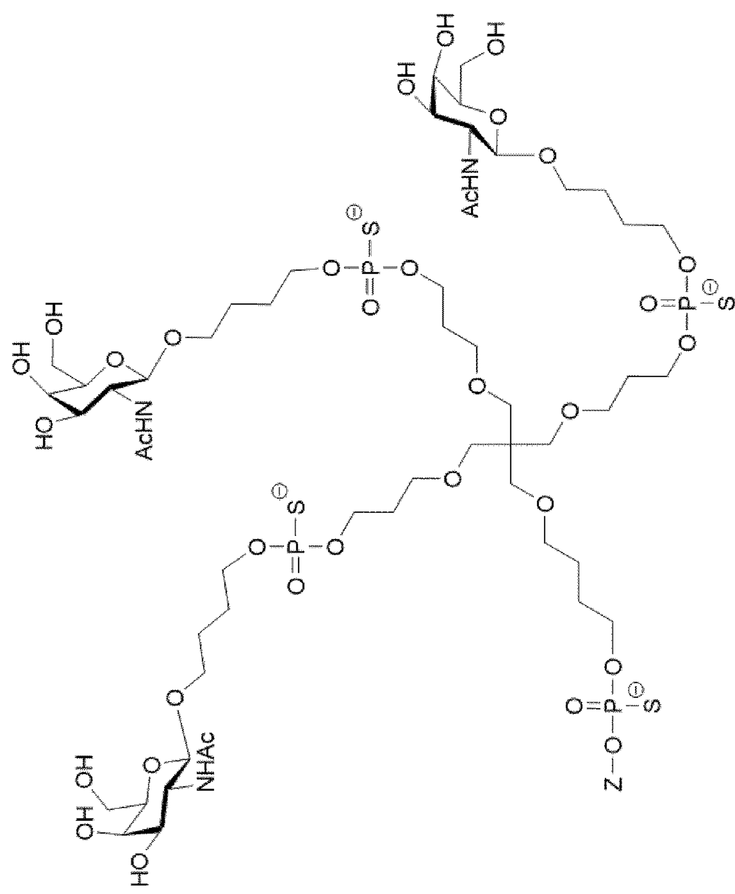
FIGS. 13*a*, 13*b* and 13*c*—the structure of GalNAc ligands referred to herein respectively as GN, GN2 and GN3 to which the oligonuclotides were conjugated.
Figure 13A:
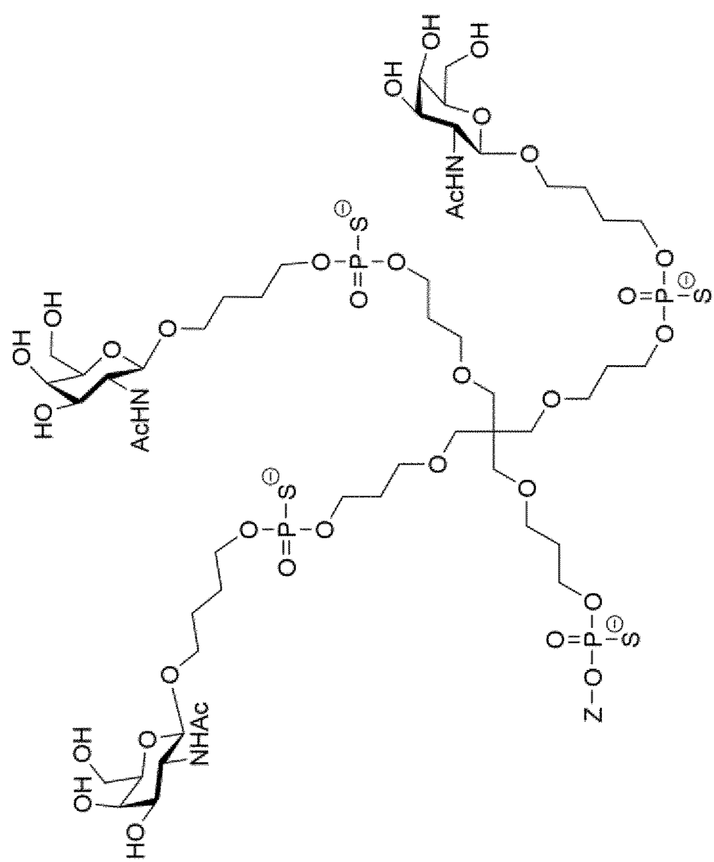
Figure 13C:
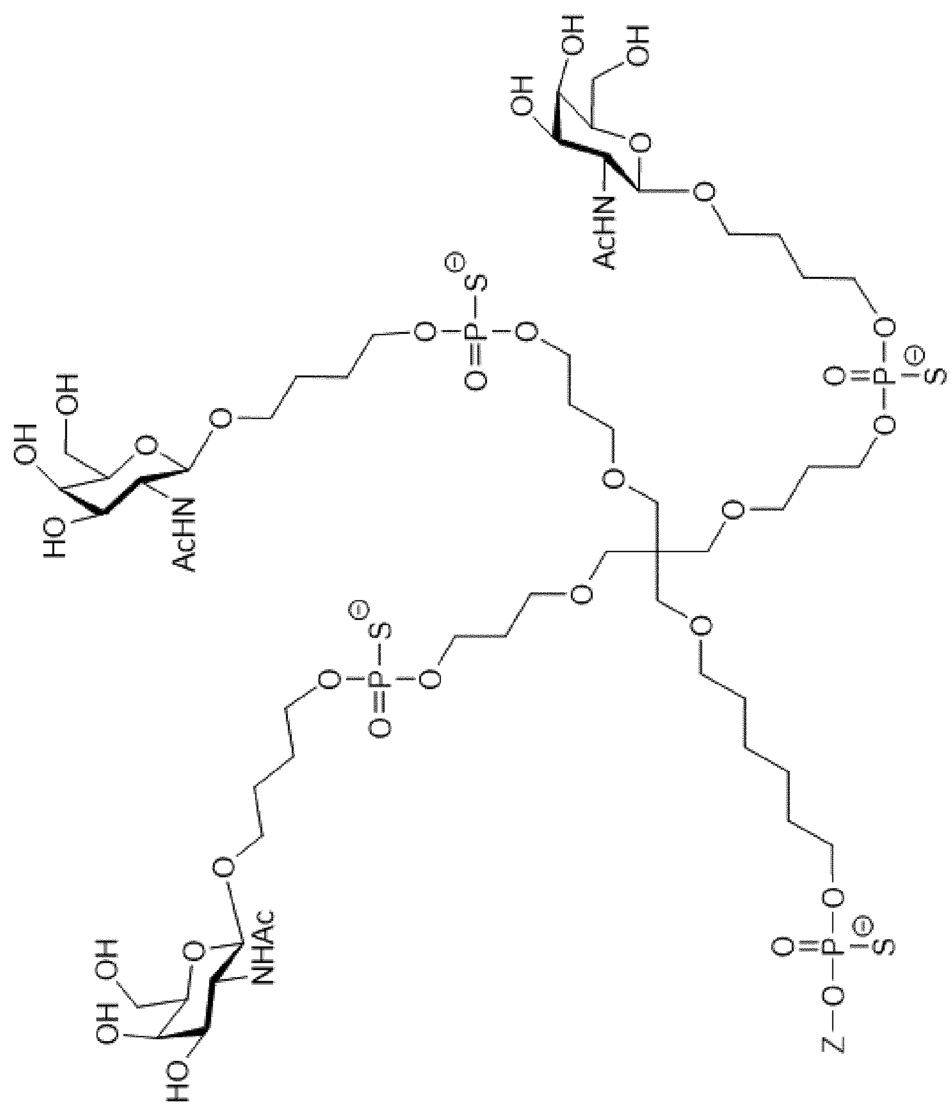

All single stranded oligonucleotides were synthesised according to the reaction conditions described above and in FIGS. 12, 16 and 17.

All final single stranded products were analysed by AEX-HPLC to prove their purity. Purity is given in % FLP (% full length product) which is the percentage of the UV-area under the assigned product signal in the UV-trace of the AEX-HPLC analysis of the final product. Identity of the respective single stranded products (non-modified, amino-modified precursors, C4XLT/ST23 or C6XLT/ST23 GalNAc conjugated oligonucleotides) was proved by LC-MS analysis.

TABLE 2

| Single stranded un-conjugated and on-column conjugated oligonucleotides | | | |
|---|---|---|---|
| Product | MW calc. | MW (ESI-) Found | % FLP (AEX-HPLC) |
| X0181A | 6943.3 Da | 6943.3 Da | 86.3% |
| X0349A | 6987.3 Da | 6986.7 Da | 93.4% |
| X0430A | 7019.3 Da | 7019.0 Da | 90.3% |
| X0322A | 6416.1 Da | 6416.1 Da | 94.1% |
| X0365A | 6437.0 Da | 6436.8 Da | 91.0% |
| X0431A | 6469.0 Da | 6468.7 Da | 84.3% |
| X0319A | 6237.8 Da | 6237.7 Da | 97.2% |
| X0362A | 6258.8 Da | 6258.2 Da | 91.3% |
| X0320A | 6143.8 Da | 6143.7 Da | 94.6% |
| X0363A | 6187.8 Da | 6187.3 Da | 85.4% |
| X0028A | 6259.9 Da | 6259.8 Da | 76.5% |
| X0027A | 6416.1 Da | 6415.8 Da | 92.8% |
| X0204A | 6469.0 Da | 6468.7 Da | 84.3% |
| X0205A | 6437.0 Da | 6436.8 Da | 91.0% |
| X0207A | 6393.1 Da | 6392.9 Da | 77.6% |
| X0477A | 6143.8 Da | 6143.4 Da | 85.6% |
| X0478A | 6187.8 Da | 6187.3 Da | 85.4% |
| X0181B-prec | 7183.3 da | 7183.2 Da | 88.8% |
| X0349B-prec | 7183.3 Da | 7183.3 Da | 96.2% |
| X0430B-prec | 7183.3 Da | 7183.3 Da | 96.2% |
| X0322B-prec | 6437.7 Da | 6437.8 Da | 91.1% |
| X0365B-prec | 6460.8 Da | 6460.9 Da | 92.9% |
| X0431B-prec | 6460.8 Da | 6460.9 Da | 92.9% |
| X0319B-prec | 6616.0 Da | 6616.0 Da | 75.6% |
| X0362B-prec | 6639.0 Da | 6639.0 Da | 85.7% |
| X0320B-prec | 6665.0 Da | 6664.8 Da | 87.0% |
| X0363B-prec | 6665.0 Da | 6664.8 Da | 81.7% |
| X0028B | 7813.2 Da | 7813.1 Da | 74.3% |
| X0027B | 7642.0 Da | 7641.8 Da | 88.2% |
| X0204B | 7665.0 Da | 7664.9 Da | 90.4% |
| X0205B | 7665.0 Da | 7664.9 Da | 90.4% |
| X0207B | 7665.0 Da | 7664.9 Da | 90.4% |
| X0477B-prec | 6749.3 Da | 6749.2 Da | 83.1% |
| X0478B-prec | 6749.3 Da | 6749.2 Da | 83.1% |

Synthesis of Conjugate with Serinol-Derived Linker

Conjugation of the GalNAc synthon (9) was achieved by coupling to the serinol-amino function of the respective oligonucleotide strand 11 using a peptide coupling reagent. Therefore, the respective amino-modified precursor molecule 11 was dissolved in $H_2O$ (500 OD/mL) and DMSO (DMSO/$H_2O$, 2/1, v/v) was added, followed by DIPEA (2.5% of total volume). In a separate reaction vessel pre-activation of the GalN(Ac4)-C4-acid (9) was performed by reacting 2 eq. (per amino function in the amino-modified precursor oligonucleotide 11) of the carboxylic acid component with 2 eq. of HBTU in presence of 8 eq. DIPEA in DMSO. After 2 min the pre-activated compound 9 was added to the solution of the respective amino-modified precursor molecule. After 30 min the reaction progress was monitored by LCMS or AEX-HPLC. Upon completion of the conjugation reaction the crude product was precipitated by addition of 10× iPrOH and 0.1×2M NaCl and harvested by centrifugation and decantation. To set free the acetylated hydroxyl groups in the GalNAc moieties the resulting pellet was dissolved in 40% MeNH2 (1 mL per 500 OD) and after 15 min at RT diluted in $H_2O$ (1:10) and finally purified again by anion exchange and size exclusion chromatography and lyophilised to yield the final product 12.

TABLE 3

| Single stranded GalNAc-conjugated oligonucleotides | | | | |
|---|---|---|---|---|
| Product (12) | Starting Material (11) | MW calc. | MW (ESI-) found | % FLP (AEX-HPLC) |
| X0181B | X0181B-prec | 7789.9 Da | 7789.8 Da | 95.5% |
| X0349B | X0349B-prec | 7789.9 Da | 7790.0 Da | 97.5% |
| X0430B | X0430B-prec | 7789.9 Da | 7790.0 Da | 97.5% |
| X0322B | X0322B-prec | 7044.4 Da | 7044.4 Da | 96.0% |
| X0365B | X0365B-prec | 7067.4 Da | 7067.2 Da | 95.7% |
| X0431B | X0431B-prec | 7067.4 Da | 7067.2 Da | 95.7% |
| X0319B | X0319B-prec | 7222.7 Da | 7222.9 Da | 82.5% |
| X0362B | X0362B-prec | 7245.7 Da | 7245.2 Da | 85.6% |
| X0320B | X0320B-prec | 7271.7 Da | 7271.7 Da | 90.0% |
| X0363B | X0363B-prec | 7271.7 Da | 7271.3 Da | 94.9% |
| X0477B | X0477B-prec | 7356.0 Da | 7355.7 Da | 91.4% |
| X0478B | X0478B-prec | 7356.0 Da | 7355.7 Da | 91.4% |

Double Strand Formation

Double strand formation was performed according to the methods described above. The double strand purity is given in % double strand which is the percentage of the UV-area under the assigned product signal in the UV-trace of the IPRP-HPLC analysis.

TABLE 4

| Nucleic acid conjugates | | | |
|---|---|---|---|
| Product | Starting First Strand | Materials Second Strand | % double strand |
| X0181 | X0181A | X0181B | 98.5 |
| X0349 | X0349A | X0349B | 98.8 |
| X0430 | X0430A | X0430B | 96.1 |
| X0322 | X0322A | X0322B | 98.0 |
| X0365 | X0365A | X0365B | 95.4 |
| X0431 | X0431A | X0431B | >99.0 |
| X0319 | X0319A | X0319B | 97.0 |
| X0362 | X0362A | X0362B | 98.3 |
| X0320 | X0320A | X0320B | 98.6 |
| X0363 | X0363A | X0363B | 94.5 |
| X0028 | X0028A | X0028B | 96.8 |
| X0027 | X0027A | X0027B | 93.4 |
| X0204 | X0204A | X0204B | 89.2 |
| X0205 | X0205A | X0205B | 92.0 |
| X0207 | X0207A | X0207B | 93.0 |
| X0477 | X0477A | X0477B | 96.0 |
| X0478 | X0478A | X0478B | 96.5 |

Example 13

Reduction of TMPRSS6 expression in primary murine hepatocytes by GalNAc siRNA conjugates with 2'-OMe-uridine or 5'-(E)-vinylphosphonate-2'-OMe-uridine replacing the 2'-OMe-adenin at the 5' position of the first strand.

Murine primary hepatocytes were seeded into collagen pre-coated 96 well plates (Thermo Fisher Scientific, #A1142803) at a cell density of 30,000 cells per well and treated with siRNA-conjugates at concentrations ranging from 100 nM to 0.1 nM. 24 h post treatment cells were lysed and RNA extracted with InviTrap® RNA Cell HTS 96 Kit/C24×96 preps (Stratec #7061300400) according to the manufactures protocol. Transcripts levels of TMPRSS6 and housekeeping mRNA (Ptenll) were quantified by TaqMan analysis.

siRNA Conjugates:

| siRNA duplex | first strand/ second strand | sequence & modification |
|---|---|---|
| STS12009L4 (X0027) | TMPRSS6-hcm9-A | mA (ps) fA (ps) mC fC mA fG mA fA mG fA mA fG mC fA mG fG mU (ps) fG (ps) mA |
| | TMPRSS6-hcm9-BL4 | GN2 fU mC fA mC fC mU fG mC fU mU fC mU fU mC fU mG fG (ps) mU (ps) fU |
| STS12209V4L4 (X0204) | TMPRSS6-hcm209AV4 | vinylphosphonate-mU (ps) fA (ps) mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS12209V5L4 (x0205) | TMPRSS6-hcm209-AV5 | vinylphosphonate-mU fA mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS12209L4 (x0207) | TMPRSS6-hcm209A | mU (ps) fA (ps) mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS12209V1L4 (x0208) | TMPRSS6-hcm9-AV1 | mU fA mC fC mA fG mA fA mG fA mA fG mC fA mG fG mU (ps) fG (ps) mA |
| | TMPRSS6-hcm209-BL4 | GN2 fU mC fA mC fC mU fG mC fU mU fC mU fU mC fU mG fG (ps) mU (ps) fA |
| STS18001 (X0028) | STS18001A | mU(ps)fC(ps)mGfAmAfGmUfAmUfUmCfCmGfCmGfUmA (ps)fC(ps)mG |
| | STS18001B L4 | GN2 fCmGfUmAfCmGfCmGfGmAfAmUfAmCfUmUfC(ps) mG (ps) fA |

TaqMan Primer and Probes

| | |
|---|---|
| PTEN-2 | CACCGCCAAATTTAACTGCAGA |
| PTEN-2 | AAGGGTTTGATAAGTTCTAGCTGT |
| PTEN-2 | FAM-TGCACAGTATCCTTTTGAAGACCATAACCCA-TAMRA |
| hTMPRSS6:379U17 | CCGCCAAAGCCCAGAAG |
| hTMPRSS6:475L21 | GGTCCCTCCCCAAAGGAATAG |
| hTMPRSS6:416U28FL | FAM-CAGCACCCGCCTGGGAACTTACTACAAC-BHQ1 |

In Vitro Dose Response

Target gene expression in primary murine hepatocytes 24 h following treatment with TMPRSS6-siRNA carrying vinyl-(E)-phosphonate 2'-OMe-Uracil at the 5-position of the antisense strand and two phosphorothioate linkages between the first three nucleotides (STS12209V4L4), vinyl-(E)-phosphonate 2'-OMe-Uracil at the 5-position of the anti-sense strand and phosphodiester bonds between the first three nucleotides (STS12209V5L4), carrying 2'-OMe-Uracil and two phosphorothioate linkages between the first three nucleotides at the 5-position (STS12209L4) or carrying 2'-OMe-Uracil or 2'-OMe-Adenine and two phosphodiester linkages between the first three nucleotides at the 5-position (STS12209V1L4 and STS12009L4) as reference or a non-targeting GalNAc-siRNA (STS18001) at indicated concentrations or left untreated (UT).

Figure 14:
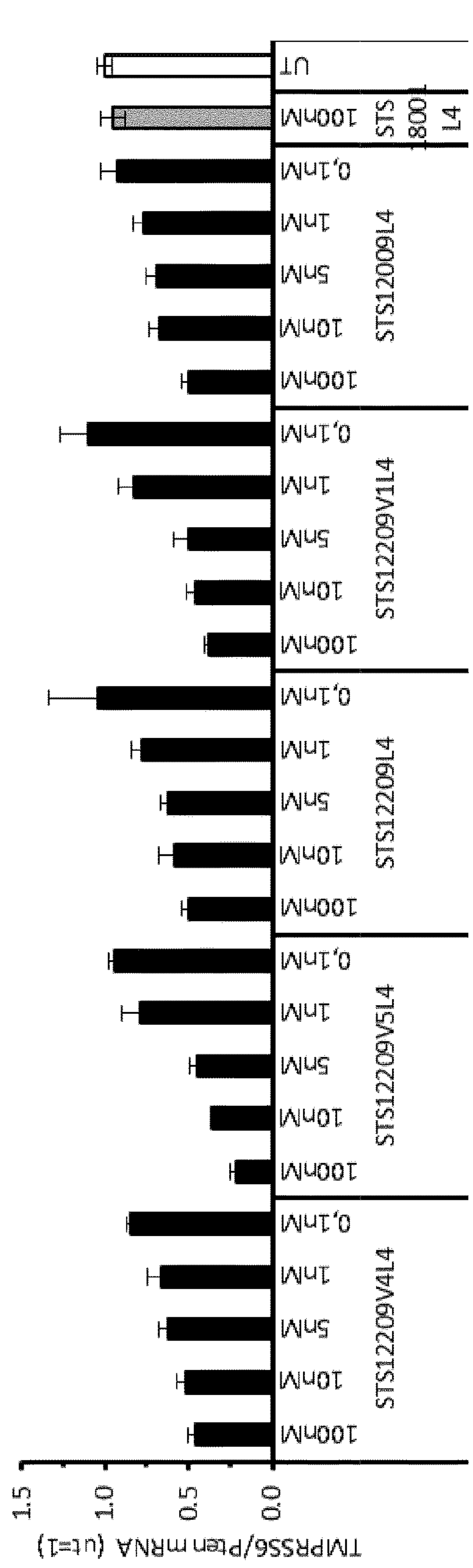
FIG. 14—shows inhibition of TMPRSS6 gene expression in primary murine hepatocytes 24 h following treatment with TMPRSS6-siRNA carrying vinyl-(E)-phosphonate 2'-OMe-Uracil at the 5-position of the anti-sense strand and two phosphorothioate linkages between the first three nucleotides (X0204), vinyl-(E)-phosphonate 2'-OMe-Uracil at the 5-position of the anti-sense strand and phosphodiester bonds between the first three nucleotides (X0205), (X0139) or tetrameric (X0140)) or a tree like trimeric GalNAc-cluster (X0004) or a non-targeting GalNAc-siRNA (X0028) at indicated concentrations or left untreated (UT).

Results are shown in FIG. 14. This figure confirms that a vinylphosphonate at the 5' end of the first strand, preferably in combination with phosphodiester linkages at the 5' end of the first strand lead to increased expression reduction of the target gene.

Serum Stability

Serum stability of siRNA conjugates incubated for 4 hours (4 h) or 3 days (3d) or left untreated (0 h) in 50% FCS at 37° C. RNA was then extracted by phenol/chlorophorm/isoamyl alcohol extraction. Degradation was visualized by TBE-Polyacrylamid-gel-electrophoresis and staining RNA with SybrGold.

Figure 15:
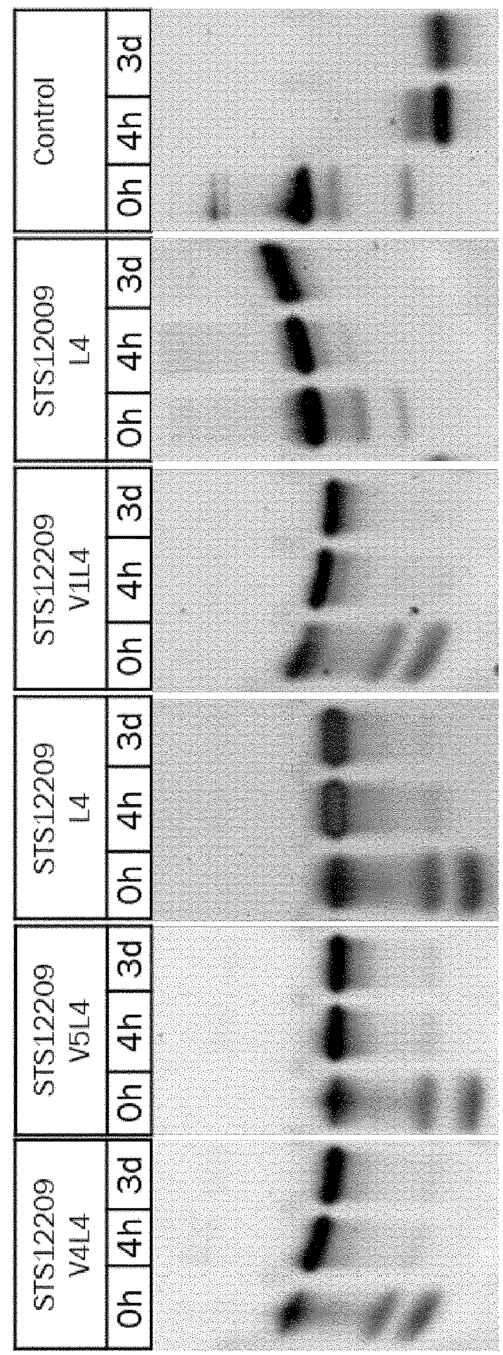
FIG. 15—shows Serum stability of siRNA-conjugates vs. less stabilized positive control for nuclease degradation.

Results are shown in FIG. 15: serum stability of siRNA-conjugates vs. less stabilized positive control for nuclease degradation.

Sequence Summary Table:

| SEQ ID | Seq name | Sequence 5'-3' | Unmodified sequence 5'-3' counterpart |
|---|---|---|---|
| 1 | X0181A | mU (ps) fU (ps) mA fU mA fG mA fG mC fA mA fG mA fA mC fA mC fU mG (ps) fU (ps) mU | UUAUAGAGCAAGAACACUGUU |
| 2 | X0181B | Ser(GN) (ps) fA (ps) mA (ps) fC mA fG mU fG mU fU mC fU mU fG mC fU mC fU mA fU (ps) mA (ps) fA (ps) Ser(GN) | AACAGUGUUCUUGCUCUAUAA |
| 3 | X0349A | (vp)-mU fU mA fU mA fG mA fG mC fA mA fG mA fA mC fA mC fU mG (ps) fU (ps) mU | UUAUAGAGCAAGAACACUGUU |
| 4 | X0349B | Ser(GN) (ps) fA (ps) mA (ps) fC mA fG mU fG mU fU mC fU mU fG mC fU mC fU mA fU (ps) mA (ps) fA (ps) Ser(GN) | AACAGUGUUCUUGCUCUAUAA |
| 5 | X0430A | (vp)-mU (ps) fU (ps) mA fU mA fG mA fG mC fA mA fG mA fA mC fA mC fU mG (ps) fU (ps) mU | UUAUAGAGCAAGAACACUGUU |
| 6 | X0430B | Ser(GN) (ps) fA (ps) mA (ps) fC mA fG mU fG mU fU mC fU mU fG mC fU mC fU mA fU (ps) mA (ps) fA (ps) Ser(GN) | AACAGUGUUCUUGCUCUAUAA |
| 7 | X0322A | mA (ps) fA (ps) mC fC mA fG mA fA mG fA mA fG mC fA mG fG mU (ps) fG (ps) mA | AACCAGAAGAAGCAGGUGA |
| 8 | X0322B | Ser(GN) (ps) fU (ps) mC (ps) fA mC fC mU fG mC fU mU fC mU fU mC fU mG fG (ps) mU (ps) fU (ps) Ser(GN) | UCACCUGCUUCUUCUGGUU |
| 9 | X0365A | (vp)-mU fA mC fC mA fG mA fA mG fA mA fG mC fA mG fG mU (ps) fG (ps) mA | UACCAGAAGAAGCAGGUGA |
| 10 | X0365B | Ser(GN) (ps) fU (ps) mC (ps) fA mC fC mU fG mC fU mU fC mU fU mC fU mG fG (ps) mU (ps) fA (ps) Ser(GN) | UCACCUGCUUCUUCUGGUA |
| 11 | X0431A | (vp)-mU (ps) fA (ps) mC fC mA fG mA fA mG fA mA fG mC fA mG fG mU (ps) fG (ps) mA | UACCAGAAGAAGCAGGUGA |
| 12 | X0431B | Ser(GN) (ps) fU (ps) mC (ps) fA mC fC mU fG mC fU mU fC mU fU mC fU mG fG (ps) mU (ps) fA (ps) Ser(GN) | UCACCUGCUUCUUCUGGUA |
| 13 | X0319A | mA (ps) fA (ps) mU fG mU fU mU fU mC fC mU fG mC fU mG fA mC (ps) fG (ps) mG | AAUGUUUUCCUGCUGACGG |
| 14 | X0319B | Ser(GN) (ps) fC (ps) mC (ps) fG mU fC mA fG mC fA mG fG mA fA mA fA mC fA (ps) mU (ps) fU (ps) Ser(GN) | CCGUCAGCAGGAAAACAUU |
| 15 | X0362A | (vp)-mU fA mU fG mU fU mU fU mC fC mU fG mC fU mG fA mC (ps) fG (ps) mG | UAUGUUUUCCUGCUGACGG |
| 16 | X0362**B** | Ser(GN) (ps) fC (ps) mC (ps) fG mU fC mA fG mC fA mG fG mA fA mA fA mC fA (ps) mU (ps) fA (ps) Ser(GN) | CCGUCAGCAGGAAAACAUA |

-continued

Sequence Summary Table:

| SEQ ID | Seq name | Sequence 5'-3' | Unmodified sequence 5'-3' counterpart |
|---|---|---|---|
| 17 | X0320A | mU (ps) fC (ps) mU fU mC fU mU fA mA fA mC fU mG fA mG fU mU (ps) fU (ps) mC | UCUUCUUAAACUGAGUUUC |
| 18 | X0320**B** | Ser(GN) (ps) fG (ps) mA (ps) fA mA fC mU fC mA fG mU fU mU fA mA fG mA fA (ps) mG (ps) fA (ps) Ser(GN) | GAAACUCAGUUUAAGAAGA |
| 19 | X0363A | (vp)-mU fC mU fU mC fU mU fA mA fA mC fU mG fA mG fU mU (ps) fU (ps) mC | UCUUCUUAAACUGAGUUUC |
| 20 | X0363**B** | Ser(GN) (ps) fG (ps) mA (ps) fA mA fC mU fC mA fG mU fU mU fA mA fG mA fA (ps) mG (ps) fA (ps) Ser(GN) | GAAACUCAGUUUAAGAAGA |
| 21 | X0028A | mU (ps) fC (ps) mG fA mA fG mU fA mU fU mC fC mG fC mG fU mA (ps) fC (ps) mG | UCGAAGUAUUCCGCGUACG |
| 22 | X0028**B** | [ST23 (ps)]3 ST41(ps) fC mG fU mA fC mG fC mG fG mA fA mU fA mC fU mU fC (ps) mG (ps) fA | CGUACGCGGAAUACUUCGA |
| 23 | X0027A | mA (ps) fA (ps) mC fC mA fG mA fA mG fA mA fG mC fA mG fG mU (ps) fG (ps) mA | AACCAGAAGAAGCAGGUGA |
| 24 | X0027**B** | [ST23 (ps)]3 ST41 (ps) fU (ps) mC (ps) fA mC fC mU fG mC fU mU fC mU fU mC fU mG fG (ps) mU (ps) fU | UCACCUGCUUCUUCUGGUU |
| 25 | X0204A | (vp)-mU (ps) fA (ps) mC fC mA fG mA fA mG fA mA fG mC fA mG fG mU (ps) fG (ps) mA | UACCAGAAGAAGCAGGUGA |
| 26 | X0204**B** | [ST23 (ps)]3 ST41 (ps) fU mC fA mC fC mU fG mC fU mU fC mU fU mC fU mG fG (ps) mU (ps) fA | UCACCUGCUUCUUCUGGUA |
| 27 | X0205A | (vp)-mU fA mC fC mA fG mA fA mG fA mA fG mC fA mG fG mU (ps) fG (ps) mA | UACCAGAAGAAGCAGGUGA |
| 28 | X0205**B** | [ST23 (ps)]3 ST41 (ps) fU mC fA mC fC mU fG mC fU mU fC mU fU mC fU mG fG (ps) mU (ps) fA | UCACCUGCUUCUUCUGGUA |
| 29 | X0207A | mU (ps) fA (ps) mC fC mA fG mA fA mG fA mA fG mC fA mG fG mU (ps) fG (ps) mA | UACCAGAAGAAGCAGGUGA |
| 30 | X0207**B** | [ST23 (ps)]3 ST41 (ps) fU mC fA mC fC mU fG mC fU mU fC mU fU mC fU mG fG (ps) mU (ps) fA | UCACCUGCUUCUUCUGGUA |
| 31 | X0477A | mU (ps) fC (ps) mU fU mC fU mU fA mA fA mC fU mG fA mG fU mU (ps) fU (ps) mC | UCUUCUUAAACUGAGUUUC |
| 32 | X0477B | Ser(GN) (ps) mG (ps) mA (ps) mA mA mC mU fC fA fG mU mU mU mA mA mG mA mA (ps) mG (ps) mA (ps) Ser(GN) | GAAACUCAGUUUAAGAAGA |

-continued

Sequence Summary Table:

| SEQ ID | Seq name | Sequence 5'-3' | Unmodified sequence 5'-3' counterpart |
|---|---|---|---|
| 33 | X0478A | (vp)-mU fC mU fU mC fU mU fA mA fA mC fU mG fA mG fU mU (ps) fU (ps) mC | UCUUCUUAAACUGAGUUUC |
| 34 | X0478B | Ser(GN) (ps) mG (ps) mA (ps) mA mA mC mU fC fA fG mU mU mU mA mA mG mA mA (ps) mG (ps) mA (ps) Ser(GN) | GAAACUCAGUUUAAGAAGA |
| 35 | mTTR fw primer | TGGACACCAAATCGTACTGGAA | TGGACACCAAATCGTACTGGAA |
| 36 | mTTR rev primer | CAGAGTCGTTGGCTGTGAAAAC | CAGAGTCGTTGGCTGTGAAAAC |
| 37 | mTTR probe primer | BHQ1-ACTTGGCATTTCCCCGTTCCATGAATT-FAM | ACTTGGCATTTCCCCGTTCCAT GAATT |
| 38 | hTMPRSS6fw primer | CCGCCAAAGCCCAGAAG | CCGCCAAAGCCCAGAAG |
| 39 | hTMPRSS6 rev primer | GGTCCCTCCCCAAAGGAATAG | GGTCCCTCCCCAAAGGAATAG |
| 40 | hTMPRSS6 probe primer | BHQ1-CAGCACCCGCCTGGGAACTTACTACAAC-FAM | CAGCACCCGCCTGGGAACTTAC TACAAC |
| 41 | ALDH2 fw primer | GGCAAGCCTTATGTCATCTCGT | |
| 42 | ALDH2 rev primer | GGAATGGTTTTCCCATGGTACTT | GGAATGGTTTTCCCATGGTACT T |
| 43 | ALDH2 probe primer | BHQ1-TGAAATGTCTCCGCTATTACGCTGGCTG-FAM | TGAAATGTCTCCGCTATTACGC TGGCTG |
| 44 | ApoB fw primer | AAAGAGGCCAGTCAAGCTGTTC | AAAGAGGCCAGTCAAGCTGTTC |
| 45 | ApoB rev primer | GGTGGGATCACTTCTGTTTTGG | GGTGGGATCACTTCTGTTTTGG |
| 46 | ApoB probe primer | BHQ1-CAGCAACACACTGCATCTGGTCTCTACCA-VIC | CAGCAACACACTGCATCTGGTC TCTACCA |
| 47 | PTEN fw primer | CACCGCCAAATTTAACTGCAGA | CACCGCCAAATTTAACTGCAGA |

-continued

Sequence Summary Table:

| SEQ ID | Seq name | Sequence 5'-3' | Unmodified sequence 5'-3' counterpart |
|---|---|---|---|
| 48 | PTEN rev primer | AAGGGTTTGATAAGTTCTAGCTGT | AAGGGTTTGATAAGTTCTAGCT GT |
| 49 | PTEN probe primer | BHQ1-TGCACAGTATCCTTTTGAAGACCATAACCCA-VIC | TGCACAGTATCCTTTTGAAGAC CATAACCCA |
| 50 | TMPRSS6-hcm9-A | mA (ps) fA (ps) mC fC mA fG mA fA mG fA mA fG mC fA mG fG mU (ps) fG (ps) mA | AACCAGAAGAAGCAGGUGA |
| 51 | TMPRSS6-hcm9-BL4 | GN2 fU mC fA mC fC mU fG mC fU mU fC mU fU mC fU mG fG (ps) mU (ps) fU | UCACCUGCUUCUUCUGGUU |
| 52 | TMPRSS6-hcm209AV4 | vinylphosphonate-mU (ps) fA (ps) mC fC mA fG mA fA mG fA mA fG mC fA mG fG mU (ps) fG (ps) mA | UACCAGAAGAAGCAGGUGA |
| 53 | TMPRSS6-hcm209-BL4 | GN2 fU mC fA mC fC mU fG mC fU mU fC mU fU mC fU mG fG (ps) mU (ps) fA | UCACCUGCUUCUUCUGGUA |
| 54 | TMPRSS6-hcm209-AVS | vinylphosphonate-mU fA mC fC mA fG mA fA mG fA mA fG mC fA mG fG mU (ps) fG (ps) mA | UACCAGAAGAAGCAGGUGA |
| 55 | TMPRSS6-hcm209-BL4 | GN2 fU mC fA mC fC mU fG mC fU mU fC mU fU mC fU mG fG (ps) mU (ps) fA | UCACCUGCUUCUUCUGGUA |
| 56 | TMPRSS6-hcm209A | mU (ps) fA (ps) mC fC mA fG mA fA mG fA mA fG mC fA mG fG mU (ps) fG (ps) mA | UACCAGAAGAAGCAGGUGA |
| 57 | TMPRSS6-hcm209-BL4 | GN2 fU mC fA mC fC mU fG mC fU mU fC mU fU mC fU mG fG (ps) mU (ps) fA | UCACCUGCUUCUUCUGGUA |
| 58 | TMPRSS6-hcm9-AV1 | mU fA mC fC mA fG mA fA mG fA mA fG mC fA mG fG mU (ps) fG (ps) mA | UACCAGAAGAAGCAGGUGA |
| 59 | TMPRSS6-hcm209-BL4 | GN2 fU mC fA mC fC mU fG mC fU mU fC mU fU mC fU mG fG (ps) mU (ps) fA | UCACCUGCUUCUUCUGGUA |
| 60 | STS18001A | mU(ps)fC(ps)mGfAmAfGmUfAmUfUmCfCmGfCmGfUmA(ps)fC(ps)mG | UCGAAGUAUUCCGCGUACG |
| 61 | STS18001BL4 | GN2 fCmGfUmAfCmGfCmGfGmAfAmUfAmCfUmUfC (ps) mG (ps) fA | CGUACGCGGAAUACUUCGA |
| 62 | PTEN-2 | CACCGCCAAATTTAACTGCAGA | CACCGCCAAATTTAACTGCAGA |
| 63 | PTEN-2 | AAGGGTTTGATAAGTTCTAGCTGT | AAGGGTTTGATAAGTTCTAGCT GT |
| 64 | PTEN-2 | FAM-TGCACAGTATCCTTTTGAAGACCATAACCCA-TAMRA | TGCACAGTATCCTTTTGAAGAC CATAACCCA |

-continued

Sequence Summary Table:

| SEQ ID | Seq name | Sequence 5'-3' | Unmodified sequence 5'-3' counterpart |
|---|---|---|---|
| 65 | hTMPRSS6: 379U17 | CCGCCAAAGCCCAGAAG | CCGCCAAAGCCCAGAAG |
| 66 | hTMPRSS6: 475L21 | GGTCCCTCCCCAAAGGAATAG | GGTCCCTCCCCAAAGGAATAG |
| 67 | hTMPRSS6: 416U28FL | FAM-CAGCACCCGCCTGGGAACTTACTACAAC-BHQ1 | CAGCACCCGCCTGGGAACTTAC TACAAC |
| 68 | TMPRSS6 AS | (vp)-UACCAGAAGAAGCAGGUGA | UACCAGAAGAAGCAGGUGA |
| 69 | TMPRSS6 S un | UCACCUGCUUCUUCUGGUA | UCACCUGCUUCUUCUGGUA |
| 70 | TMPRSS6S | fU (ps) mC (ps) fA mC fC mU fG mC fU mU fC mU fU mC fU mG fG (ps) mU (ps) fA | UCACCUGCUUCUUCUGGUA |
| 71 | TTR AS | (vp)-UUAUAGAGCAAGAACACUGUU | UUAUAGAGCAAGAACACUGUU |
| 72 | TTR S un | AACAGUGUUCUUGCUCUAUAA | AACAGUGUUCUUGCUCUAUAA |
| 73 | TTR S | fA (ps) mA (ps) fC mA fG mU fG mU fU mC fU mU fG mC fU mC fU mA fU (ps) mA (ps) fA | AACAGUGUUCUUGCUCUAUAA |
| 74 | ALDH2 AS | (vp)-UCUUCUUAAACUGAGUUUC | UCUUCUUAAACUGAGUUUC |
| 75 | ALDH2 S un | GAAACUCAGUUUAAGAAGA | GAAACUCAGUUUAAGAAGA |
| 76 | ALDH2 S ABA | mG (ps) mA (ps) mA mA mC mU fC fA fG mU mU mU mA mA mG mA mA (ps) mG (ps) mA | GAAACUCAGUUUAAGAAGA |
| 77 | ALDH2 S Alt | fG (ps) mA (ps) fA mA fC mU fC mA fG mU fU mU fA mA fG mA fA (ps) mG (ps) fA | GAAACUCAGUUUAAGAAGA |

The sequences listed above may be disclosed with a linker or ligand, such as GalNAc or (ps) linkages for example. These form an optional, but preferred, part of the sequence of the sequence listing.

Summary Abbreviations Table

| Abbreviation | Meaning |
|---|---|
| A, U, C, G | adenine, uracil, cytosine, guanine |
| mA, mU, mC, mG | 2'-O-Methyl RNA nucleotides |
| 2'-OMe | 2'-O-Methyl modification |
| fA, fU, fC, fG | 2' deoxy-2'-F RNA nucleotides |
| 2'-F | 2'-fluoro modification |
| (ps) | phosphorothioate |
| FAM | 6-Carboxyfluorescein |
| TAMRA | 5-Carboxytetramethylrhodamine |
| BHQ1 | Black Hole Quencher 1 |
| (vp) or vinylphosphonate | Vinyl-(E)-phosphonate |
| (vp)-mU | |
| (vp)-mU-phos | |
| ST23 | |
| ST23-phos | |
| ST41 (or C4XLT) | |

-continued
| Abbreviation | Meaning |
|---|---|
| ST41-phos (or C4XLT-phos) | 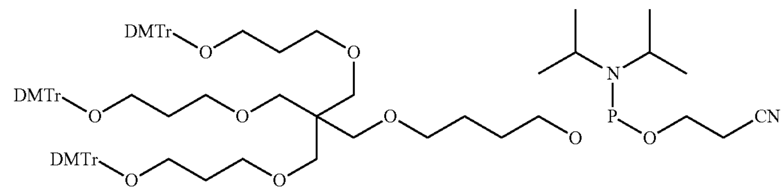 |
| ST43 (or C6XLT) | 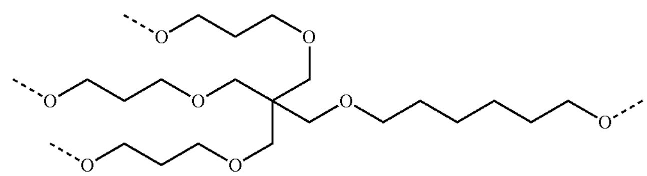 |
| ST43-phos (or C6XLT-phos) | 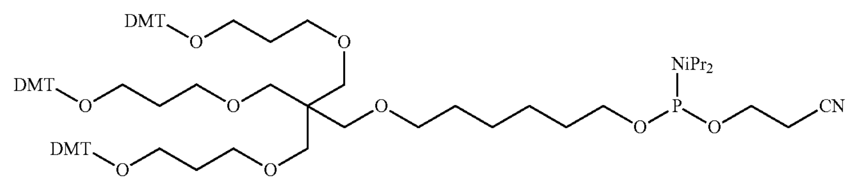 |
| GN | 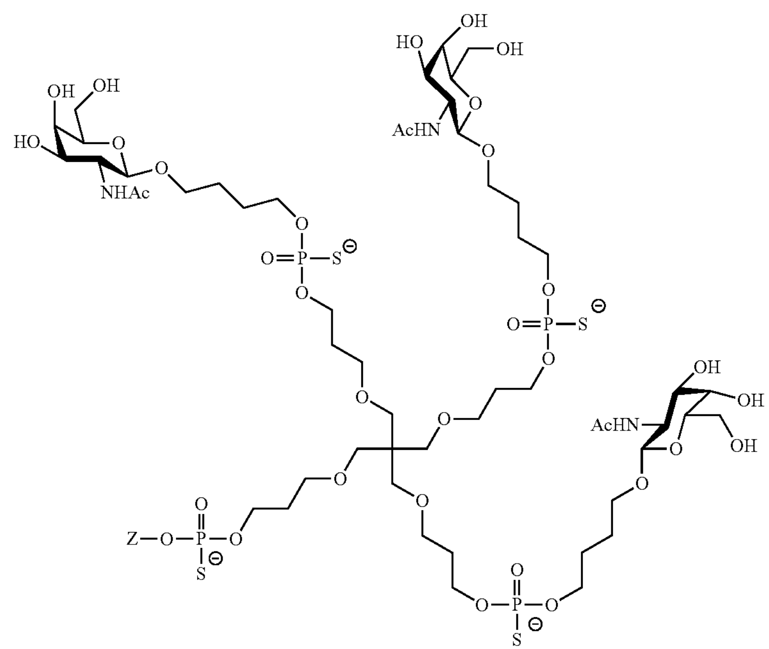 |

-continued
| Abbreviation | Meaning |
|---|---|
| GN2 or [ST23 (ps)]3 ST41 (ps) | 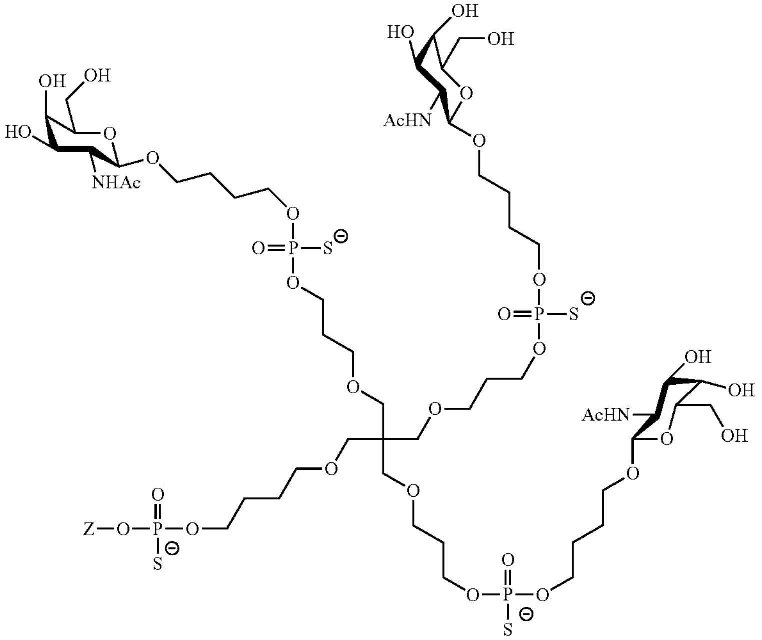 |
| GN3 or [ST23 (ps)]3 ST43 (ps) | 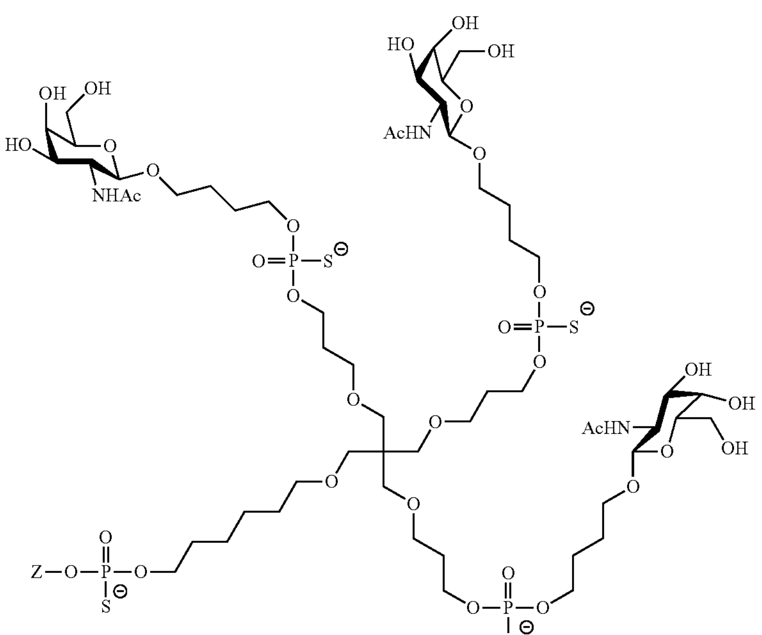 |
| Ser(GN) | 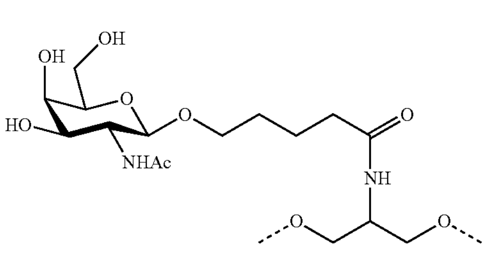 |
| O---- | linkage between the oxygen atom and e.g. H, phosphodiester linkage or phosphorothioate linkage |

The abbreviations as shown in this abbreviation table may be used herein. The list of abbreviations may not be exhaustive and further abbreviations and their meaning may be found throughout this document.

The invention claimed is:

1. A nucleic acid for inhibiting expression of a target gene in a cell, comprising at least one duplex region that comprises at least a portion of a first strand and at least a portion of a second strand that is at least partially complementary to the first strand, wherein said first strand is at least partially complementary to at least a portion of RNA transcribed from said target gene to be inhibited, wherein:

the first strand has a terminal 5' (E)-vinylphosphonate nucleotide;

the terminal 5' (E)-vinylphosphonate nucleotide is linked to the second nucleotide in the first strand by a phosphodiester linkage;

all even-numbered nucleotides of the first strand are modified by a 2'-F modification;

all odd-numbered nucleotides of the first strand are modified by a 2'-OMe modification;

all nucleotides of the second strand in positions corresponding to nucleotides 11-13 of the first strand are modified by a 2'-F modification; and all nucleotides of the second strand other than the nucleotides corresponding to nucleotides 11-13 of the first strand are modified by a 2'-OMe modification.

2. The nucleic acid of claim 1, wherein the first strand comprises more than 1 phosphodiester linkage.

3. The nucleic acid of claim 1, wherein the first strand comprises phosphodiester linkages between i) at least the terminal three 5' nucleotides; or ii) at least the terminal four 5' nucleotides.

4. The nucleic acid of claim 1, wherein the first strand comprises i) at least one phosphorothioate (ps) linkage.

5. The nucleic acid of claim 1, wherein the first strand comprises i) a phosphorothioate linkage between the terminal two 3' nucleotides; or ii) phosphorothioate linkages between the terminal three 3' nucleotides.

6. The nucleic acid of claim 5, wherein the linkages between the other nucleotides in the first strand are phosphodiester linkages.

7. The nucleic acid of claim 1, wherein the second strand comprises i) a phosphorothioate linkage between the terminal two or three 3' nucleotides; and/or ii) a phosphorothioate linkage between the terminal two or three 5' nucleotides.

8. The nucleic acid of claim 1, wherein the terminal 5' (E)-vinylphosphonate nucleotide is an RNA nucleotide.

9. The nucleic acid of claim 1, wherein i) the first strand of the nucleic acid has a length in the range of 15-30 nucleotides; and/or ii) the second strand of the nucleic acid has a length in the range of 15-30 nucleotides.

10. A conjugate for inhibiting expression of a target gene in a cell, said conjugate comprising a nucleic acid portion and one or more ligand portions, said nucleic acid portion comprising a nucleic acid as defined in claim 1.

11. The conjugate of claim 10, wherein the second strand of the nucleic acid is conjugated to the one or more ligand portion(s).

12. The conjugate of claim 10, wherein the ligand portion comprises i) one or more GalNAc ligand;

ii) one or more GalNAc ligand derivative; or iii) a GalNAc moiety conjugated at the 5' end of the second strand of the nucleic acid.

13. A composition comprising a nucleic acid of any one of claims 1 to 9 or a conjugate of any one of claims 10 to 12 and a physiologically acceptable excipient.

14. The nucleic acid of claim 9, wherein:

i) the first strand of the nucleic acid has a length in the range of 19-25 nucleotides; and/or ii) the second strand of the nucleic acid has a length in the range of 19-25 nucleotides.

15. The conjugate of claim 12, wherein the ligand portion comprises a GalNAc moiety conjugated at the 5' end of the second strand of the nucleic acid through a linker moiety.

16. A method for prophylaxis or treatment of a disease or disorder in a subject in need thereof, comprising administering a nucleic acid according to any one of claims 1 to 9 or a conjugate according to any one of claims 10 to 12, to said subject.

* * * * *